US008637555B2

(12) United States Patent
Semple et al.

(10) Patent No.: US 8,637,555 B2
(45) Date of Patent: Jan. 28, 2014

(54) TETRAZOLE DERIVATIVES AND METHODS OF TREATMENT OF METABOLIC-RELATED DISORDERS THEREOF

(75) Inventors: Graeme Semple, San Diego, CA (US); Thomas Schrader, La Jolla, CA (US); Philip J. Skinner, San Diego, CA (US); Steven L. Colletti, Princeton Junction, NJ (US); Tawfik Gharbaoui, Escondido, CA (US); Jason E. Imbriglio, Piscataway, NJ (US); Jae-Kyu Jung, San Diego, CA (US); Rui Liang, East Brunswick, NJ (US); Subharekha Raghavan, Teaneck, NJ (US); Darby Schmidt, Clark, NJ (US); James R. Tata, Westfield, NJ (US)

(73) Assignees: Arena Pharmaceuticals, Inc., San Diego, CA (US); Merck & Co., Inc., Rahway, NJ (US)

( * ) Notice: Subject to any disclaimer, the term of this patent is extended or adjusted under 35 U.S.C. 154(b) by 1277 days.

(21) Appl. No.: 10/535,345

(22) PCT Filed: Oct. 29, 2004

(86) PCT No.: PCT/US2004/035927
§ 371 (c)(1),
(2), (4) Date: Feb. 15, 2006

(87) PCT Pub. No.: WO2005/044816
PCT Pub. Date: May 19, 2005

(65) Prior Publication Data
US 2006/0217562 A1    Sep. 28, 2006

Related U.S. Application Data

(60) Provisional application No. 60/516,238, filed on Oct. 31, 2003.

(51) Int. Cl.
*A61K 31/407* (2006.01)
*C07D 231/54* (2006.01)

(52) U.S. Cl.
USPC ............ 514/359; 514/381; 548/250; 548/255

(58) Field of Classification Search
USPC .......................... 514/359, 381; 548/250, 255
See application file for complete search history.

(56) References Cited

U.S. PATENT DOCUMENTS

| 5,948,786 | A | 9/1999 | Fujiwara et al. |
| 6,414,002 | B1 | 7/2002 | Cheng et al. |
| 7,056,942 | B2 | 6/2006 | Hildesheim et al. |
| 7,105,523 | B2 | 9/2006 | Stasch et al. |
| 7,157,466 | B2 | 1/2007 | McClure et al. |
| 7,173,037 | B2 | 2/2007 | Alonso-Alija et al. |
| 7,211,591 | B2 | 5/2007 | Tajima et al. |
| 7,229,991 | B2 | 6/2007 | Merla et al. |
| 7,230,024 | B2 | 6/2007 | Carpino et al. |
| 7,232,823 | B2 | 6/2007 | Carpino et al. |
| 7,241,792 | B2 | 7/2007 | Boatman et al. |
| 2007/0072924 | A1* | 3/2007 | Semple et al. ................. 514/381 |
| 2007/0073062 | A1 | 3/2007 | Boatman et al. |

FOREIGN PATENT DOCUMENTS

| DE | 10148617 A1 | 4/2003 |
| EP | 0529854 | 3/1993 |
| EP | 05298854 A2 | 3/1993 |
| EP | 1305286 B1 | 12/2004 |
| EP | 1 599 469 | 6/2006 |
| WO | WO98/28269 | 7/1998 |
| WO | WO0166520 A1 | 9/2001 |
| WO | WO0179169 A2 | 10/2001 |
| WO | WO02094830 A2 | 11/2002 |

(Continued)

OTHER PUBLICATIONS

Sparatore, et al., Chem & Biodiver., vol. 3, 2006, 385-395, especially p. 390.*

(Continued)

*Primary Examiner* — Susannah Chung
(74) *Attorney, Agent, or Firm* — Fish & Richardson; Lyle W. Spruce

(57) ABSTRACT

The present invention relates to certain tetrazole derivatives of Formula (I), and pharmaceutically acceptable salts thereof, which exhibit useful pharmacological properties, for example, as agonists for the RUP25 receptor.

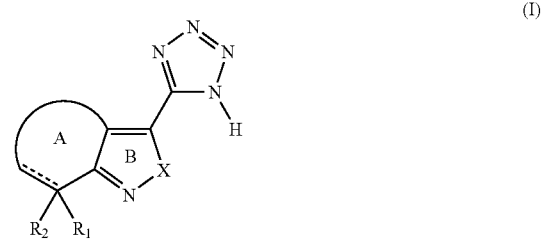

Also provided by the present invention are pharmaceutical compositions containing compounds of the invention, and methods of using the compounds and compositions of the invention in the treatment of metabolic-related disorders, including dyslipidemia, atherosclerosis, coronary heart disease, insulin resistance, type 2 diabetes, Syndrome-X and the like. In addition, the present invention also provides for the use of the compounds of the invention in combination with other active agents such as those belonging to the class of α-glucosidase inhibitors, aldose reductase inhibitors, biguanides, HMG-CoA reductase inhibitors, squalene synthesis inhibitors, fibrates, LDL catabolism enhancers, angiotensin converting enzyme (ACE) inhibitors, insulin secretion enhancers and the like.

2 Claims, No Drawings

(56) References Cited

FOREIGN PATENT DOCUMENTS

| | | |
|---|---|---|
| WO | WO02098864 | 12/2002 |
| WO | WO03002544 | 1/2003 |
| WO | WO03002582 A1 | 1/2003 |
| WO | WO03022814 A1 | 3/2003 |
| WO | WO03062200 A2 | 7/2003 |
| WO | WO03078409 A1 | 9/2003 |
| WO | WO 2004/032928 | 4/2004 |
| WO | WO 2004/033431 | 4/2004 |
| WO | WO2004103370 A1 | 12/2004 |
| WO | WO 2005/011677 | 2/2005 |
| WO | WO 2005/016867 | 2/2005 |
| WO | WO 2005/016870 | 2/2005 |
| WO | WO2005044816 A1 | 5/2005 |
| WO | WO 2005/077950 | 8/2005 |
| WO | WO 2006026273 | 3/2006 |
| WO | WO 2006052569 | 5/2006 |
| WO | WO2006/069242 A2 | 6/2006 |
| WO | WO 2006114581 | 11/2006 |

OTHER PUBLICATIONS

Semple, et al., J. Med. Chem. 2006, 49, 1227-1230, especially p. 1229.*

Biotech, Chem, Pharm Customer Partnership Meeting, Mar. 12, 2008.*

Semple, et al., J. Med. Chem., 2006, 49, 1227-1230.*

Mahley, R. et al., "Drug therapy for hypercholesterolemia and dyslipidemia", Goodman & Gilman 36:971-1002.

Olivo, H. et al., "Synthetic studies on the trans-Chlorocyclopropane dienyne side chain of Callipeltoside-A", Org. Lett. 2(25):4055-8 (2000)(supporting information attached).

Higuchi et al., "Pro-drugs as novel delivery systems," vol. 14 of the A.C.S. Symposium Series.

Flechtner-Mors et al., "Effects of acipimox on the lipolysis rate in subcutaneous adipose tissue of obese subjects," *Diabetes/Metabolism Research and Reviews* (2001)17:387-390.

Guillory, "Generation of Polymorphs, Hydrates, Solvates, and Amorphous Solids", in *Polymorphism in Pharmaceutical Solids*, ed. Harry G. Brittain, vol. 95, Chap. 5, Marcel Dekker, Inc., New York, 1999, pp. 183-226.

Karpe, F., et al, "The nicotinic acid receptor—a new mechanism for an old drug", The Lancet, vol. 363, Jun. 5, 2004, pp. 1892-1894.

Kubota, N., et al, "Disruption of Adiponectin Causes Insulin Resistance and Neointimal Formation", The Journal of Biological Chemistry, vol. 277, No. 29, Jul. 19, 2002, pp. 25863-25866.

Li, J., et al, "Effect of niacin on adiponectin levels in the adipocytes secretion in rabbits", Dept. of Cardiovasology, Second Xiangya Hospital, Central South University, Changsha, China, (2007) pp. 480-484.

Okamoto, Y., et al, "Adiponectin Reduces Atherosclerosis in Apolipoprotein E-Deficient Mice", Circulation—Journal of the American Heart Association, Nov. 26, 2002, pp. 2767-2770, [retrieved from the Internet on Apr. 24, 2008] http://www.circ.ahajournals.org.

Tunaru, S., et al, "PUMA-G and HM74 are receptors for nicotinic acid and mediate its anti-lipolytic effect", Nature Medicine, Mar. 2003, vol. 9, pp. 352-355 (with "Supplementary Methods" included, one page).

Zhang, et al, "Niacin mediates lipolysis in adipose tissue through its G-protein coupled receptor HM74A", Biochemical and Biophysical Research Communications, (2005) 334, pp. 729-732.

Restriction Requirement from copending U.S. Appl. No. 11/601,252 dated May 15, 2007.

Non-Final Office Action from copending U.S. Appl. No. 11/601,252 dated Jan. 8, 2008.

Final Office Action from copending U.S. Appl. No. 11/601,252 dated Oct. 20, 2008.

International Search Report for International Application No. PCT/US2004/035927 (dated Apr. 6, 2005).

International Preliminary Report on Patentability for International Application No. PCT/US2004/035927 (dated Oct. 10, 2005).

Wilson, Robert D., et al., "Development of a Scaleable Synthesis of a Partial Nicotinic Acid Receptor Agonist", Organic Process Research & Development, Article APAP, DOI: 10.1021/op800290t (Mar. 16, 2009).

Semple, Graeme, et al., "3-(1H-Tetrazol-5-yl)-1,4,5,6-tetrahydro-cyclopentapyrazole (MK-0354): A Partial Agonist of the Nicotinic Acid Receptor, G-Protein Coupled Receptor 109a, with Antilipolytic but No Vasodilatory Activity in Mice", Journal of Medicinal Chemistry (2008), 51(16), 5101-5108.

Press Release, Arena Pharmaceuticals, Arena Pharmaceuticals Announces Update on Partnership With Merck in Development of Niacin Receptor Agonists, San Diego, CA (Sep. 25, 2006).

Le Bas et al., "Radioiodinated analogs of EP 00652218 for the exploration of the tachykinin NK1 receptor by spect," *J. Labelled Cpd. Radiopharm.* (2001) 44(Suppl 1):S280-S282.

Bays et al., "Pharmacotherapy for dyslipidaemia—current therapies and future agents," *Expert Opinion on Pharmacotherapy* (2003) 4(11):1901-1938.

Chang et al., "Ciglitazone, a new hypoglycemic agent. I. Studies in ob/ob and db/db mice, diabetic Chinese hamsters, and normal and streptozotocin-diabetic rats," *Diabetes* (1983) 32:830-838.

Collier et al., "Radiosynthesis and in-vivo evaluation of the pseudopeptide δ-opioid antagonist [$^{125}$I]-ITIPP(Ψ)," *J. Labelled Cpd. Radiopharm* (1999) 42(Suppl 1):S264-266.

Coleman "Diabetes-obesity syndromes in mice," *Diabetes* (1982) 31(Suppl 1):1-6.

Coleman et al., "Fat (fat) and tubby (tub): two autosomal recessive mutations causing obesity syndromes in the mouse," *J. Heredity* (1990) 81:424-427.

Cornhill et al., "Topographic study of sudanophilic lesions in cholesterol-fed minipigs by image analysis," *Arteriosclerosis, Thrombosis and Vascular Biology* (1985) 5(5):415-426.

Delporte et al., "Pre- and post-translational negative effect of beta-adrenoceptor agonists on adiponectin secretion: in vitro and in vivo studies," *Biochem Journal* (2002) 367:677-85.

Erikkson et al., "Increased incidence of congenital malformations in the offspring of diabetic rats and their prevention by maternal insulin therapy," *Diabetes* (1982) 31:1-6.

Friedman et al., "Tackling a weighty problem," *Cell* (1992) 69:217-220.

Gerrity et al., "Diabetes-induced accelerated atherosclerosis in swine," *Diabetes* (2001) 50(7):1654-1665.

Guyton "Effect of niacin on atherosclerotic cardiovascular disease," *Am. J. Cardiol.* (1998) 82:18U-23U.

Koranyi et al., "Glucose transporter levels in spontaneously obese (db/db) insulin-resistant mice," *J. Clin Invest* (1990) 85:962-967.

Lorenzen et al., "Characterization of a G protein-coupled receptor for nicotinic acid," *Molecular Pharmacology* (2001) 59(2):349-357.

Lorenzen et al., "G protein-coupled receptor for nicotinic acid in mouse macrophages," *Biochemical Pharmacology* (2002) 64:645-648.

Matsuda et al., "Role of adiponectin in preventing vascular stenosis. The missing link of adipo-vascular axis," *J. Biol. Chem.* (2002) 277(40):37487-91.

Royo et al., "Effect of gemfibrozil on peripheral atherosclerosis and platelet activation in a pig model of hyperlipidemia," *Eur J Clin Invest.* (2000) 30(10):843-52.

Truett et al., "Rat obesity gene fatty (*fa*) maps to chromosome 5: evidence for homology with the mouse gene diabetes (db)," *Proc. Natl. Acad. Sci. USA* (1991) 88(17):7806-7809.

Zhu, et al., "Synthesis and mode of action of (125)I- and (3)H-labeled thieno[2,3-c]pyridine antagonists of cell adhesion molecule expression," *J. Org. Chem.* (2002) 67:943-948.

Goodman and Gilman's Pharmacological Basis of Therapeutics, editors Harmon JG and Limbird LE, Chapter 36, Mahley RW and Bersot TP (2001) pp. 971-1002.

Hudlicky, *Oxidations in Organic Chemistry, ACS Monograph 186* (1990).

Merck Index, An Encyclopedia of Chemicals, Drugs, and Biologicals, Tenth Edition (1983).

(56) References Cited

OTHER PUBLICATIONS

Smith et al., *Advanced Organic Chemistry* (2001) 5th Edition, Wiley-Interscience.

Larock, *Comprehensive Organic Transformations, A Guide to Functional Group Preparations*, 2nd Edition, VCH Publishers, Inc. (1999).

Wuts et al., *Protective Groups in Organic Synthesis*, 3rd Edition, John Wiley and Sons (1999).

Jacques et al., *Enantiomers, Racemates and Resolutions* (1981) John Wiley and Sons, New York.

Remington, *The Science and Practice of Pharmacy* (2000) 20th Edition, Lippincott Williams & Wilkins (Editors: Gennaro et al.).

Higuchi et al., "Pro-drugs as novel delivery systems," vol. 14 of the A.C.S. Symposium Series, Oct. 4, 2010.

Bioreversible Carriers in Drug Design, ed. Edward B. Roche, American Pharmaceutical Association and Pergamon Press (1987).

Shafrir "Diabetes in Animals," *Diabetes Mellitus*, Rifkin et al., Eds [Elsevier Science Publishing Co., New York, ed. 4, (1990) pp. 299-340.]

Horikoshi et al., "Troglitazone (CS-045), a new Antidiabetic Drug," *Annu Rep Sankyo Res Lab* (1994) 46:1-57.

ElAmin et al., "Removal of benzyl-type protecting groups from peptides by catalytic transfer hydrogenation with formic acid," *J Org Chem* (1979) 44(19):3442-3444.

Flechtner-Mors et al., "Effects of acipimox on the lipolysis rate in subcutaneous adipose tissue of obese subjects," *Diabetes/Metabolism Research and Reviews* (2001) 17:387-390.

Haddach et al., "An efficient method for the N-debenzylation of aromatic heterocycles," *Tetrahedron Letters* (2002) 43:399-402.

van Herk et al., "Pyrazole derivatives as partial agonists for the nicotinic acid receptor," *J Med Chem* (2003) 46:3945-3951.

Holland et al., "Heterocyclic tetrazoles, a new class of lipolysis inhibitors," *Journal of Medicinal Chemistry* (1967) 10:149-154.

Krynitsky et al., "2-Ethylhexanonitrile," *Organic Syntheses, Coll.* (1963) 4:436.

Soga et al., "Molecular identification of nicotinic acid receptor," *Biochemical and Biophysical Research Communications* (2003) 303:364-369.

Surrey "Malononitrile," *Organic Syntheses, Coll.* (1955) 3:535.

Tunaru et al., "PUMA-G and HM74 are receptors for nicotinic acid and mediate its anti-lipolytic effect," *Nature Medicine* (published online Feb. 3, 2003) 1-4.

Wise et al., "Molecular identification of high and low affinity receptors for nicotinic acid," *The Journal of Biological Chemistry* (2003) 278(11):9869-9874.

Alterman, M. et al., "Fast microwave-assisted preparation of aryl and vinyl nitriles and the corresponding tetrazoles from organo-halides", J. Org. Chem. 65:7984-89 (2000).

Cahn, R.S. et al., "Specification of molecular chirality", Angew. Chem. Internat. Edit. 5(4):385-415 (1966).

Carballo-Jane et al., "Comparison of rat and dog models of vasodilation and lipolysis for the calculation of a therapeutic index for GPR109A agonists," *Journal of Pharmacological and Toxicological Methods*, Article in Press, doi:10.1016/j.vascn.2007.05.007 (2007).

Carballo-Jane et al., "Comparison of rat and dog models of vasodilation and lipolysis for the calculation of a therapeutic index for GPR109A agonists," *Journal of Pharmacological and Toxicological Methods*, 56(3). pp. 308-316, (2007).

Clayton, S. et al., "A total synthesis of (±)-epibatidine", Tetrahedron Letters 34(46):7493-6 (1993).

Cohen, T. et al., "Synthetically useful β-lithioalkoxides from reductive lithiation of epoxides by aromatic radical anions", J. Org. Chem. 55:1528-36 (1990).

Corsaro, A. et al., "Steric course of some cyclopropanation reactions of L-threo-hex-4-enopyranosides", Tetrahedron Letters 60:3787-95 (2004).

Effenberger, F. et al., "Regioselective halo- and carbodesilylation of (trimethylsilyl)-1-methylpyrazoles", J. Org. Chem. 49:4687-95 (1984).

Gharbaoui et al., "Agonist lead identification for the high affinity niacin receptor GPR109a ," Bioorganic & Medicinal Chemistry Letters, 17:4914-4919 (2007).

Hodgson, D. et al., "Intramolecular cyclopropanation of unsaturated terminal epoxides", J. Am. Chem. Soc. 126:8664-5 (2004).

Hodgson, D. et al., J. Am. Chem. Soc. 126:8664 (2004)(supporting information).

Jung et al., "Analogues of acifran: agonists of the high and low affinity niacin receptors, GPR109a and GPR109b," *Journal of Medicinal Chemistry*, 50:1445-1448 (2007).

Katritzky, A. et al., "Alpha-lithiation of N-alkyl groups in pyrazoles", Tetrahedron Letters 39:2023-9 (1983).

Latli, B. et al., "Novel and potent 6-chloro-3-pyridinyl ligands for the α4β2 neuronal nicotinic acetylcholine receptor", J. Med. Chem. 42:2227-34 (1999).

Latli, B. et al., Supporting information for "Novel and potent 6-chloro-3-pyridinyl ligands for the α4β2 neuronal nicotinic acetylcholine receptor", J. Med. Chem. pp. 2227(1999).

Maciejewski-Lenoir et al., "Langerhans cells release prostaglandin $D_2$ in response to nicotinic acid," *Journal of Investigative Dermatology*, 126:2637-2646 (2006).

Mahley, R. et al., "Drug therapy for hypercholesterolemia and dyslipidemia", Goodman & Gilman 36:971-1002 (2004).

Mariano, P. et al., "Mechanistic aspcts of gas-phase photodecarbonylation reactions of bicycle[3.1.0]hexanones", J. Org. Chem. 45:1753-62 (1980).

Miller, R.D. et al., "Deoxygenation of sulfoxides promoted by electrophilic silicon reagents: preparation of aryl-substituted sulfonium salts", J. Org. Chem. 53:5571-3 (1988).

Movassaghi, M. et al., "A direct method for the conversion of terminal epoxides into γ-butanolides", J. Am. Chem. Soc. 124(11):2456-7 (2002).

Newman-Evans, R. et al., "The influence of intramolecular dynamics on branching ratios in thermal rearrangements", J. Org. Chem. 55:695-711 (1990).

Nishimura, J. et al., "A novel synthesis of methylcyclopropanes", Tetrahedron Letters 25:2647-59 (1969).

Olivo, H. et al., "Synthetic studies on the trans-Chlorocyclopropane dienyne side chain of Callipeltoside-A", Org. Lett. 2(25):4055-8 (2000).

Prelog, V. et al., "Basic principles of the CIP-system and proposals for a revision", Angew. Chem. Int. Ed. Engl. 21:567-83 (1982).

Richman et al., "Nicotinic acid receptor agonists differentially activate downstream effectors," *The Journal of Biological Chemistry*, 282:18028-18036, (2007).

Schaus, S. et al., "Highly selective hydrolytic kinetic resolution of terminal epoxides catalyzed by chiral (salen)cobalt(III)-complexes. Practical synthesis of enantioenriched terminal epoxides and 1,2-Diols", JACS 124:1307 (2002).

Semple et al., "Recent progress in the discovery of niacin receptor agonists," *Current Opinion in Drug Discovery & Development*, 10:452-459, (2007).

Semple et al., "1-Alkyl-benzotriazole-5-carboxylic acids are highly selective agonists of the human orphan G-protein-coupled receptor GPR109b," *Journal of Medicinal Chemistry* 49:1227-1230, (2006).

Semple, "Niacin receptor agonists," *Presentation*, American Chemical Society 233rd National Meeting & Exposition, Mar. 25, 2007-Mar. 29, 2007, Chicago, Illinois.

Semple, "Discovery of selective agonists for GPR109a and GPR109b, the high and low affinity receptors for niacin," *Presentation, GPCRs in Medicinal Chemistry*, jointly organized by the Society of Chemical Industry, Royal Society of Chemistry and the Societa Chimica Italiana, Sep. 18, 2006-Sep. 20, 2006, Verona, Italy.

Skinner et al, "Fluorinated pyrazole acids are agonists of the high affinity niacin receptor GPRI09a," *Poster*, 30th National Medicinal Chemistry Symposium, Jun. 25, 2006-Jun. 29, 2006, Seattle, WA.

(56) References Cited

OTHER PUBLICATIONS

Smith, A. et al, Total synthesis of the neotropical poison-frog alkaloid (−)-205B, Org. Lett. 7(15):3247-50 (2005).

Taber, D. et al., "Synthesis of the eight enantiomerically pure diastereomers of the 12-F2-Isoprostanes", J. Am. Chem. Soc. 124:13121-6 (2002).

Taggart et al., "(D)-β-Hydroxybutyrate inhibits adipocyte lipolysis via the nicotinic acid receptor PUMA-G," *The Journal of Biological Chemistry*, 280:26649-26652, (2005).

Turner, S. et al., "Enantiospecific synthesis of annulated nicotine analogues from D- and L-glutamic acid Pyridotropanes", J. Org. Chem. 65:861-70 (2000).

Yagi, H. et al., "Removal of benzyl-type protecting groups frompeptides by catalytic transfer hydrogenation with formic acid", J. Org. Chem. 44(19):3442-4 (1979).

Zhang, R. et al., "Cyclopropanation reactions of pyroglutamic acid-derived synthons with akylidene transfer reagents", J. Org. Chem. 64:547-55 (1999).

\* cited by examiner

TETRAZOLE DERIVATIVES AND METHODS OF TREATMENT OF METABOLIC-RELATED DISORDERS THEREOF

CROSS REFERENCE TO RELATED APPLICATIONS

This application is a 35 U.S.C. §371 National Stage Application of International Application No. PCT/US2004/35927, filed Oct. 29, 2004, which claims priority to U.S. Ser. No. 60/516,238, filed Oct. 31, 2003.

FIELD OF THE INVENTION

The present invention relates to certain tetrazole derivatives, and pharmaceutically acceptable salts thereof, which exhibit useful pharmacological properties, for example as agonists for the nicotinic acid receptor, RUP25. Also provided by the present invention are pharmaceutical compositions containing one or more compounds of the invention, and methods of using the compounds and compositions of the invention in the treatment of metabolic-related disorders, including dyslipidemia, atherosclerosis, coronary heart disease, insulin resistance, type 2 diabetes, Syndrome-X and the like. In addition, the present invention also provides for the use of the compounds of the invention in combination with other active agents such as those belonging to the class of α-glucosidase inhibitors, aldose reductase inhibitors, biguanides, HMG-CoA reductase inhibitors, squalene synthesis inhibitors, fibrates, LDL catabolism enhancers, angiotensin converting enzyme (ACE) inhibitors, insulin secretion enhancers, thiazolidinedione and the like.

BACKGROUND OF THE INVENTION

Compounds of the Invention as Antilipolytic Agents

Atherosclerosis and stroke are the numbers one and number three leading causes of death of both men and women in the United States. Type 2 diabetes is a public health problem that is serious, widespread and increasing. Elevated levels of low density lipoprotein (LDL) cholesterol or low levels of high density lipoprotein (HDL) cholesterol are, independently, risk factors for atherosclerosis and associated cardiovascular pathologies. In addition, high levels of plasma free fatty acids are associated with insulin resistance and type 2 diabetes. One strategy for decreasing LDL-cholesterol, increasing HDL-cholesterol, and decreasing plasma free fatty acids is to inhibit lipolysis in adipose tissue. This approach involves regulation of hormone sensitive lipase, which is the rate-limiting enzyme in lipolysis. Lipolytic agents increase cellular levels of cAMP, which leads to activation of hormone sensitive lipase within adipocytes. Agents that lower intracellular cAMP levels, by contrast, would be antilipolytic.

It is also worth noting in passing that an increase in cellular levels of cAMP down-regulates the secretion of adiponectin from adipocytes [Delporte, M L et al. *Biochem J* (2002) July]. Reduced levels of plasma adiponectin have been associated with metabolic-related disorders, including atherosclerosis, coronary heart disease, insulin resistance and type 2 diabetes [Matsuda, M et al. J Biol Chem (2002) July and reviewed therein].

Nicotinic acid (niacin, pyridine-3-carboxylic acid) is a water-soluble vitamin required by the human body for health, growth and reproduction; a part of the Vitamin B complex. Nicotinic acid is also one of the oldest used drugs for the treatment of dyslipidemia. It is a valuable drug in that it favorably affects virtually all of the lipid parameters listed above [Goodman and Gilman's Pharmacological Basis of Therapeutics, editors Harmon J G and Limbird L E, Chapter 36, Mahley R W and Bersot T P (2001) pages 971-1002]. The benefits of nicotinic acid in the treatment or prevention of atherosclerotic cardiovascular disease have been documented in six major clinical trials [Guyton J R (1998) Am J Cardiol 82:18U-23U]. Nicotinic acid and related derivatives, such as, acipimox have recently been discussed [Lorenzen, A et al (2001) Molecular Pharmacology 59:349-357]. Structure and synthesis of additional analogs or derivatives of nicotinic acid are discussed throughout the Merck Index, An Encyclopedia of Chemicals, Drugs, and Biologicals, Tenth Edition (1983), which is incorporated herein by reference in its entirety.

Nicotinic acid inhibits the production and release of free fatty acids from adipose tissue, likely via an inhibition of adenylyl cyclase, a decrease in intracellular cAMP levels, and a concomitant decrease in hormone sensitive lipase activity. Agonists that down-regulate hormone sensitive lipase activity leading to a decrease in plasma free fatty acid levels are likely to have therapeutic value. The consequence of decreasing plasma free fatty acids is two-fold. First, it will ultimately lower LDL-cholesterol and raise HDL-cholesterol levels, independent risk factors, thereby reducing the risk of mortality due to cardiovascular incidence subsequent to atheroma formation. Second, it will provide an increase in insulin sensitivity in individuals with insulin resistance or type 2 diabetes. Unfortunately, the use of nicotinic acid as a therapeutic is partially limited by a number of associated, adverse side-effects. These include flushing, free fatty acid rebound, and liver toxicity.

The rational development of novel, nicotinic acid receptor agonists that have fewer side-effects will be valuable, but to date this has been hindered by the inability to molecularly identify the nicotinic acid receptor. Furthermore, other receptors of the same class may exist on the surface of adipocytes and similarly decrease hormone sensitive lipase activity through a reduction in the level of intracellular cAMP but without the elicitation of adverse effects such as flushing, thereby representing promising novel therapeutic targets. Recent work suggests that nicotinic acid probably acts through a specific GPCR [Lorenzen A, et al. (2001) Molecular Pharmacology 59:349-357 and reviewed therein]. Further work has suggested that the effects of nicotinic acid on macrophages, spleen and probably adipocytes are mediated via this specific GPCR [Lorenzen A, et al. (2002) Biochemical Pharmacology 64:645-648 and reviewed therein].

SUMMARY OF THE INVENTION

One aspect of the present invention encompasses tetrazole derivatives as shown in Formula (I):

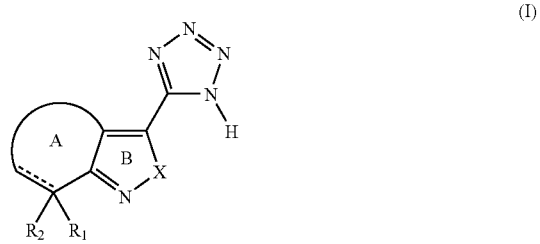

(I)

wherein:
X is NH or O;
$R_1$ is selected from the group consisting of H, halogen, hydroxy, thioxy, cyano, nitro, $C_{1-4}$ haloalkyl, amino, $C_{1-4}$ alkylamino, $C_{2-8}$ dialkylamino, $C_{1-4}$ alkyl, $C_{1-4}$ alkoxy, $C_{2-4}$ alkenyl, $C_{2-4}$ alkynyl, $C_{3-5}$ cycloalkyl, $C_{1-4}$ haloalkoxy, $C_{1-4}$ alkylthio, $C_{1-4}$ alkylsulfonyl, $C_{1-4}$ alkylsulfonyl, $C_{1-4}$ haloalkylthio, $C_{1-4}$ haloalkylsulfinyl and $C_{1-4}$ haloalkylsulfonyl;

$R_2$ is selected from the group consisting of H, halogen, hydroxy, thioxy, cyano, nitro, $C_{1-4}$ haloalkyl, amino, $C_{1-4}$ alkylamino, $C_{2-8}$ dialkylamino, $C_{1-4}$ alkyl, $C_{1-4}$ alkoxy, $C_{2-4}$ alkenyl, $C_{2-4}$ alkynyl, $C_{3-5}$ cycloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl and $C_{1-4}$ haloalkylsulfonyl; or $R_2$ is absent;

----- is a single bond when $R_2$ is present, or ----- is a double bond when $R_2$ is absent; and Ring A is a 5, 6 or 7-membered carbocyclic ring or a 5, 6 or 7-membered heterocyclic ring optionally substituted with 1 to 4 substituents selected from the group consisting of halogen, hydroxy, thioxy, cyano, nitro, $C_{1-4}$ haloalkyl, amino, $C_{1-4}$ alkylamino, $C_{2-8}$ dialkylamino, $C_{1-4}$ alkyl, $C_{1-4}$ alkoxy, $C_{2-4}$ alkenyl, $C_{2-4}$ alkynyl, $C_{3-5}$ cycloalkyl, $C_{1-4}$ haloalkoxy, $C_{1-4}$ alkylthio, $C_{1-4}$ alkylsulfonyl, $C_{1-4}$ alkylsulfonyl, $C_{1-4}$ haloalkylthio, $C_{1-4}$ haloalkylsulfinyl and $C_{1-4}$ haloalkylsulfonyl; or a pharmaceutically acceptable salt, solvate or hydrate thereof.

One aspect of the present invention encompasses pharmaceutical compositions comprising at least one compound according to Formula (I), as described herein.

In some embodiments, the pharmaceutical composition further comprises one or more agents selected from the group consisting of αglucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

One aspect of the present invention pertains to methods of treatment of a metabolic-related disorder comprising administering to an individual in need of such treatment a therapeutically-effective amount of a compound according to Formula (I), as described herein, or a pharmaceutical composition thereof.

One aspect of the present invention pertains to methods of modulating a RUP25 receptor comprising contacting the receptor with a compound according to Formula (I), as described herein.

One aspect of the present invention pertains to methods of modulating a RUP25 receptor for the treatment of a metabolic-related disorder in an individual in need of such modulation comprising contacting said receptor with a therapeutically-effective amount of a compound according to Formula (I), as described herein.

One aspect of the present invention pertains to methods of raising HDL in an individual comprising administering to the individual a therapeutically-effective amount of a compound according to Formula (I), as described herein.

One aspect of the present invention pertains to a compound of Formula (I), as described herein, for use in a method of treatment of the human or animal body by therapy.

One aspect of the present invention pertains to a compound of Formula (I), as described herein, for use in a method of treatment of a metabolic-related disorder of the human or animal body by therapy.

One aspect of the present invention pertains to the use of compounds of Formula (I), as described herein, for the manufacture of a medicament for use in the treatment of a metabolic-related disorder.

In some embodiments of the present invention, the metabolic-related disorder is of the group consisting of dyslipidemia, atherosclerosis, coronary heart disease, insulin resistance, obesity, impaired glucose tolerance, atheromatous disease, hypertension, stroke, Syndrome X, heart disease and type 2 diabetes. In some embodiments the metabolic-related disorder is dyslipidemia, atherosclerosis, coronary heart disease, insulin resistance and type 2 diabetes. In some embodiments the metabolic-related disorder is dyslipidemia. In some embodiments the metabolic-related disorder is atherosclerosis. In some embodiments the metabolic-related disorder is coronary heart disease. In some embodiments the metabolic-related disorder is insulin resistance. In some embodiments the metabolic-related disorder is type 2 diabetes.

One aspect of the present invention encompasses a method of producing a pharmaceutical composition comprising admixing at least one compound according to Formula (I), as described herein, and a pharmaceutically acceptable carrier or excipient.

These and other aspects of the invention disclosed herein will be set forth in greater detail as the patent disclosure proceeds.

DETAILED DESCRIPTION OF THE INVENTION

The scientific literature has adopted a number of terms, for consistency and clarity, the following definitions will be used throughout this patent document.

AGONISTS shall mean moieties that interact and activate the receptor, such as the RUP25 receptor and initiates a physiological or pharmacological response characteristic of that receptor. For example, when moieties activate the intracellular response upon binding to the receptor, or enhance GTP binding to membranes.

TABLE 1

AMINO ACID ABBREVIATIONS used herein are set out in TABLE 1:

| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

The term ANTAGONISTS is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

ATHEROSCLEROSIS is intended herein to encompass disorders of large and medium-sized arteries that result in the progressive accumulation within the intima of smooth muscle cells and lipids.

Chemical Group, Moiety or Radical:

The term "$C_{1-4}$ acyl" denotes a $C_{1-4}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-4}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{2-4}$ alkenyl" denotes a radical containing 2 to 4 carbons wherein at least one carbon-carbon double bond is present, some embodiments are 2 to 3 carbons, and some embodiments have 2 carbons. Both E and Z isomers are embraced by the term "alkenyl." Furthermore, the term "alkenyl" includes di-enes. Accordingly, if more than one double bond is present, then the bonds may be all E or Z or a mixtures of E and Z. Examples of an alkenyl include vinyl, propenyl, allyl, isopropenyl, 2-methyl-propenyl 1-methyl-propenyl, but-1-enyl, but-2-enyl, but-3-enyl, buta-1,3-dienyl, and the like.

The term "$C_{1-4}$ alkoxy" denotes an alkyl radical, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-4}$ alkyl" denotes a straight or branched carbon radical containing the number of carbons as indicated, for examples, in some embodiments, alkyl is a "$C_{1-4}$ alkyl" and the group contains 1 to 4 carbons. In some embodiments alkyl contains 1 to 13 carbons, some embodiments contain 1 to 2 carbons, some embodiments contain 1 carbon. Examples of an alkyl include, but not limited to, methyl, ethyl, n-propyl, iso-propyl, n-butyl, iso-butyl, t-butyl, sec-butyl, and the like.

The term "$C_{1-4}$ alkylsulfinyl" denotes a $C_{1-4}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-4}$ alkylsulfonyl" denotes a $C_{1-4}$ alkyl radical attached to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-4}$ alkylthio" denotes a $C_{1-4}$ alkyl radical attached to a sulfide group of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{2-4}$ alkynyl" denotes a radical containing 2 to 4 carbons and at least one carbon-carbon triple bond, some embodiments are 2 to 3 carbons, and some embodiments have 2 carbons. Examples of an alkynyl include, but not limited to, ethynyl, prop-1-ynyl, 3-prop-2-ynyl, but-1-ynyl, 1-methyl-prop-2-ynyl, buta-1,3-diynyl, and the like. The term "alkynyl" includes di-ynes.

The term "amino" denotes the group —NH$_2$.

The term "$C_{1-4}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "carbo-$C_{1-4}$-alkoxy" denotes a $C_{1-4}$ alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, and the like.

The term "carboxamide" refers to the group —CONH$_2$.

The term "carboxy" or "carboxyl" denotes the group —CO$_2$H; also referred to as a carboxylic acid group.

The term "cyano" denotes the group —CN.

The term "$C_{3-5}$ cycloalkyl" denotes a saturated ring radical containing 3 to 6 carbons; some embodiments contain 3 to 5 carbons; some embodiments contain 3 to 4 carbons. Examples include, cyclopropyl, cyclobutyl, cyclopentyl, cyclohexyl.

The term "$C_{2-8}$ dialkylamino" denotes an amino substituted with two of the same or different alkyl radicals wherein alkyl radical has the same definition as described herein. A $C_{2-8}$ dialkylamino may be represented by the following groups:

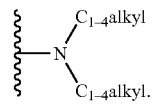

Examples of $C_{2-8}$ dialkylamino include, but not limited to, dimethylamino, methylethylamino, diethylamino, methylpropylamino, methylisopropylamino, and the like.

The term "$C_{1-4}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy and the like.

The term "$C_{1-4}$ haloalkyl" denotes an alkyl group wherein the alkyl is substituted with halogen ranging from one to fully substituted, wherein a fully substituted haloalkyl can be represented by the formula $C_hL_{2h+1}$ wherein L is a halogen and "h" represents the number of carbon atoms; when more than one halogen is present then the halogens may be the same or different and selected from the group consisting of F, Cl, Br and I; it is understood that the terms "alkyl" and "halogen" have the same definition as found herein. In some embodiments, haloalkyl is a "$C_{1-4}$ haloalkyl" and the group contains 1 to 4 carbons, some embodiments contain 1 to 3 carbons, some embodiments contain 1 to 2 carbons, some embodiments contain 1 carbon. When the haloalkyl is fully substituted with halogen atoms, this group is referred herein as a perhaloalkyl, one example, is an alkyl fully substituted with fluorine atoms and is referred to herein as a "perfluoroalkyl." In some embodiments, examples of a haloalkyl include, but not limited to, difluoromethyl, fluoromethyl, 2,2,2-trifluoro-ethyl, 2,2-difluoro-ethyl, 2-fluoro-ethyl, 1,2,2-trifluoro-ethyl, 1,2-difluoro-ethyl, 1,1-difluoro-ethyl, 1,1,2-trifluoro-ethyl, 3,3,3-trifluoro-propyl, 2,2-difluoro-propyl, 3,3-difluoro-propyl, 3-fluoro-propyl, 2,3,3-trifluoro-propyl, 2,3-Difluoro-propyl, 2,2,3,3,3-pentafluoro-propyl, 2,2,3,3-tetrafluoro-propyl, 2,2,3-trifluoro-propyl, 1,2,3,3-tetrafluoro-propyl, 1,2,3-trifluoro-propyl, 3,3-difluoropropyl, 1,2,2,3-tetrafluoro-propyl, 4,4-difluoro-butyl, 3,3-difluoro-butyl, 4,4,4-trifluoro-butyl, 3,3-difluoro-butyl, and the like. In some embodiments, examples of a perfluoroalkyl include, but not limited to, trifluoromethyl, pentafluoroethyl, heptafluoropropyl, 1,2,2,2-tetrafluoro-1-trifluoromethyl-ethyl, and the like.

The term "$C_{1-4}$ haloalkylsulfinyl" denotes a haloalkyl radical attached to a sulfoxide group of the formula: —S(O)— wherein the haloalkyl radical has the same definition as described herein.

The term "$C_{1-4}$ haloalkylsulfonyl" denotes a haloalkyl radical attached to a sulfone group of the formula: —S(O)$_2$— wherein haloalkyl has the same definition as described herein.

The term "$C_{1-4}$ haloalkylthio" denotes a haloalkyl radical directly attached to a sulfur atom wherein the haloalkyl has the same meaning as described herein.

The term "halogen" or "halo" denotes to a fluoro, chloro, bromo or iodo group.

The term "hydroxyl" denotes the group —OH.
The term "nitro" denotes the group —NO$_2$.
The term "thioxy" denotes the group —SH.
The acronym DMF denotes dimethylformamide.
The acronym DMSO denotes dimethylsulfoxide.
The acronym THF denotes tetrahydrofuran.
The acronym DCM denotes dichloromethane.
The acronym Hex denotes hexanes.
The acronym TBDMS denotes tert-butyldimethylsilyl.
The acronym PTSA denotes para-toluenesulfonic acid.
The acronym LDA denotes lithium diisopropylamide.
The acronym LHMDS denotes lithium hexamethyldisilazane.
The acronym TFA denotes trifluoroacetic acid.
The acronym EDC denotes 1-ethyl-3-(3-dimethylaminopropyl)carbodiimide hydrochloride.
The acronym dppf denotes 1,1'-bis(diphenylphosphino) ferrocene.

The term CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

The term COMPOSITION shall mean a material comprising at least two compounds or two components; for example, and without limitation, a Pharmaceutical Composition is a Composition comprising a compound of the present invention and a pharmaceutically acceptable carrier.

The term COMPOUND EFFICACY shall mean a measurement of the ability of a compound to inhibit or stimulate receptor functionality, as opposed to receptor binding affinity.

The term CONSTITUTIVELY ACTIVATED RECEPTOR shall mean a receptor subject to constitutive receptor activation.

The term CONSTITUTIVE RECEPTOR ACTIVATION shall mean stabilization of a receptor in the active state by means other than binding of the receptor with its endogenous ligand or a chemical equivalent thereof.

The terms CONTACT or CONTACTING shall mean bringing the indicated moieties together, whether in an in vitro system or an in vivo system. Thus, "contacting" a RUP25 receptor with a compound of the invention includes the administration of a compound of the present invention to an individual, for example a human, having a RUP25 receptor, as well as, for example, introducing a compound of the invention into a sample containing a cellular or more purified preparation containing a RUP25 receptor.

CORONARY HEART DISEASE is intended herein to encompass disorders comprising a narrowing of the small blood vessels that supply blood and oxygen to the heart. Coronary heart disease usually results from the build up of fatty material and plaque. As the coronary arteries narrow, the flow of blood to the heart can slow or stop. Coronary heart disease can cause chest pain (stable angina), shortness of breath, heart attack, or other symptoms.

DECREASE is used to refer to a reduction in a measurable quantity and is used synonymously with the terms "reduce", "diminish", "lower", and "lessen".

DIABETES as used herein is intended to encompass the usual diagnosis of DIABETES made from any of the methods including, but not limited to, the following list: symptoms of diabetes (e.g., polyuria, polydipsia, polyphagia) plus casual plasma glucose levels of greater than or equal to 200 mg/dl, wherein casual plasma glucose is defined any time of the day regardless of the timing of meal or drink consumption; 8 hour fasting plasma glucose levels of less than or equal to 126 mg/dl; and plasma glucose levels of greater than or equal to 200 mg/dl 2 hours following oral administration of 75 g anhydrous glucose dissolved in water.

The phrase DISORDERS OF LIPID METABOLISM is intended herein to include, but not be limited to, dyslipidemia.

The term DYSLIPIDEMIA is intended herein to encompass disorders comprising any one of elevated level of plasma free fatty acids, elevated level of plasma cholesterol, elevated level of LDL-cholesterol, reduced level of HDL-cholesterol, and elevated level of plasma triglycerides.

The phrase IN NEED OF TREATMENT, as used herein, refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, that includes the knowledge that the individual is ill, or will be ill, as the result of a disease, condition or disorder that is treatable by the compounds of the invention. Further, the phrase "in need of treatment" also refers to the "prophylaxis" of an individual which is the judgment made by the caregiver that the individual will become ill. In this context, the compounds of the invention are used in a protective or preventive manner. Accordingly, "in need of treatment" refers to the judgment of the caregiver that the individual is already ill or will become ill and the compounds of the present invention can be used to alleviate, inhibit, ameliorate or prevent the disease, condition or disorder.

The term INDIVIDUAL as used herein refers to any animal, including mammals, for example, mice, rats, other rodents, rabbits, dogs, cats, swine, cattle, sheep, horses, or primates, and in one embodiment, humans.

The terms INHIBIT or INHIBITING, in relationship to the term "response" shall mean that a response is decreased or prevented in the presence of a compound as opposed to in the absence of the compound.

INSULIN RESISTANCE as used herein is intended to encompass the usual diagnosis of insulin resistance made by any of a number of methods, including but not restricted to: the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

The term INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. In some embodiments, the baseline intracellular response is inhibited in the presence of the inverse agonist by at least 30%, in other embodiments, by at least 50%, and in still other embodiments, by at least 75%, as compared with the baseline response in the absence of the inverse agonist.

The term LIGAND shall mean an endogenous, naturally occurring molecule specific for an endogenous, naturally occurring receptor.

The phrase METABOLIC-RELATED DISORDERS is intended herein to include, but not be limited to, dyslipidemia, atherosclerosis, coronary heart disease, insulin resistance, obesity, impaired glucose tolerance, atheromatous disease, hypertension, stroke, Syndrome X, heart disease and type 2 diabetes.

As used herein, the terms MODULATE or MODULATING shall mean to refer to an increase or decrease in the amount, quality, response or effect of a particular activity, function or molecule.

The term PHARMACEUTICAL COMPOSITION shall mean a composition for preventing, treating or controlling a disease state or condition comprising at least one active compound, for example, a compound of the present invention including pharmaceutically acceptable salts, pharmaceutically acceptable solvates and/or hydrates thereof, and at least one pharmaceutically acceptable carrier.

The term PHARMACEUTICALLY ACCEPTABLE CARRIER or EXCIPIENT shall mean any substantially inert substance substance used as a diluent or vehicle for a compound of the present invention.

The phrase THERAPEUTICALLY-EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Invention

One aspect of the present invention encompasses tetrazole derivatives as shown in Formula (I):

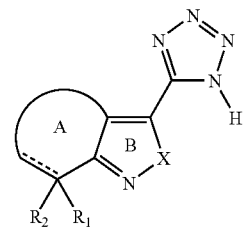

wherein:

X is NH or O;

$R_1$ is selected from the group consisting of H, halogen, hydroxy, thioxy, cyano, nitro, $C_{1-4}$ haloalkyl, amino, $C_{1-4}$ alkylamino, $C_{2-8}$ dialkylamino, $C_{1-4}$ alkyl, $C_{1-4}$ alkoxy, $C_{2-4}$ alkenyl, $C_{2-4}$ alkynyl, $C_{3-5}$ cycloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl and $C_{1-4}$ haloalkylsulfonyl;

$R_2$ is selected from the group consisting of H, halogen, hydroxy, thioxy, cyano, nitro, $C_{1-4}$ haloalkyl, amino, $C_{1-4}$ alkylamino, $C_{2-8}$ dialkylamino, $C_{1-4}$ alkyl, $C_{1-4}$ alkoxy, $C_{2-4}$ alkenyl, $C_{2-4}$ alkynyl, $C_{3-5}$ cycloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl and $C_{1-4}$ haloalkylsulfonyl; or $R_2$ is absent;

===== is a single bond when $R_2$ is present, or ===== is a double bond when $R_2$ is absent; and Ring A is a 5, 6 or 7-membered carbocyclic ring or a 5, 6 or 7-membered heterocyclic ring optionally substituted with 1 to 4 substituents selected from the group consisting of halogen, hydroxy, thioxy, cyano, nitro, $C_{1-4}$ haloalkyl, amino, $C_{1-4}$ alkylamino, $C_{2-8}$ dialkylamino, $C_{1-4}$ alkyl, $C_{1-4}$ alkoxy, $C_{2-4}$ alkenyl, $C_{2-4}$ alkynyl, $C_{3-5}$ cycloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl and $C_{1-4}$ haloalkylsulfonyl; or a pharmaceutically acceptable salt, solvate or hydrate thereof.

Compounds of the present invention may exist in various tautomeric forms. For example, it is well appreciated to those of skill in the art that tetrazoles can exist in at least two tautomeric forms and although Formula (I) represents one form it is understood that all tautomeric forms are embraced by the present invention; by way of illustration, two possible tautomers for the tetrazole in Formula (I) are shown below:

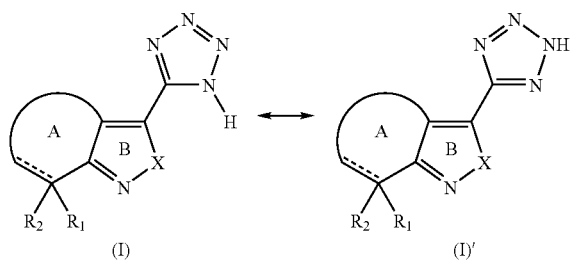

Another example includes embodiments wherein X is NH. It is well appreciated to those of skill in the art that pyrazole heterocycles can exist in at least two tautomeric forms and although Formula (I) represents one form it is understood that all tautomeric forms are embraced by the present invention;

by way of illustration, two possible tautomers for the pyrazole wherein X is NH in Formula (I) are shown below:

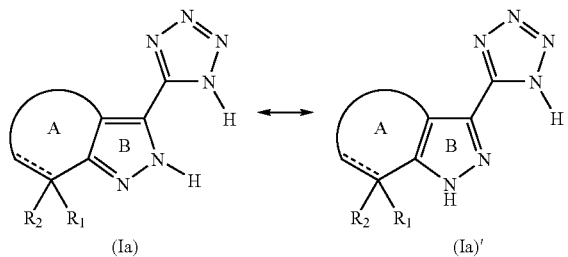

(Ia)    (Ia)'

Further, it is understood that when X is NH then tautomers can exist for both Ring B and also the tetrazole ring in combination. It is understood that all tautomers that can exist for the compounds disclosed herein are within the scope of the invention.

The present invention also encompasses diastereomers as well as optical isomers, e.g. mixtures of enantiomers including racemic mixtures, as well as individual enantiomers and diastereomers, which arise as a consequence of structural asymmetry in certain compounds of the present invention. In some embodiments, compounds of the present invention are R. In some embodiments, compounds of the present are S. In some embodiments, compounds of the present invention are racemic mixtures.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, "substituted" indicates that at least one hydrogen atom of the chemical group is replaced by a non-hydrogen substituents or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, and the like.

One embodiment of the present invention pertains to compounds of Formula (I) wherein X is NH. This embodiment can be represented by Formula (Ia) as illustrated below:

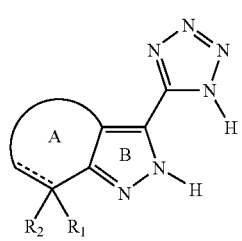

(Ia)

wherein each variable in Formula (Ia) has the same meaning as described herein, supra and infra.

One embodiment of the present invention pertains to compound of Formula (I) wherein X is NH, $R_1$ is H or hydroxy; $R_2$ is H or absent; ----- is a single bond when $R_2$ is H, or ----- is a double bond when $R_2$ is absent; and Ring A is a 5-membered carbocyclic ring or a 5-membered heterocyclic ring optionally substituted with 1 to 4 substituents selected from the group consisting of halogen, $C_{1-4}$ alkyl, $C_{1-4}$ alkoxy and $C_{3-5}$ cycloalkyl; or a pharmaceutically acceptable salt, solvate or hydrate thereof.

One embodiment of the present invention pertains to compounds of Formula (I) wherein X is O. This embodiment can be represented by Formula (Ic) as illustrated below:

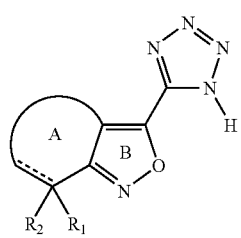

(Ic)

wherein each variable in Formula (Ic) has the same meaning as described herein, supra and infra.

One embodiment of the present invention pertains to compounds of Formula (I) wherein $R_1$ is selected from the group consisting of H, halogen, hydroxy, $C_{1-4}$ haloalkyl, $C_{1-4}$ alkyl, $C_{1-4}$ alkoxy, $C_{2-4}$ alkenyl, $C_{2-4}$ alkynyl, $C_{1-4}$ alkylthio, and CoA haloalkoxy. In some embodiments, $R_1$ is selected from the group consisting of H, halogen, $C_{1-4}$ haloalkyl, and $C_{1-4}$ alkyl. In some embodiments, $R_1$ is F. In some embodiments, $R_1$ is H.

One embodiment of the present invention pertains to compounds of Formula (I) wherein $R_2$ is selected from the group consisting of H, halogen, hydroxy, $C_{1-4}$ haloalkyl, $C_{1-4}$ alkyl, $C_{1-4}$ alkoxy, $C_{2-4}$ alkenyl, $C_{2-4}$ alkynyl, $C_{1-4}$ alkylthio, and $C_{1-4}$ haloalkoxy. In some embodiments, $R_2$ is selected from the group consisting of H, halogen, $C_{1-4}$ haloalkyl, and $C_{1-4}$ alkyl. In some embodiments, $R_2$ is F. In some embodiments, $R_2$ is H.

One embodiment of the present invention pertains to compounds of Formula (I) wherein $R_1$ and $R_2$ are both H.

One embodiment of the present invention pertains to compounds of Formula (I) wherein Ring A is a 5, 6 or 7-membered carbocyclic ring. The term "5, 6 or 7-membered carbocyclic ring" denotes a ring containing 5, 6 or 7 ring carbons wherein two ring carbons are shared by rings A and B. Ring A can be saturated (i.e. no ring double bonds), unsaturated (i.e., containing ring double bonds) or a combination thereof. In some embodiments, ----- is a single bond and $R_2$ is present. This embodiment can be represented by Formula (Ie) as illustrated below:

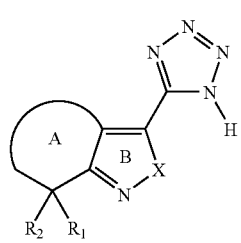

(Ie)

wherein each variable in Formula (Ie) has the same meaning as described herein, supra and infra.

One embodiment of the present invention pertains to compounds having Formula (If):

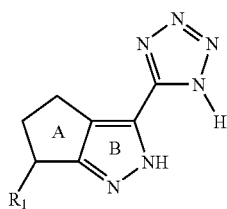

(If)

wherein:

$R_1$ is H or hydroxy; and Ring A is optionally substituted with 1 or 2 substituents selected from the group consisting of halogen, $C_{1-4}$ alkyl, $C_{1-4}$ alkoxy and $C_{3-5}$ cycloalkyl; or a pharmaceutically acceptable salt, solvate or hydrate thereof.

In some embodiments, Ring A is a 5-membered carbocyclic ring. In one embodiment, Ring A is a 5-membered carbocyclic ring and can be represented by Formula (Ig) as illustrated below:

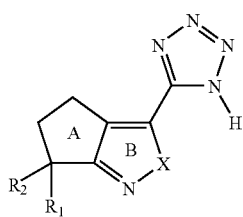

(Ig)

wherein each variable in Formula (Ig) has the same meaning as described herein, supra and infra. In some embodiments, $R_1$ is $C_{1-4}$ alkoxy. In some embodiments, $R_1$ is $C_{1-4}$ alkyl. In some embodiments, $R_1$ and $R_2$ are both H.

One embodiment of the present invention pertains to compounds having Formula (Ih):

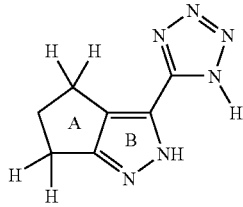

(Ih)

wherein:

Ring A is optionally substituted with 1 or 2 substituents selected from the group consisting of halogen, $C_{1-4}$ alkyl, $C_{1-4}$ alkoxy and $C_{3-5}$ cycloalkyl; or a pharmaceutically acceptable salt, solvate or hydrate thereof.

One embodiment of the present invention pertains to compounds having Formula (Ih):

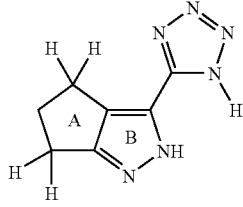

(Ih)

wherein:

Ring A is substituted with 1 or 2 substituents selected from the group consisting of halogen, n-propyl, n-butyl, $C_{1-4}$ alkoxy and $C_{3-5}$ cycloalkyl; or a pharmaceutically acceptable salt, solvate or hydrate thereof.

One embodiment of the present invention pertains to compounds having Formula (Ih):

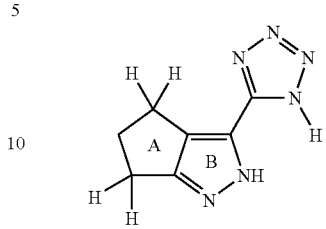

(Ih)

wherein:

Ring A is unsubstituted or is substituted with ethyl; or a pharmaceutically acceptable salt, solvate or hydrate thereof.

In one embodiment, Ring A is a 5-membered carbocyclic ring and is further unsaturated (i.e., a ring double bond). This embodiment can be represented by Formula (Ii) as illustrated below:

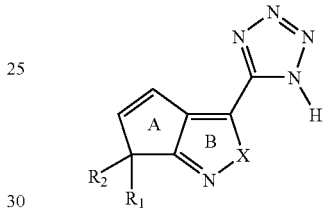

(Ii)

wherein each variable in Formula (Ii) has the same meaning as described herein, supra and infra.

One embodiment of the present invention pertains to compounds of Formula (I) wherein Ring A is a 6-membered carbocyclic ring. This embodiment can be represented by Formula (Ik) as illustrated below:

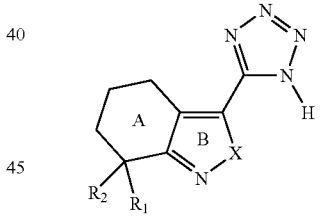

(Ik)

wherein each variable in Formula (Ik) has the same meaning as described herein, supra and infra.

One embodiment of the present invention pertains to compounds of Formula (I) wherein Ring A is a 7-membered carbocyclic ring. This embodiment can be represented by Formula (Im) as illustrated below:

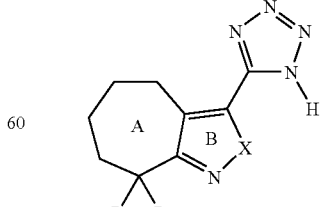

(Im)

wherein each variable in Formula (Im) has the same meaning as described herein, supra and infra.

One embodiment of the present invention pertains to compounds of Formula (I) wherein Ring A is a 5, 6 or 7-membered carbocyclic ring, as described herein supra. In some embodiments, ----- is a double bond and $R_2$ is absent. This embodiment can be represented by Formula (Io) as illustrated below:

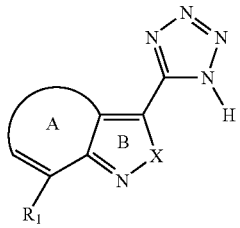

(Io)

wherein each variable in Formula (Io) has the same meaning as described herein, supra and infra. In some embodiments, Ring A is a 5-membered carbocyclic ring. This embodiment can be represented by Formula (Iq) as illustrated below:

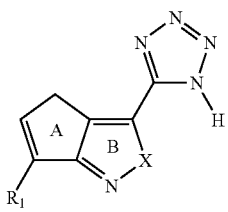

(Iq)

wherein each variable in Formula (Iq) has the same meaning as described herein, supra and infra. In some embodiments, Ring A is a 6-membered carbocyclic ring. In some embodiments, Ring A is a 6-membered carbocyclic ring provided that Ring A is not aromatic. In some embodiments, Ring A is a 7-membered carbocyclic ring.

One embodiment of the present invention pertains to compounds of Formula (I) wherein Ring A is a 5, 6 or 7-membered heterocyclic ring. The term "5, 6 or 7-membered heterocyclic ring" denotes a 5, 6 or 7-membered carbocyclic ring, as described herein supra, wherein 1, 2 or 3 ring carbons not shared by Rings A and B are independently replaced with —O—, —S—, —S(O)—, or —S(O)$_2$—. For clarity, as described herein supra, Ring A can be saturated (i.e. no ring double bonds), unsaturated (i.e., containing ring double bonds) or a combination thereof. In some embodiments, ----- is a single bond and $R_2$ is present. In some embodiments, Ring A is a 5-membered heterocyclic ring. In some embodiments, one ring carbon of the 5-membered heterocyclic ring is replaced with a ring oxygen atom; these embodiments can be represented by the following Formulae (Is) and (It):

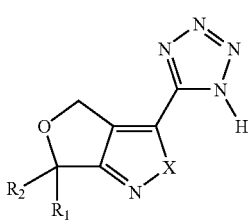

(Is)

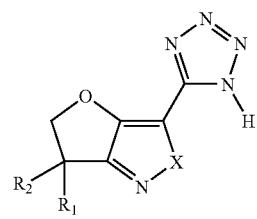

(It)

wherein each variable in Formulae (Is) and (It) have the same meaning as described herein, supra and infra. In some embodiments, compounds of the present invention are of Formula (Is) wherein X is NH. In some embodiments, compounds of the present invention are of Formula (Is) wherein X is O (an oxygen atom). In some embodiments, compounds of the present invention are of Formula (It) wherein X is NH. In some embodiments, compounds of the present invention are of Formula (It) wherein X is O (an oxygen atom). In some embodiments, compounds of the present invention are of Formula (Is) wherein $R_1$ is $C_{1-4}$ alkyl and $R_2$ is H. In some embodiments, compounds of the present invention are of Formula (Is) wherein both $R_1$ and $R_2$ are H. In some embodiments, compounds of the present invention are of Formula (It) wherein $R_1$ is $C_{1-4}$ alkyl and $R_2$ is H. In some embodiments, compounds of the present invention are of Formula (It) wherein both $R_1$ and $R_2$ are H. In some embodiments, one ring carbon of the 5-membered heterocyclic ring is replaced with a ring sulfur atom; these embodiments can be represented by the following Formulae (Iu) and (Iv):

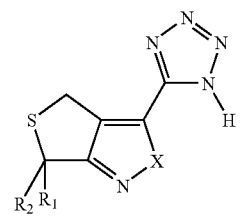

(Iu)

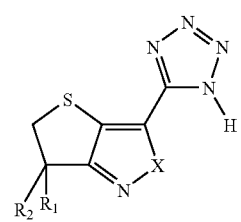

(Iv)

wherein each variable in Formulae (Iu) and (Iv) have the same meaning as described herein, supra and infra. In some embodiments, the ring sulfur in Formulae (Iu) and (Iv) is further oxidized to a sulfoxide (i.e., —S(O)—). In some embodiments, the ring sulfur in Formulae (Iu) and (Iv) is further oxidized to a sulfone (i.e., —S(O)$_2$—). In some embodiments, compounds of the present invention are of Formula (Iu) wherein X is NH. In some embodiments, compounds of the present invention are of Formula (Iu) wherein X is O (an oxygen atom). In some embodiments, compounds of the present invention are of Formula (Iv) wherein X is NH. In some embodiments, compounds of the present invention are of Formula (Iv) wherein X is O (an oxygen atom). In some embodiments, Ring A is a 6-membered heterocyclic ring. In some embodiments, one ring atom of the 6-membered heterocyclic ring is replaced by a ring oxygen atom; these embodiments can be represented by the following Formulae (Ix), (I y), and (Iz):

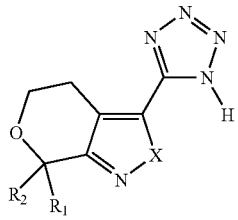

(Ix)

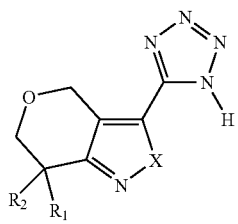

(Iy)

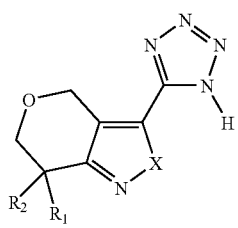

(Iz)

wherein each variable in Formulae (Ix), (Iy), and (Iz) have the same meaning as described herein, supra and infra. In some embodiments, Ring A is a 7-membered heterocyclic ring.

One embodiment of the present invention pertains to compounds of Formula (I) wherein Ring A is a 5, 6 or 7-membered heterocyclic ring. In some embodiments, ┄┄┄ is a double bond and $R_2$ is absent. In some embodiments, Ring A is a 5-membered heterocyclic ring. This embodiment can be represented by Formula (IIa) as illustrated below:

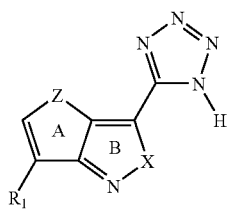

(IIa)

wherein each variable in Formula (IIa) has the same meaning as described herein, supra and infra, and Z is —O—, —S—, —S(O)—, or —S(O)$_2$—.

In some embodiments, Ring A is a 6-membered heterocyclic ring. In some embodiments, the 6-membered heterocyclic ring is a dihydro-pyranyl ring (i.e., one ring carbon is replaced by an oxygen atom); these embodiments can be represented by the following Formulae (IIc) and (IId):

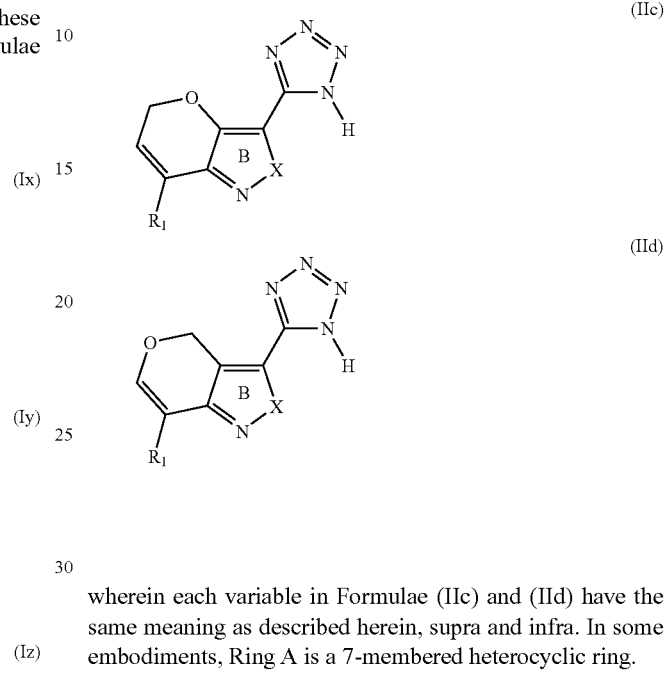

wherein each variable in Formulae (IIc) and (IId) have the same meaning as described herein, supra and infra. In some embodiments, Ring A is a 7-membered heterocyclic ring.

One embodiment of the present invention pertains to compounds of Formula (I), and subgenera disclosed herein, wherein Ring A is optionally substituted with substituents selected from the group consisting of halogen, hydroxy, $C_{1-4}$ haloalkyl, $C_{1-4}$ alkyl, $C_{1-4}$ alkoxy, $C_{2-4}$ alkenyl, $C_{2-4}$ alkynyl, $C_{1-4}$ alkylthio, and $C_{1-4}$ haloalkoxy. In some embodiments, Ring A is optionally substituted with substituents selected from the group consisting of halogen, $C_{1-4}$ haloalkyl, and $C_{1-4}$ alkyl. In some embodiments, Ring A is optionally substituted with F. In some embodiments, Ring A is optionally substituted with 1 to 4 substituents. In some embodiments, Ring A is optionally substituted with 1 to 3 substituents. In some embodiments, Ring A is optionally substituted with 1 to 2 substituents. In some embodiments, Ring A is optionally substituted with 1 substituent. In some embodiments, Ring A is not substituted.

Chemistry of the Present Invention

Synthesis of Compounds of Formula (I)

In one embodiment of the present invention is a synthetic process for the preparation of novel tetrazoles of Formula (I). The compounds of the present invention can be readily prepared according to this novel process utilizing a variety of starting materials that are commercially available or readily prepared by synthetic regimes which would be familiar to one skilled in the art. In the illustrated syntheses outlined below, unless stated otherwise, the labeled substituents have the same identifications as set out in the definitions of the compound described above for Formula (I).

One method that can be used to prepare compounds of the invention wherein X is NH (i.e., Ring B is a pyrazole) utilizes intermediates derived from the cyclic ketone of Formula (A) as illustrated in Reaction Scheme I below:

Scheme I

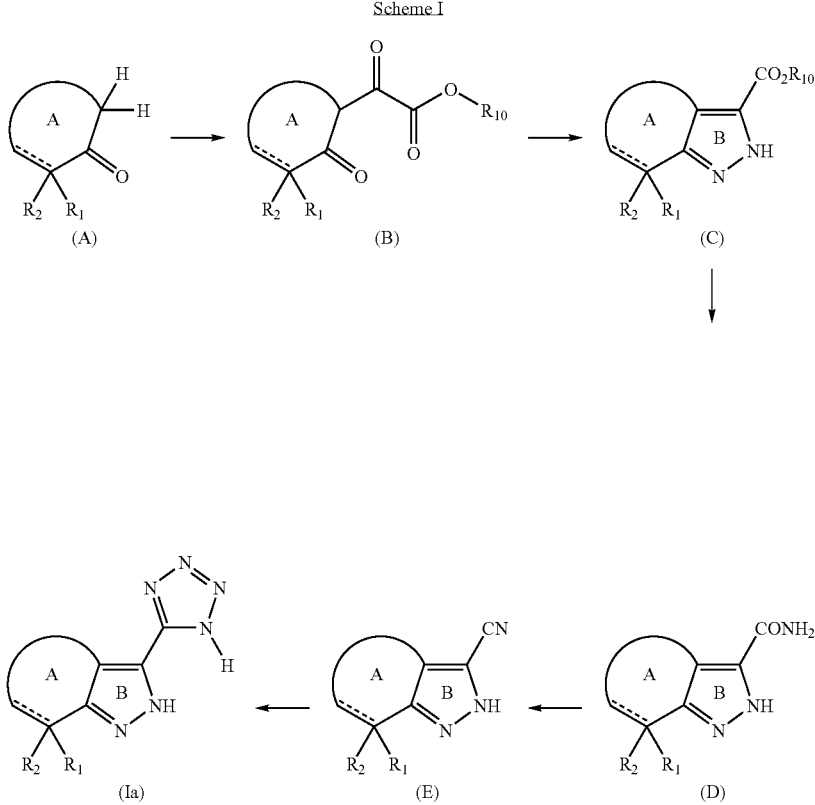

Compounds of Formula (Ia) can be prepared by reacting a cyclic ketone of Formula (A) with dialkyloxalate of formula $(C(O)OR_{10})_2$, wherein $R_{10}$ is a $C_{1-8}$ alkyl, in the presence of a base and a polar solvent such as, but not limited to, $C_{1-8}$ alkanol, methanol, ethanol, butanol, pentanol, hexanol, 2-methoxyethanol, isopropanol, THF, DMF and the like to give ketoester of Formula (B). Suitable bases include alkali metal alkoxides, for example, sodium methoxide, sodium ethoxide, potassium ethoxide, potassium t-butoxide, and the like; alkali metal amides (i.e., alkali metal-$NR_{11}$ wherein $R_{11}$ is $C_{1-8}$ alkyl or silyl-$C_{1-8}$-alkyl), for example, lithium diisopropylamide, lithium hexamethyldisilazane, sodium hexamethyldisilazane, potassium hexamethyldisilazane and like bases. Ketoester (B) is reacted with hydrazine, either protected or unprotected hydrazine can be used, under suitable conditions to give pyrazole ester of Formula (C). Optionally, the pyrazole can be protected, for example, with a benzyl group and the like. The ester is converted to amide of Formula (D) using methods known to one of skill in the art, for example, treating with ammonia in a polar solvent at temperature from room temperature to the boiling point of the solvent. Amide (D) is reacted with a dehydrating reagent, such as phosphorous oxychloride, phosphorous pentoxide, thionyl chloride, and the like, either neat or in the presence of a nonprotic solvent, such as acetonitrile, DMF, and the like, to give nitrile (E). Nitrile (E) is reacted with an azide (i.e., $N_3$) or azide equivalent, such as, sodium azide, potassium azide, trimethylsilyl azide (i.e., $(CH_3)SiN_3$), and the like to give tetrazole of Formula (Ia). In some instances it can be beneficial to include the presence of a Lewis acid, for example, $AlCl_3$, $ZnBr_2$, and the like, in a suitable solvent, such as, DMF and the like.

One method that can be used to prepare compounds of Formula (I) wherein X is a ring oxygen (i.e., Ring B is a isoxazole) utilizes intermediates derived from the alkynyl alcohol of Formula (J) as illustrated in Reaction Scheme II below:

Scheme II

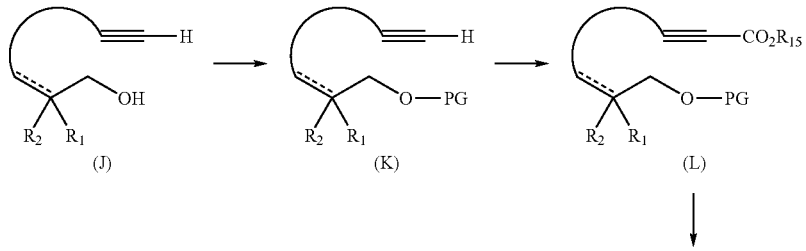

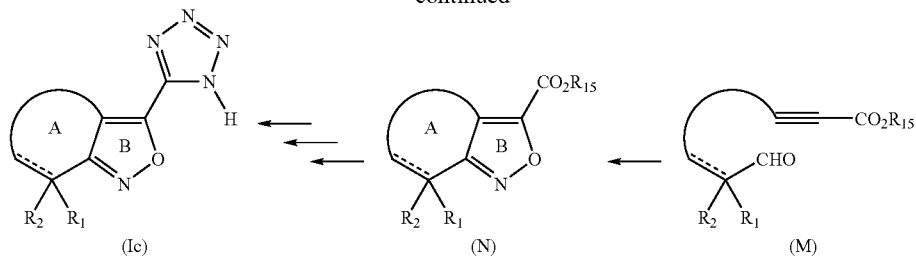

Compounds of Formula (Ic) can be prepared by protecting an alkynyl alcohol of Formula (J) with a suitable protecting group, for example, THP, TBDMS, and the like to give alkynyl (K). Alkynyl (K) is converted to an alkynyl ester of Formula (L, wherein $R_{15}$ is $C_{1-8}$ alkyl) by treatment with a strong base followed by reacting with a $C_{1-8}$ alkyl chloroformate. A suitable strong base is an alkyl lithium, for example but not limited to, n-butyl lithium, t-butyl lithium and the like. Intermediate (L) is subsequently deprotected using methods known to those of skill in the art, for example, the THP group can typically be removed via treatment with an acid (e.g. PTSA) and TBDMS group can typically be removed via treatment with a tetra-alkylammonium fluoride. The resulting alcohol is oxidized to aldehyde (M) using any variety of methods, for example, Dess-Martin periodinane (i.e., 1,1,1-triacetoxy-1,1-dihydro-1,2-benziodoxol-3(1H)-one), Swern Oxidation, Corey oxidation with NCS or any other suitable method as described by Hudlicky, M. in *Oxidations in Organic Chemistry, ACS Monograph* 186 (1990). Aldehyde (M) is treated with hydroxylamine in the presence of a base, followed by NCS and Base to give isoxazole alkylester (N). Isoxazole (N) can be converted to compounds of Formula (Ic) in a substantially similar manner as described above in Reaction Scheme 1, (i.e., —$CO_2$—$C_{1-8}$-alkyl→—$CONH_2$→—C≡N→-tetrazole).

One method that can be used to prepare certain compounds of Formula (I) utilizes intermediate (AJ) as illustrated in Reaction Schemes III and IV below:

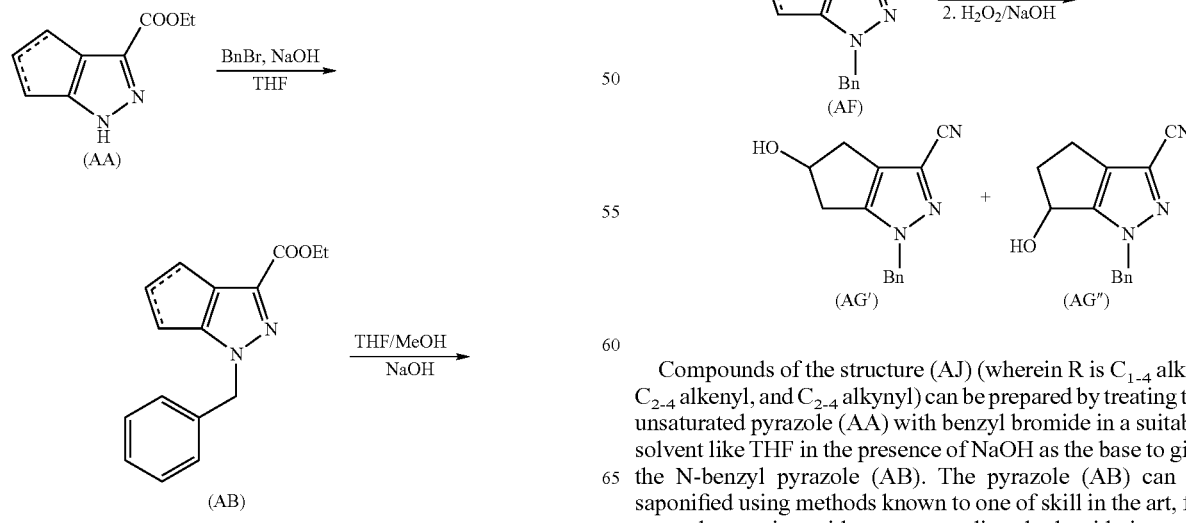

Compounds of the structure (AJ) (wherein R is $C_{1-4}$ alkyl, $C_{2-4}$ alkenyl, and $C_{2-4}$ alkynyl) can be prepared by treating the unsaturated pyrazole (AA) with benzyl bromide in a suitable solvent like THF in the presence of NaOH as the base to give the N-benzyl pyrazole (AB). The pyrazole (AB) can be saponified using methods known to one of skill in the art, for example, treating with aqueous sodium hydroxide in a solvent mixture such as THF/MeOH. The acid (AC) is coupled with N-hydroxy succinimide using a coupling reagent such as EDC. The ester (AD) is converted to the amide (AE) by treatment with concentrated NH$_4$OH solution in a solvent such as 1,4-dioxane. The amide (AE) can be reacted with a dehydrating reagent such as cyanuric chloride, trifluro acetic anhydride, thionyl chloride and like, in the presence of a non protic solvent such as DMF to give the nitrile (AF). The nitrile (AF) is treated with an excess of borane-THF solution in a solvent like THF at low temperature, followed by oxidation with hydrogen peroxide in the presence of sodium hydroxide to give a 1:1 mixture of alcohols shown as (AG') and (AG").

Utilizing either alcohol (AG') or alcohol (AG") a variety of ethers can be prepared. A representative synthesis is shown in Reaction Scheme IV using alcohol (AG'). It is understood that a similar synthetic scheme can be utilized starting with alcohol (AG").

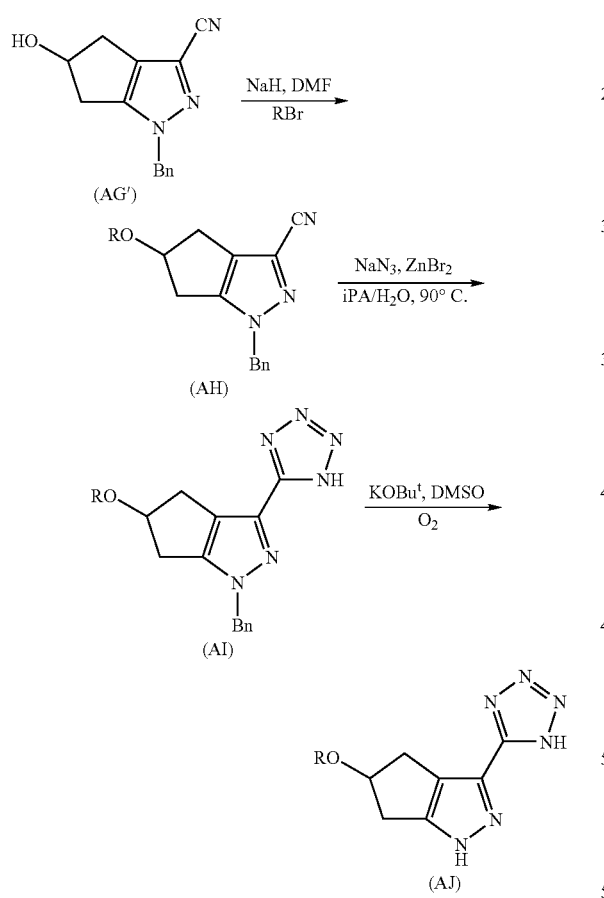

Compounds of the structure (AH) can be prepared by treating the alcohol intermediate (AG') with an excess of alkyl halide in the presence of a base such as sodium hydride in an aprotic solvent such as DMF. The nitrile (AH) is reacted with an azide such as sodium azide, in the presence of a Lewis acid such as zinc bromide, to give the tetrazole of the structure (AI). Final compounds can be prepared by removal of the benzyl protecting group under oxidative conditions in a solvent like DMSO using a base such as potassium t-butoxide and oxygen gas.

One method that can be used to prepare certain compounds of Formula (I) utilizes intermediate (AS) as illustrated in Reaction Scheme V below:

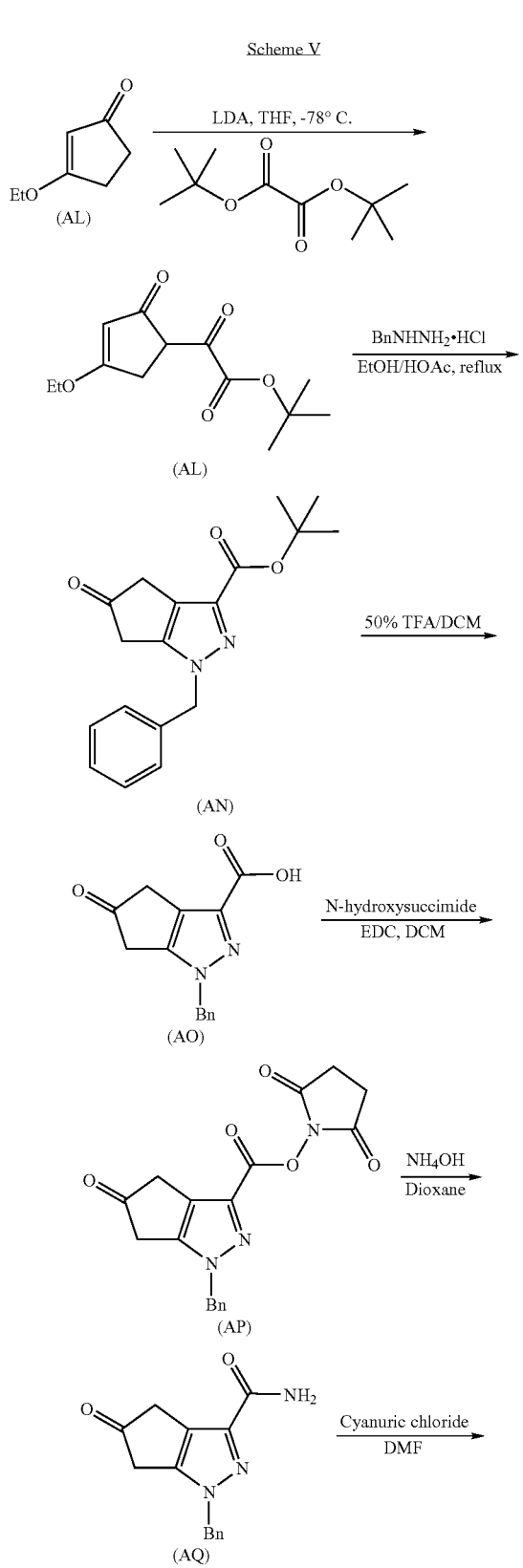

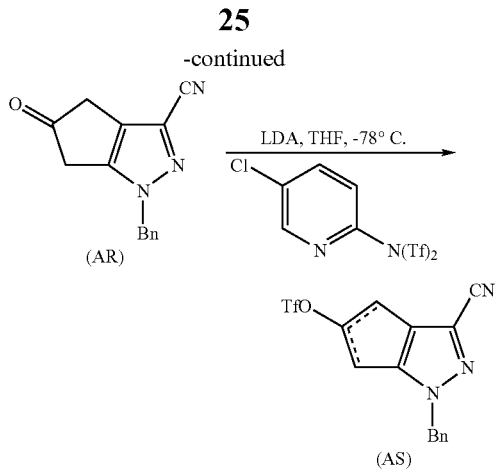

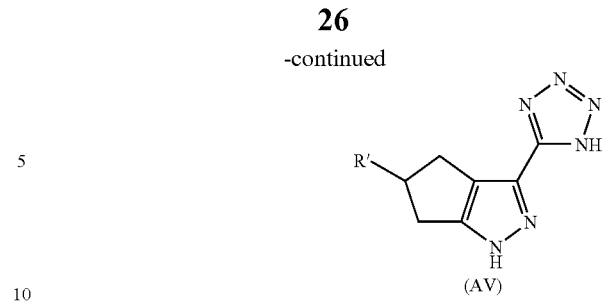

Compounds of the structure (AV) can be prepared from 3-ethoxy-cyclopentenone by treatment with dialkyloxalate such as di-tert-butyl oxalate or diethyloxalate in the presence of a non-nucleophilic base such as LDA or LHMDS in a solvent such as THF to give the keto-ester (AM). The keto ester (AM) is reacted with benzyl hydrazine under reflux in a polar solvent, such as ethanol or methanol containing glacial acetic acid to give the pyrazole (AN). Alternatively, the keto-ester (AM) can be reacted with hydrazine, followed by alkylation of the pyrazole with benzyl bromide using cesium carbonate as the base in a non-protic solvent such as DMF. The pyrazole ester (AN) can be converted to the nitrile (AR) using a similar sequence of steps described for (AG'). The ketone (AR) is converted to the vinyl triflate (AS) using Commins' reagent in the presence of LDA in a solvent such as THF.

Utilizing compound (AS), a variety of substituents (wherein R' is $C_{1-4}$ alkyl, $C_{2-4}$ alkenyl, and $C_{2-4}$ alkynyl) can be introduced at C-5 as shown in Reaction Scheme VI.

The triflate (AS) can be reacted with a suitable stannane reagent in the presence of a base such as lithium chloride and a catalyst such as tetrakis triphenyl phosphine palladium (0) in a suitable solvent such as THF or toluene. Alternatively, the triflate (AS) can be reacted with a suitable alkenyl boronic acid in the presence of a base such as potassium phosphate and a catalyst such as tetrakis triphenyl phosphine palladium (0) in a suitable solvent such as 1,4-dioxane. The nitrile (AT) is reacted with an azide such as sodium azide, in the presence of a Lewis acid such as zinc bromide, to give the tetrazole of the structure (AU). Final compounds are prepared by the removal of the benzyl protecting group that can be performed under reductive conditions using palladium black in a polar solvent such as methanol or ethanol and acid such as formic acid or concentrated hydrochloric acid.

Alternatively, alcohol (AG') may be fluorinated using methods known to those skilled in the art, such as DAST [(diethylamino)sulfur trifluoride], to provide a fluoro compound which can be elaborated to its tetrazole derivative and deprotected using methods described herein.

One method that can be used to prepare certain compounds of Formula (I) is illustrated in Reaction Scheme VII below:

Scheme VII

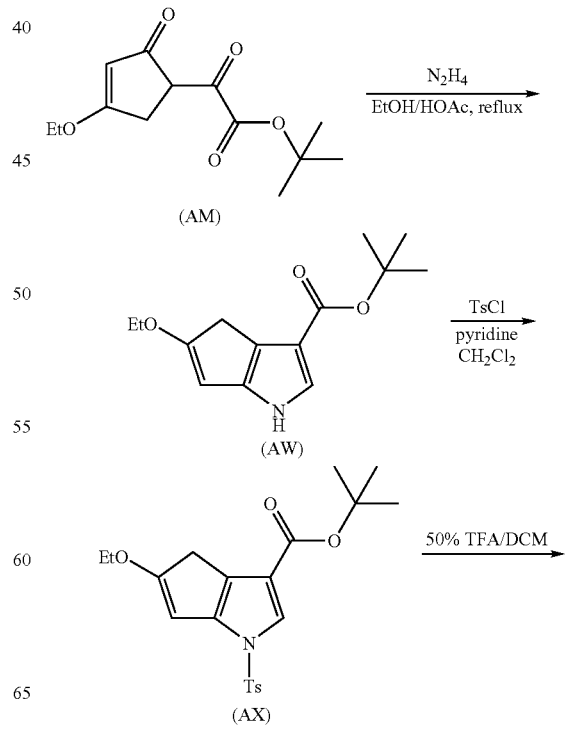

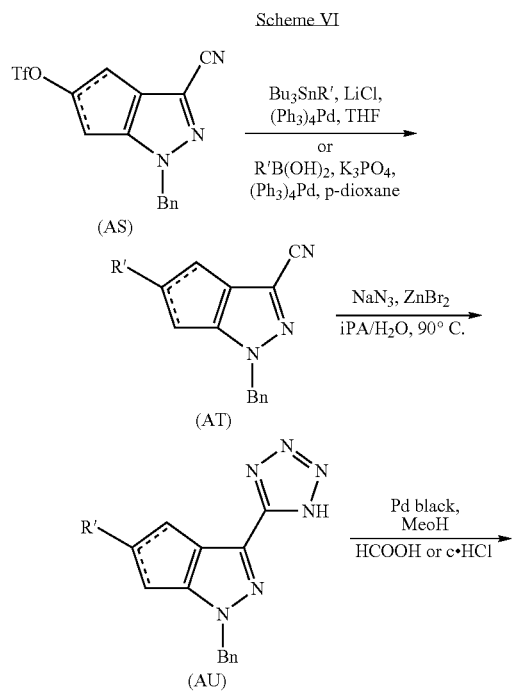

-continued

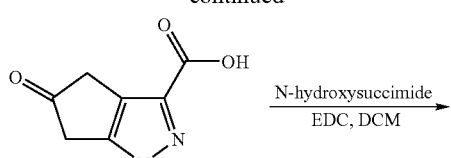
(AY)

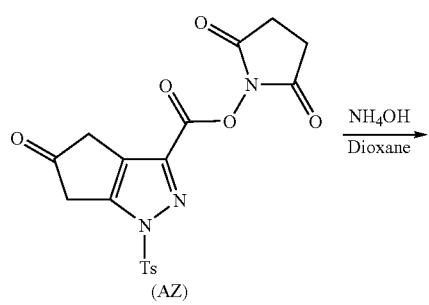
(AZ)

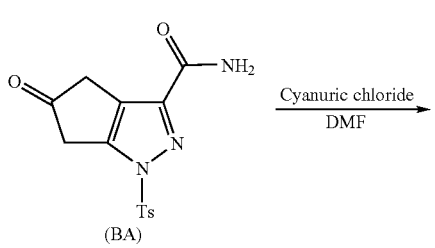
(BA)

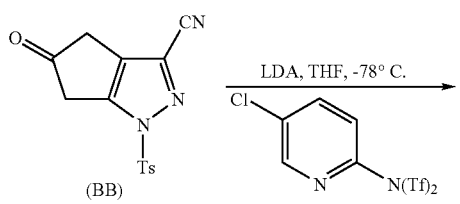
(BB)

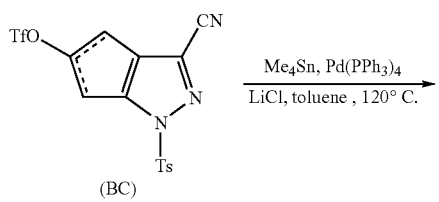
(BC)

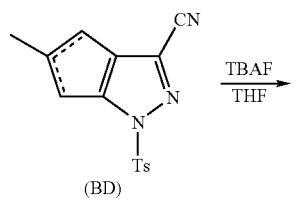
(BD)

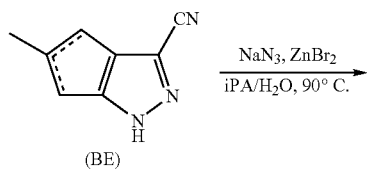
(BE)

-continued

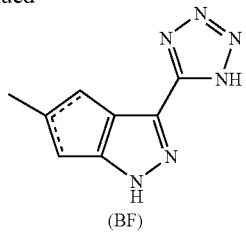
(BF)

A compound of the structure (BF) can be prepared from the keto ester (AM) by reacting with hydrazine hydrate in a polar solvent such as ethanol containing glacial acetic acid to give the pyrazole (AW). The pyrazole (AW) can be reacted with a sufonyl chloride such as p-toluene sulfonyl chloride in a solvent such as $CH_2Cl_2$ in the presence of a base such as pyridine to give the N-sulfonylated derivative (AX). The pyrazole ester (AX) can be deprotected under acidic conditions using an acid such as TFA in $CH_2Cl_2$ to form (AY). The pyrazole acid (AY) can be converted to the nitrile (BB) using a similar sequence of steps described for (AG'). The ketone (BB) can be converted to the vinyl triflate (BC) using Commins' reagent in the presence of a base such as LDA in a solvent such as THF.

The triflate (BC) can be coupled with tetramethyltin in the presence of a base such as lithium chloride and a catalyst such as tetrakis triphenyl phosphine palladium (0) in a suitable solvent such as THF or toluene. The p-toluene sulfonyl group can be removed by reacting with tetra butyl ammonium fluoride solution in a solvent such as THF to give the pyrazole (BE). The final compound is prepared by reacting the nitrile (BE) with an azide such as sodium azide, in the presence of a Lewis acid such as zinc bromide, to give the tetrazole (BF).

The various organic group transformations and protecting groups utilized herein can be performed by a number of procedures other than those described above. References for other synthetic procedures that can be utililized for the preparation of intermediates or compounds disclosed herein can be found in, for example, Smith, M. B.; and March, J., *Advanced Organic Chemistry*, $5^{th}$ Edition, Wiley-Interscience (2001); Larock, R. C., *Comprehensive Organic Transformations, A Guide to Functional Group Preparations*, $2^{nd}$ -Edition, VCH Publishers, Inc. (1999), or Wuts, P. G. M.; Greene, T. W.; *Protective Groups in Organic Synthesis*, $3^{rd}$ Edition, John Wiley and Sons, (1999), all three incorporated herein by reference in their entirety.

Compounds of Formula (I) may have one or more chiral centers, and therefore exist as enantiomers or diastereomers. The invention is understood to extend to all such enantiomers, diastereomers and mixtures thereof, including racemates. Formula (I) and the formulae described herein, supra, are intended to represent all individual isomers and mixtures thereof, unless stated or shown otherwise.

Racemic mixtures can be resolved into the optical pure enatiomers by known methods, for example, by separation of diastereomeric salts thereof with an optically active acid, and liberating the optically active amine compound by treatment with a base. Another method for resolving racemates into the optical pure enatiomers is based upon chromatography on an optically active matrix or chiral support. Certain racemic compounds of the present invention can thus be resolved into their optical antipodes, e.g., by fractional crystallization of d- or l-(tartrates, mandelates, or camphorsulphonate) salts for example. The compounds of the present invention may also be resolved by the formation of diastereomeric amides or ester by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like subsequently hydrolyzed.

Additional methods for the resolution of optical isomers known to those skilled in the art can be used and will be apparent to the average worker skilled in the art. Such methods include those discussed by J. Jaques, A. Collet, and S. Wilen in "Enantiomers, Racemates, and Resolutions", John Wiley and Sons, New York (1981).

It is understood that the chemistry described herein is representative and is not intended to be limiting in any manner.

Representative examples of compound of Formula (I) are shown below in TABLE A.

TABLE A

| Cmpd# | Structure | Chemical Name |
| --- | --- | --- |
| 1 | 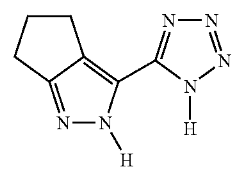 [SMILES: C1Cc2n[nH]c(-c3nnn[nH]3)c2C1] | 3-(1H-Tetrazol-5-yl)-2,4,5,6-tetrahydro-cyclopentapyrazole |
| 2 | 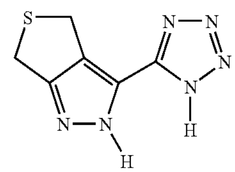 [SMILES: C1SCc2c1n[nH]c2-c1nnn[nH]1] | 3-(1H-Tetrazol-5-yl)-2,6-dihydro-4H-thieno[3,4-c]pyrazole |
| 3 | 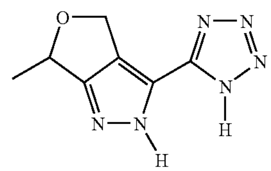 | 6-Methyl-3-(1H-tetrazol-5-yl)-2,6-dihydro-4H-furo[3,4-c]pyrazole |
| 4 | 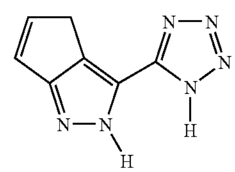 [SMILES: C1=Cc2n[nH]c(-c3nnn[nH]3)c2C1] | 3-(1H-Tetrazol-5-yl)-2,4-dihydro-cyclopentapyrazole |
| 5 | 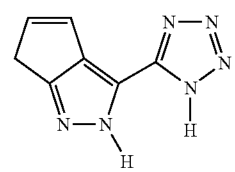 [SMILES: C1=Cc2c(n[nH]c2-c2nnn[nH]2)C1] | 3-(1H-Tetrazol-5-yl)-2,6-dihydro-cyclopentapyrazole |
| 6 | 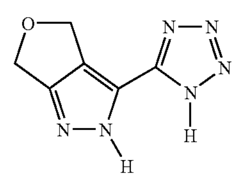 [SMILES: C1OCc2c1n[nH]c2-c1nnn[nH]1] | 3-(1H-Tetrazol-5-yl)-2,6-dihydro-4H-furo[3,4-c]pyrazole |
| 7 | 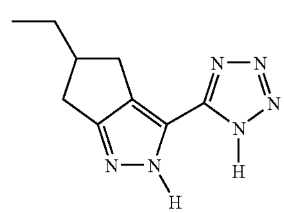 | 5-Ethyl-3-(1H-tetrazol-5-yl)-2,4,5,6-tetrahydro-cyclopentapyrazole |

TABLE A-continued

| Cmpd# | Structure | Chemical Name |
| --- | --- | --- |
| 8 | 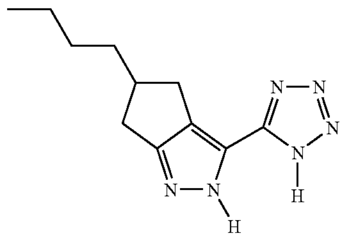 [SMILES: CCCCC1Cc2n[nH]c(-c3nnn[nH]3)c2C1] | 5-Butyl-3-(1H-tetrazol-5-yl)-2,4,5,6-tetrahydro-cyclopentapyrazole |
| 9 | 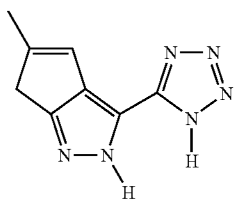 | 5-Methyl-3-(1H-tetrazol-5-yl)-2,6-dihydro-cyclopentapyrazole |
| 10 | 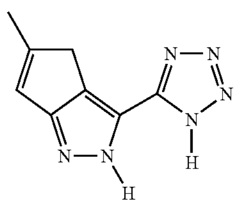 | 5-Methyl-3-(1H-tetrazol-5-yl)-2,4-dihydro-cyclopentapyrazole |
| 11 | 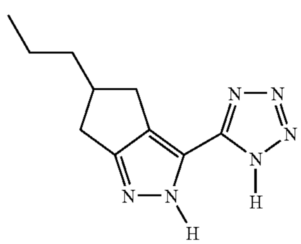 [SMILES: CCCC1Cc2n[nH]c(-c3nnn[nH]3)c2C1] | 5-Propyl-3-(1H-tetrazol-5-yl)-2,4,5,6-tetrahydro-cyclopentapyrazole |
| 12 | 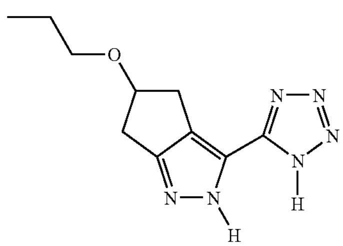 [SMILES: CCCOC1Cc2n[nH]c(-c3nnn[nH]3)c2C1] | 5-Propoxy-3-(1H-tetrazol-5-yl)-2,4,5,6-tetrahydro-cyclopentapyrazole |
| 13 | 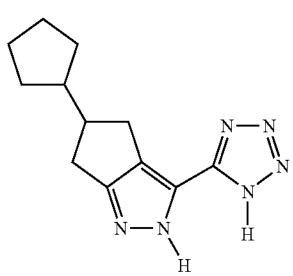 [SMILES: C1CCC(C2Cc3n[nH]c(-c4nnn[nH]4)c3C2)C1] | 5-Cyclopentyl-3-(1H-tetrazol-5-yl)-2,4,5,6-tetrahydro-cyclopentapyrazole |

TABLE A-continued

| Cmpd# | Structure | Chemical Name |
|---|---|---|
| 14 | 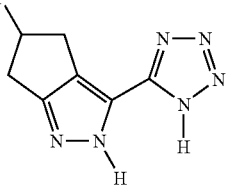 | 5-Fluoro-3-(1H-tetrazol-5-yl)-2,4,5,6-tetrahydro-cyclopentapyrazole |
| 15 | 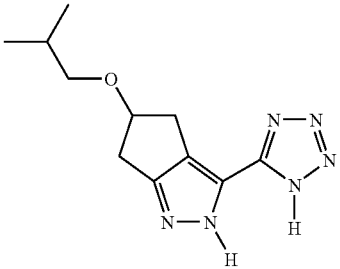 [SMILES: CC(C)COC1Cc2n[nH]c(-c3nnn[nH]3)c2C1] | 5-Isobutoxy-3-(1H-tetrazol-5-yl)-2,4,5,6-tetrahydro-cyclopentapyrazole |
| 16 | 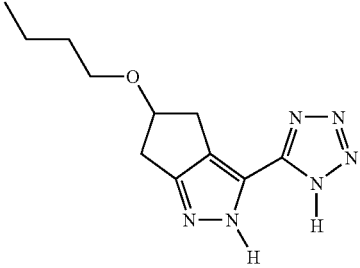 [SMILES: CCCCOC1Cc2n[nH]c(-c3nnn[nH]3)c2C1] | 5-Butoxy-3-(1H-tetrazol-5-yl)-2,4,5,6-tetrahydro-cyclopentapyrazole |
| 17 | 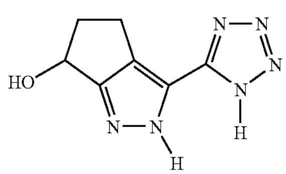 [SMILES: OC1CCc2c1n[nH]c2-c1nnn[nH]1] | 3-(1H-Tetrazol-5-yl)-2,4,5,6-tetrahydro-cyclopentapyrazol-6-ol |
| 18 | 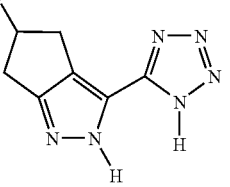 | 5-Methoxy-3-(1H-tetrazol-5-yl)-2,4,5,6-tetrahydro-cyclopentapyrazole |
| 19 | 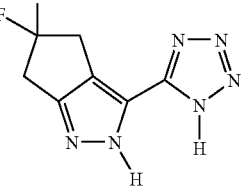 | 5,5-Difluoro-3-(1H-tetrazol-5-yl)-2,4,5,6-tetrahydro-cyclopentapyrazole |

TABLE A-continued

| Cmpd# | Structure | Chemical Name |
|---|---|---|
| 20 | 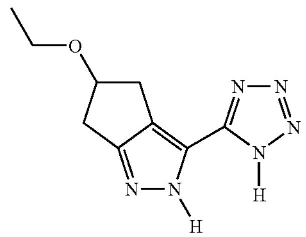 | 5-Ethoxy-3-(1H-tetrazol-5-yl)-2,4,5,6-tetrahydro-cyclopentapyrazole |

Methods and Uses

Compounds of the present invention are useful in the inhibition of the production of free fatty acids. Further, compounds of the present invention are useful in the inhibition of the production of free fatty acids while resulting in substantially lower or in some instances no measurable flushing side effects, which effects are commonly associated with the administration of niacin. Compounds of the present invention typically do not cause vasodilation at doses as high as about 300 mpk as measured using methods know in the art, such as the method shown in Example 7.

In some embodiments, compounds of the present invention cause essentially no measurable flushing in an individual compared to an essentially equally effective dose of niacin. In other embodiments compounds of the present invention cause less than about 80%, 75%, 70%, 65%, 60%, 55%, 50%, 45%, 40%, 35%, 30%, 25%, 20%, 15%, 10%, 5%, or 1% measurable flushing in an individual compared to an essentially equally effective dose of niacin.

Compounds of the present invention can modulate the activity of the RUP25 receptor. The term "modulate" is meant to refer to the ability to increase or decrease activity of the receptor. In some embodiments, compounds of the invention can be used in methods of modulating a RUP25 receptor by contacting the receptor with any one or more of the compound as described herein. In still other embodiments, compounds of the invention can be used in methods of method of modulating a RUP25 receptor for the treatment of a metabolic-related disorder in an individual in need of such modulation comprising contacting the receptor with a therapeutically-effective amount of a compound of Formula (I). In some embodiments, compounds of the invention increase activity of the RUP25 receptor. In further embodiments, compounds of the invention are agonists of the RUP25 receptor. The term "agonist", as used herein, refers to agents that can stimulate activity of the receptor (i.e., activate), like the RUP25 receptor. In some embodiments, compounds of the invention are partial agonists of the RUP25 receptor.

Another aspect of the present invention pertains to methods of treatment of a metabolic-related disorder comprising administering to an individual in need of such treatment a therapeutically-effective amount of a compound of Formula (I).

Another aspect of the present invention pertains to methods of raising HDL in an individual comprising administering to said individual a therapeutically-effective amount of a compound of Formula (I).

Another aspect of the present invention pertains to compounds of Formula (I), as described herein, for use in a method of treatment of the human or animal body by therapy.

Another aspect of the present invention pertains to compounds of Formula (I), as described herein, for use in a method of treatment of a metabolic-related disorder of the human or animal body by therapy.

Another aspect of the present invention pertains to compounds of Formula (I), as described herein, for use in a method of treatment of a metabolic-related disorder of the human or animal body by therapy wherein said metabolic-related disorder is selected from the group consisting of dyslipidemia, atherosclerosis, coronary heart disease, insulin resistance, obesity, impaired glucose tolerance, atheromatous disease, hypertension, stroke, Syndrome X, heart disease and type 2 diabetes.

Another aspect of the present invention pertains to compounds of Formula (I), as described herein, for use in a method of treatment of a metabolic-related disorder of the human or animal body by therapy wherein said metabolic-related disorder is selected from the group consisting of dyslipidemia, atherosclerosis, coronary heart disease, insulin resistance and type 2 diabetes.

Another aspect of the present invention pertains to compounds of Formula (I), as described herein, for use in a method of treatment of atherosclerosis of the human or animal body by therapy.

Another aspect of the present invention pertains to compounds of Formula (I), as described herein, for use in a method of raising HDL of the human or animal body by therapy.

Another aspect of the present invention pertains to uses of the compounds of Formula (I), as described herein, for the manufacture of a medicament for use in the treatment of a metabolic-related disorder.

Another aspect of the present invention pertains to uses of the compounds of Formula (I), as described herein, for the manufacture of a medicament for use in the treatment of a metabolic-related disorder selected from the group consisting of dyslipidemia, atherosclerosis, coronary heart disease, insulin resistance, obesity, impaired glucose tolerance, atheromatous disease, hypertension, stroke, Syndrome X, heart disease and type 2 diabetes.

Another aspect of the present invention pertains to uses of the compounds of Formula (I), as described herein, for the manufacture of a medicament for use in the treatment of atherosclerosis.

Another aspect of the present invention pertains to uses of the compounds of Formula (I), as described herein, for the manufacture of a medicament for use in raising HDL in an individual.

Some embodiments of the present invention relate to methods of treatment of metabolic-related disorders. In some embodiments the metabolic-related disorder is of the group consisting of dyslipidemia, atherosclerosis, coronary heart disease, insulin resistance, obesity, impaired glucose tolerance, atheromatous disease, hypertension, stroke, Syndrome X, heart disease and type 2 diabetes. In some embodiments the metabolic-related disorder is dyslipidemia, atherosclerosis, coronary heart disease, insulin resistance and type 2 diabetes. In some embodiments the metabolic-related disorder is dyslipidemia. In some embodiments the metabolic-related disorder is atherosclerosis. In some embodiments the metabolic-related disorder is coronary heart disease. In some embodiments the metabolic-related disorder is insulin resistance. In some embodiments the metabolic-related disorder is type 2 diabetes.

In some embodiments related to methods of the present invention, the individual is a mammal. In further embodiments, the mammal is a human.

Another aspect of the present invention pertains to methods of producing a pharmaceutical composition comprising admixing or combining a compound of Formula (I), as described herein, and a pharmaceutically acceptable carrier.

Compositions of the Present Invention

Some embodiments of the present invention include pharmaceutical compositions comprising a compound according to Formula (I) in combination with a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations can be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives, and flavorings and colorants can be added to the liquid preparations. Parenteral dosage forms can be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20$^{th}$ Edition, 2000, Lippincott Williams & Wilkins, (Editors: Gennaro, A. R., et al.).

While it is possible that a compound for use in the treatment of the present invention may, in an alternative use, be administered as a raw or pure chemical, it is preferable however to present the compound or "active ingredient" as a pharmaceutical formulation or composition further comprising a pharmaceutically acceptable carrier. Therefore, one aspect of the present invention encompasses pharmaceutical compositions comprising a pharmaceutically acceptable carrier in combination with at least one compound according to Formula (I).

The invention provides pharmaceutical formulations comprising a compound of the invention or a pharmaceutically acceptable salt, hydrate or solvate thereof together with one or more pharmaceutically acceptable carriers therefor. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form can be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water can be used as a suitable pharmaceutically acceptable carrier.

Compounds of the present invention or a solvate or physiologically functional derivative thereof can be used as active ingredients in pharmaceutical compositions, specifically as RUP25 receptor agonists. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated is conducted or on whether further active compounds are administered in addition to the compounds of the present invention. Representative doses of the present invention include, but not limited to, about 0.001 mg to about 5000 mg, about 0.601 to about 2500 mg, about 0.001 to about 1000 mg, 0.001 to about 500 mg, 0.001 mg to about 250 mg, about 0.001 mg to 100 mg, about 0.001 mg to about 50 mg, and about 0.001 mg to about 25 mg. Multiple doses can be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system to another, for example, an animal model to a human. Typically, animal models include, but are not limited to, the rodents diabetes models as described in Example 1, infra; the mouse atherosclerosis model as described in Example 2, infra; or the in vivo animal athosclerosis model as described in Example 5, infra. In some circumstances, these extrapolations may merely be based on the weight of the animal model in comparison to another, such as a mammal, preferably a human, however, more often, these extrapolations are not simply based on weight differences, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated is conducted or on whether further active compounds are administered in addition to the compounds of the Formula (I) and as part of a drug combination. The dosage regimen for treating a disease condition with the compounds and/or compositions of this invention is selected in accordance with a variety factors, such as, those cited above. Thus, the actual dosage regimen employed may vary widely and therefore may deviate from a preferred dosage regimen and one skilled in the art will recognize that dosage and dosage regimen outside these typical ranges can be tested and, where appropriate, can be used in the methods of this invention.

The desired dose may conveniently be presented in a single dose or as divided doses administered at appropriate intervals, for example, as two, three, four or more sub-doses per day. The sub-dose itself can be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it can be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration can be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and can be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention can be formulated as ointments, creams or lotions, or as a transdermal patch.

Ointments and creams may, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations can be provided in single or multi-dose form. In the latter case of a dropper or pipette, this can be achieved by the patient administering an appropriate, predetermined volume of the solution or suspension. In the case of a spray, this can be achieved for example by means of a metering atomizing spray pump.

Administration to the respiratory tract may also be achieved by means of an aerosol formulation in which the active ingredient is provided in a pressurized pack with a suitable propellant. If the compounds of the Formula (I) or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the Formula (I) as an aerosol can be prepared by processes well-known to the person skilled in the art. For their preparation, for example, solutions or dispersions of the compounds of the Formula (I) in water, water/alcohol mixtures or suitable saline solutions can be employed using customary additives, for example benzyen alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug can be controlled by provision of a metered valve.

In formulations intended for administration to the respiratory tract, including intranasal formulations, the compound will generally have a small particle size for example of the order of 10 microns or less. Such a particle size can be obtained by means known in the art, for example by micronization. When desired, formulations adapted to give sustained release of the active ingredient can be employed.

Alternatively the active ingredients can be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition can be presented in unit dose form for example in capsules or cartridges of, e.g., gelatin, or blister packs from which the powder can be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In general, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Combination Therapy:

While the compounds of the present invention can be administered as the sole active pharmaceutical agent (i.e., mono-therapy), they can also be used in combination with other pharmaceutical agents (i.e., combination-therapy), such as, for the treatment of the diseases/conditions/disorders described herein. Therefore, another aspect of the present invention includes methods of treatment of metabolic related diseases comprising administering to an individual in need of such treatment a therapeutically-effective amount of a compound of the present invention in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholecystokinin-A (CCK-A) agonists, serotonin and norepinephrine reuptake inhibitors (for example, sibutramine), sympathomimetic agents, $\beta_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company; Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

It is understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of concomitant disorders. Treatment of such disorders include the use of one or more pharmaceutical agents known in the art that belong to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II-receptor antagonists and adiponectin. In accordance to one aspect of the present invention, a compound of the present can be used in combination with a pharmaceutical agent or agents belonging to one or more of the classes of drugs cited herein.

It is understood that the scope of combination-therapy of the compounds of the present invention with other pharmaceutical agents is not limited to those listed herein, supra or infra, but includes in principle any combination with any pharmaceutical agent or pharmaceutical composition useful for the treatment of diseases, conditions or disorders that are linked to metabolic-related disorders.

Some embodiments of the present invention include methods of treatment of a disease, disorder or condition as described herein comprising administering to an individual in need of such-treatment a therapeutically effect amount or dose of a compound of the present invention in combination with at least one pharmaceutical agent selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, the pharmaceutical composition further comprises one or more agents selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

One aspect of the present invention encompasses pharmaceutical compositions comprising at least one compound according to Formula (I), as described herein. In some embodiments, the pharmaceutical composition further comprises one or more agents selected from the group consisting of, for example, α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

Suitable pharmaceutical agents that can be used in conjunction with compounds of the present invention include α-glucosidase inhibitors. α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides: The meglitinides are benzoic acid derivatives represent a novel class of insulin secretagogues. These agents target postprandial hyperglycemia and show comparable efficacy to sulfonylureas in reducing $HbA_{1c}$. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of the present invention include the α-glucosidase inhibitors. The α-glucosidase inhibitors competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Examples of x-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include the peroxisoine proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, pitavastatin, BMS's "superstatin", and HMG-CoA reductase inhibitors known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form), and angiotensin II receptor antagonists known in the art.

Other treatments for one or more of the diseases cited herein include the use of one or more pharmaceutical agents known in the art that belong to the classes of drugs referred to, but not limited to, the following: amylin agonists (for example, pramlintide), insulin secretagogues (for example, GLP-1 agonists; exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, torcetrapib and like compounds), microsomal triglyceride transfer protein inhibitors (for example, implitapide, and like compounds), cholesterol modulators (for example, NO-1886, and like compounds), bile acid modulators (for example, GT103-279 and like compounds) and squalene synthase inhibitors.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy]phosphinyl]-3-phenoxybenzenebutanesulfonic acid, mono potassium salt (BMS-188494) and squalene synthesis inhibitors known in the art.

In accordance with the present invention, the combination can be used by mixing the respective active components either all together or independently with a pharmaceutically acceptable carrier, excipient, binder, diluent, etc., as described herein above, and administering the mixture or mixtures either orally or non-orally as a pharmaceutical composition. When a compound or a mixture of compounds of Formula (I) are administered as a combination therapy with another active compound the therapeutic agents can be formulated as separate pharmaceutical compositions given at the same time or at different times, or the therapeutic agents can be given as a single composition.

In accordance with the present invention, the combination of a compound of the present invention and pharmaceutical agent can be prepared by mixing the respective active components either all together or independently with a pharmaceutically acceptable carrier, excipient, binder, diluent, etc., as described herein, and administering the mixture or mixtures either orally or non-orally as a pharmaceutical composition. When a compound or a mixture of compounds of Formula (I) are administered as a combination therapy with another active compound the therapeutic agents can be formulated as a separate pharmaceutical compositions given at the same time or at different times, or the therapeutic agents can be given as a single composition.

Labeled Compounds and Assay Methods

Another object of the present invention relates to radiolabeled compounds of Formula (I) that are useful not only in radio-imaging but also in assays, both in vitro and in vivo, for localizing and quantitating RUP25 in tissue samples, including human, and for identifying RUP25 ligands by inhibition binding of a radio-labeled compound. It is a further object of this invention to include novel RUP25 assays of which comprise such radio-labeled compounds.

The present invention embraces isotopically-labeled compqunds of Formula (I) and any subgenera herein, such as but not limited to, Formulae (Ia) to (Iz); and (IIa) to (IId). An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that can be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, and $^{131}I$. The radionuclide that is incorporated in the instant radio-labeled compounds will depend on the specific application of that radio-labeled compound. For example, for in vitro RUP25 labeling and competition assays, compounds that incorporate $^3H$, $^{14}C$, $^{82}Br$, $^{125}I$, $^{131}I$, $^{35}S$ or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of Formula (I) that has incorporated at least one radionuclide; in some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence can be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules, and are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling —This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I, into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in *J. Org. Chem.* 2002, 67, 943-948.

B. Ortho $^{125}$Iodination of phenols—This procedure allows for the incorporation of $^{125}$I at the ortho position of a phenol as reported by Collier, T. L. and co-workers in *J. Labeled Compd Radiopharm.* 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

A radio-labeled RUP25 compound of Formula (I) can be used in a screening assay to identify/evaluate compounds. In general terms, a newly synthesized or identified compound (i.e., test compound) can be evaluated for its ability to reduce binding of the "radio-labeled compound of Formula (I)" to the RUP25 receptor. Accordingly, the ability of a test compound to compete with the "radio-labeled compound of Formula (I)" for the binding to the RUP25 receptor directly correlates to its binding affinity.

The labeled compounds of the present invention bind to the RUP25 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM, and in still yet another embodiment the labeled inhibitor has an IC$_{50}$ less than about 0.1 µM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

The following Examples are provided for illustrative purposes and not as a means of limitation. One of ordinary skill in the art would be able to design equivalent assays and methods based on the disclosure herein, all of which form part of the present invention.

Example 1

Rodent Diabetes Models

Rodent models of type 2 diabetes associated with obesity and insulin resistance have been developed. Genetic models such as db/db and ob/ob [see Diabetes (1982) 31:1-6] in mice and fa/fa in zucker rats have been developed for understanding the pathophysiology of disease and for testing candidate therapeutic compounds [Diabetes (1983) 32:830-838; Annu Rep Sankyo Res Lab (1994) 46:1-57]. The homozygous animals, C57 BL/KsJ-db/db mice developed by Jackson Laboratory are obese, hyperglycemic, hyperinsulinemic and insulin resistant [J Clin Invest (1990) 85:962-967], whereas heterozygotes are lean and normoglycemic. In the db/db model, mice progressively develop insulinopenia with age, a feature commonly observed in late stages of human type 2 diabetes when sugar levels are insufficiently controlled. Since this model resembles that of human type 2 diabetes, the compounds of the present invention are tested for activities including, but not limited to, lowering of plasma glucose and triglycerides. Zucker (fa/fa) rats are severely obese, hyperinsulinemic, and insulin resistant {Coleman, Diabetes (1982) 31:1; E Shafrir in Diabetes Mellitus, H Rifkin and D Porte, Jr, Eds [Elsevier Science Publishing Co, New York, ed. 4, (1990), pp. 299-340]}, and the fa/fa mutation may be the rat equivalent of the murine db mutation [Friedman et al, Cell (1992) 69:217-220; Truett et al, Proc Natl Acad Sci USA (1991) 88:7806]. Tubby (tub/tub) mice are characterized by obesity, moderate insulin resistance and hyperinsulinemia without significant hyperglycemia [Coleman et al, Heredity (1990) 81:424].

The present invention encompasses the use of compounds of the invention for reducing the insulin resistance and hyperglycemia in any or all of the above rodent diabetes models, in humans with type 2 diabetes or other preferred metabolic-related disorders or disorders of lipid metabolism described previously, or in models based on other mammnals. Plasma glucose and insulin levels will be tested, as well as other factors including, but not limited to, plasma free fatty acids and triglycerides.

In Vivo Assay for Anti-Hyperglycemic Activity of Compounds of the Invention

Genetically altered obese diabetic mice (db/db) (male, 7-9 weeks old) are housed (7-9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide compounds of the invention, saline, or an irrelevant compound to the mice subcutaneously (s.c.). Blood is sampled from the tail vein at intervals thereafter and analyzed for blood glucose concentrations. Significant differences between groups (comparing compounds of the invention to saline-treated) are evaluated using Student t-test.

Example 2

Mouse Atherosclerosis Model

Adiponectin-deficient mice generated through knocking out the adiponectin gene have been shown to be predisposed to atherosclerosis and to be insulin resistant. The mice are also a suitable model for ischemic heart disease [Matsuda, M et al. J Biol Chem (2002) July, and references cited therein, the disclosures of which are incorporated herein by reference in their entirety].

Adiponectin knockout mice are housed (7-9 mice/cage) under standard laboratory conditions at 22° C. and 50% relative humidity. The mice are dosed by micro-osmotic pumps, inserted using isoflurane anesthesia, to provide compounds of the invention, saline, or an irrelevant compound to the mice subcutaneously (s.c.). Neointimal thickening and ischemic heart disease are determined for different groups of mice sacrificed at different time intervals. Significant differences between groups (comparing compounds of the invention to saline-treated) are evaluated using Student t-test.

Example 3

In Vitro Biological Activity

A modified Flash Plate™ Adenylyl Cyclase kit (New England Nuclear; Cat. No. SMP004A) was utilized for direct identification of candidate compounds as agonists to hRUP25 in accordance with the following protocol. The term hRUP25 includes the human sequences found in GenBank Accession No. NM_177551 for the nucleotide and GenBank Accession No. NP 808219 for the polypeptide, and naturally-occurring allelic variants, mammalian orthologs, and recombinant mutants thereof.

CHO cells stably transfected with an expression vector encoding hRUP25 and cultured under condition permissive for cell surface expression of the encoded hRUP25 receptor were harvested from flasks via non-enzymatic means. The cells were washed in PBS and resuspended in the manufacturer's Assay Buffer. Live cells were counted using a hemacytometer and Trypan blue exclusion, and the cell concentration was adjusted to $2\times10^6$ cells/ml. cAMP standards and Detection Buffer (comprising 2 µCi of tracer [$^{125}$I]-cAMP (100 µl) to 11 ml Detection Buffer) were prepared and maintained in accordance with the manufacturer's instructions. Candidate compounds identified as per above (if frozen, thawed at room temperature) were added to their respective wells (preferably wells of a 96-well plate) at increasing concentrations (3 µl/well; 12 µM final assay concentration). To these wells, 100,000 cells in 50 µl of Assay Buffer were added and the mixture was then incubated for 30 minutes at room temperature, with gentle shaking. Following the incubation, 100 µl of Detection Buffer was added to each well, followed by incubation for 2-24 hours. Plates were counted in a Wallac MicroBeta™ plate reader using "Prot. #31" (as per manufacturer instructions).

Certain compounds of the invention have an $EC_{50}$ in the cAMP Whole Cell method of about 25 µM or less.

Example 4

In Vitro Biological Activity $^{35}$S-GTPγS Binding Assay:

Membranes prepared from Chinese Hamster Ovary (CHO)-K1 cells stably expressing the niacin receptor or vector control (7 µg/assay) were diluted in assay buffer (100 mM HEPES, 100 mM NaCl and 10 mM $MgCl_2$, pH 7.4) in Wallac Scintistrip plates and pre-incubated with test compounds diluted in assay buffer containing 40 µM GDP (final [GDP] was 10 µM) for ~10 minutes before addition of $^{35}$S-GTPγS to 0.3 nM. To avoid potential compound precipitation, all compounds were first prepared in 100% DMSO and then diluted with assay buffer resulting in a final concentration of 3% DMSO in the assay. Binding was allowed to proceed for one hour before centrifuging the plates at 4000 rpm for 15 minutes at room temperature and subsequent counting in a TopCount scintillation counter. Non-linear regression analysis of the binding curves was performed in GraphPad Prism.

Membrane Preparation

Materials:

CHO-K1 cell culture medium: F-12 Kaighn's Modified Cell Culture Medium with 10% FBS, 2 mM L-Glutamine, 1 mM Sodium Pyruvate and 400 µgml G418

Membrane Scrape Buffer: 20 mM HEPES 10 mM EDTA, pH 7.4

Membrane Wash Buffer: 20 mM HEPES 0.1 mM EDTA, pH 7.4

Protease Inhibitor Cocktail: P-8340, (Sigma, St. Louis, Mo.)

Procedure:

Aspirate cell culture media off the 15 $cm^2$ plates, rinse with 5 mL cold PBS and aspirate.

Add 5 mL Membrane Scrape Buffer and scrape cells. Transfer scrape into 50 mL centrifuge tube. Add 50 µL Protease Inhibitor Cocktail.

Spin at 20,000 rpm for 17 minutes at 4° C.

Aspirate off the supernatant and resuspend pellet in 30 mL Membrane Wash Buffer.

Add 50 µL Protease Inhibitor Cocktail.
Spin at 20,000 rpm for 17 minutes at 4° C.
Aspirate the supernatant off the membrane pellet. The pellet may be frozen at −80° C. for later use or it can be used immediately.

Assay
Materials:
Guanosine 5'-diphosphate sodium salt (GDP, Sigma-Aldrich Catalog #87127)
Guanosine 5'-[γ$^{35}$S] thiotriphosphate, triethylammonium salt ([$^{35}$S]GTPγS, Amersham Biosciences Catalog #SJ1320, ~1000 Ci/mmol)
96 well Scintiplates (Perkin-Elmer #1450-501)
Binding Buffer: 20 mM HEPES, pH 7.4
  100 mM NaCl
  10 mM MgCl$_2$
GDP Buffer: binding buffer plus GDP, ranging from 0.4 to 40 µM, make fresh before assay
Procedure:
  (total assay volume=100 µ/well)
  25 µL GDP buffer with or without compounds (final GDP 10 µM—so use 40 µM stock)
  50 µL membrane in binding buffer (0.4 mg protein/mL)
  25 µL [$^{35}$S]GTPγS in binding buffer. This is made by adding 5 µl [$^{35}$S]GTPγS stock into 10 mL binding buffer (This buffer has no GDP)
  Thaw compound plates to be screened (daughter plates with 5 µL compound @ 2 mM in 100% DMSO)
  Dilute the 2 mM compounds 1:50 with 245 µL GDP buffer to 40 µM in 2% DMSO. Thaw frozen membrane pellet on ice
  Homogenize membranes briefly until in suspension using a POLYTRON PT3100 (probe PT-DA 3007/2 at setting of 7000 rpm). Determine the membrane protein concentration by Bradford assay. Dilute membrane to a protein concentrations of 0.40 mg/ml in Binding Buffer. (Note: the final assay concentration is 20 µg/well).
  Add 25 µL compounds in GDP buffer per well to Scintiplate.
  Add 50 µL of membranes per well to Scintiplate.
  Pre-incubate for 5-10 minutes at room temperature.
  Add 25 µL of diluted [$^{35}$S]GTPγS. Incubate on shaker (Lab-Line model #1314, shake at setting of 4) for 60 minutes at room temperature.
  Assay is stopped by spinning plates sealed with plate covers at 2500 rpm for 20 minutes at 22° C.
  Read on TopCount NXT scintillation counter—$^{35}$S protocol.

Certain compounds of the invention have an EC$_{50}$ in the functional in vitro GTPγS binding assay within the range of about 10-100 µM. More advantageous compounds of the invention have an EC$_{50}$ value in this assay within the range of about 1-10 µM. Still more advantages compounds have an EC50 value in this assay of less than about 1 uM.

Example 5

In Vivo Animal Model

One utility of the compound of the present invention as a medical agent in the prophylaxis and treatment of a high total cholesterol/HDL-cholesterol ratio and conditions relating thereto is demonstrated by the activity of the compound in lowering the ratio of total cholesterol to HDL-cholesterol, in elevating HDL-cholesterol, or in protection from atherosclerosis in an in vivo pig model. Pigs are used as an animal model because they reflect human physiology, especially lipid metabolism, more closely than most other animal models. An illustrative in vivo pig model not intended to be limiting is presented here.

Yorkshire albino pigs (body weight 25.5±4 kg) are fed a saturated fatty acid rich and cholesterol rich (SFA-CHO) diet during 50 days (1 kg chow 35 kg$^{-1}$ pig weight), composed of standard chow supplemented with 2% cholesterol and 20% beef tallow [Royo T et al., *European Journal of Clinical Investigation* (2000) 30:843-52; which disclosure is hereby incorporated by reference in its entirety]. Saturated to unsaturated fatty acid ratio is modified from 0.6 in normal pig chow to 1.12 in the SFA-CHO diet. Animals are divided into two groups, one group (n=8) fed with the SFA-CHO diet and treated with placebo and one group (n=8) fed with the SFA-CHO diet and treated with the compound (3.0 mg kg$^{-1}$). Control animals are fed a standard chow for a period of 50 days. Blood samples are collected at baseline (2 days after the reception of the animals), and 50 days after the initiation of the diet. Blood lipids are analyzed. The animals are sacrificed and necropsied.

Alternatively, the foregoing analysis comprises a plurality of groups each treated with a different dose of the compound. Preferred said doses are selected from the group consisting of: 0.1 mg kg$^{-1}$, 0.3 mg kg$^{-1}$, 1.0 mg kg$^{-1}$, 3.0 mg kg$^{-1}$, 10 mg kg$^{-1}$, 30 mg kg$^{-1}$ and 100 mg kg$^{1}$. Alternatively, the foregoing analysis is carried out at a plurality of timepoints. Preferred said timepoints are selected from the group consisting of 10 weeks, 20 weeks, 30 weeks, 40 weeks, and 50 weeks.

HDL-Cholesterol

Blood is collected in trisodium citrate (3.8%, 1:10). Plasma is obtained after centrifugation (1200 g 15 min) and immediately processed. Total cholesterol, HDL-cholesterol, and LDL-cholesterol are measured using the automatic analyzer Kodak Ektachem DT System (Eastman Kodak Company, Rochester, N.Y., USA). Samples with value parameters above the range are diluted with the solution supplied by the manufacturer and then re-analyzed. The total cholesterol/HDL-cholesterol ratio is determined. Comparison is made of the level of HDL-cholesterol between groups. Comparison is made of the total cholesterol/HDL-cholesterol ratio between groups.

Elevation of HDL-cholesterol or reduction of the total cholesterol/HDL-cholesterol ratio on administration of the compound is taken as indicative of the compound having the aforesaid utility.

Atherosclerosis

The thoracic and abdominal aortas are removed intact, opened longitudinally along the ventral surface, and fixed in neutral-buffered formalin after excision of samples from standard sites in the thoracic and abdominal aorta for histological examination and lipid composition and synthesis studies. After fixation, the whole aortas are stained with Sudan IV and pinned out flat, and digital images are obtained with a TV camera connected to a computerized image analysis system (Image Pro Plus; Media Cybernetics, Silver Spring, Md.) to determine the percentage of aortic surface involved with atherosclerotic lesions [Gerrity R G et al, *Diabetes* (2001) 50:1654-65; Cornhill J F et al, *Arteriosclerosis, Thrombosis, and Vascular Biology* (1985) 5:415-26; which disclosures are hereby incorporated by reference in their entirety]. Comparison is made between groups of the percentage of aortic surface involved with atherosclerotic lesions.

Reduction of the percentage of aortic surface involved with atherosclerotic lesions on administration of the compound is taken as indicative of the compound having the aforesaid utility.

Example 6

Receptor Binding Assay

In addition to the methods described herein, another means for evaluating a test compound is by determining binding affinities to the RUP25 receptor. This type of assay generally requires a radiolabelled ligand to the RUP25 receptor. Absent the use of known ligands for the RUP25 receptor and radiolabels thereof, compounds of Formula (I) can be labelled with a radioisotope and used in an assay for evaluating the affinity of a test compound to the RUP25 receptor.

A radiolabelled RUP25 compound of Formula (I) can be used in a screening assay to identify/evaluate compounds. In general terms, a newly synthesized or identified compound (i.e., test compound) can be evaluated for its ability to reduce binding of the "radiolabelled compound of Formula (I)" to the RUP25 receptor. Accordingly, the ability to compete with the "radio-labelled compound of Formula (I)" or Radiolabelled RUP25 Ligand for the binding to the RUP25 receptor directly correlates to its binding affinity of the test compound to the RUP25 receptor.

Assay Protocol for Determining Receptor Binding for RUP25:

A. RUP25 Receptor Preparation 293 cells (human kidney, ATCC), transiently transfected with 10 ug human RUP25 receptor and 60 ul Lipofectamine (per 15-cm dish), are grown in the dish for 24 hours (75% confluency) with a media change and removed with 10 ml/dish of Hepes-EDTA buffer (20 mM Hepes+10 mM EDTA, pH 7.4). The cells are centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) added. The membranes are vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 ul of assay buffer and 50 ul of Radiolabelled RUP25 Ligand. For nonspecific binding, 50 ul of assay buffer is added instead of 100 ul and an additional 50 ul of 10 uM cold RUP25 is added before 50 ul of Radiolabelled RUP25 Ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For compound competition studies, instead of adding 100 ul of assay buffer, 100 ul of appropriately diluted test compound is added to appropriate wells followed by addition of 50 ul of Radiolabelled RUP25 Ligand.

C. Calculations

The test compounds are initially assayed at 1 and 0.1 µM and then at a range of concentrations chosen such that the middle dose would cause about 50% inhibition of a Radio-RUP25 Ligand binding (i.e., $IC_{50}$). Specific binding in the absence of test compound ($B_O$) is the difference of total binding ($B_T$) minus non-specific binding (NSB) and similarly specific binding (in the presence of test compound) (B) is the difference of displacement binding ($B_D$) minus non-specific binding (NSB). $IC_{50}$ is determined from an inhibition response curve, logit-log plot of % $B/B_O$ vs concentration of test compound.

$K_i$ is calculated by the Cheng and Prustoff transformation:

$$K_i = IC_{50}/(1+[L]/K_D)$$

where [L] is the concentration of a Radio-RUP25 Ligand used in the assay and $K_D$ is the dissociation constant of a Radio-RUP25 Ligand determined independently under the same binding conditions.

D. Alternative Binding Assay Procedure $^3$H-Nicotinic acid binding competition assay.

CHO-K1 cells stably expressing the niacin receptor were used to make membrane for binding analysis. Cells were grown to ~80% confluence in growth medium (F-12 Kaighn's modified medium (ATCC, #30-2004) containing 10% FBS (GFBCO, #10438-026), 1 mg/ml G418 (GIBCO, #10131-027) and 1× Pen-Strep (Sigma P-0871), harvested by scraping, and centrifuged at 12 000×g, 40 Celsius, 10 minutes. Cell pellets were resuspended in harvest buffer (20 mM HEPES, 10 mM EDTA, pH 7.4) and homogenized with 4×10 second bursts of a 12 mm Polytron homogenizer, setting 5. Lysate was centrifuged at 2 000×g, 4°, 10 minutes to remove unlysed cells and nuclei, and the resulting supernatant centrifuged at 39 000×g, 4°, 45 minutes to pellet membranes. The resulting pellet was resuspended in wash buffer (20 mM HEPES, 0.1 mM EDTA, pH 7.4), homogenized with 3×10 second bursts of a 12 mm Polytron, setting 4, and re-centrifuged at 39 000×g, 40, 45 minutes. The resulting pellet was resuspended in wash buffer and stored in liquid nitrogen before use. The concentration of membrane proteins in this preparation was determined using the Pierce BCA protein assay, with BSA as a standard.

Equilibrium binding of $^3$H-nicotinic acid was performed in 96-well polypropylene plates. Reactions contained 140 µl membrane diluted in assay buffer (20 mM HEPES, pH 7.4, 1 mM MgCl2, and 0.01% CHAPS; 15-30 µg membrane protein/assay), 20 µl test compounds diluted in assay buffer (compound stocks were in 100% DMSO; final DMSO concentration in the assay was 0.25%), and 40 µl 250 nM tritiated niacin ([5,6-$^3$H]—nicotinic acid: American Radiolabeled Chemicals, Inc., 20 µM in ethanol; final ethanol concentration in each assay was 1.5%). Non-specific binding was determined in the presence of 250 µM unlabeled nicotinic acid. After mixing at 3-4 hours at room temperature, reactions were filtered through Packard Unifilter GF/C plates using a Packard Harvester, and washed with 8×200 µl ice-cold binding buffer. Plates were dried overnight and their backs sealed using PerkinElmer tape designed for GF/C plates. 40 µl PerkinElmer Microscint-20 scintillation fluid was added to each well, the tops sealed, and plates analyzed in a Packard Top-Count scintillation counter.

Caluclations were preformed as in C above.

Certain compounds of the invention have an $EC_{50}$ in the $^3$H-nicotinic acid binding competition assay within the range of about 10 to about 100 µM. More advantageous compounds of the invention have an $EC_{50}$ value in this assay within the range of about 1 to about 10 µM. Still more advantages compounds have an $EC_{50}$ value in this assay of less than about 1 uM.

Example 7

Flushing via Laser Doppler

Procedure—Male C57B16 mice (~25 g) are anesthetized using 10 mg/ml/kg Nembutal sodium. When antagonists are to be administered they are co-injected with the Nembutal anesthesia. After ten minutes the animal is placed under the laser and the ear is folded back to expose the ventral side. The laser is positioned in the center of the ear and focused to an intensity of 8.4-9.0 V (with is generally ~4.5 cm above the ear). Data acquisition is initiated with a 15 by 15 image format, auto interval, 60 images and a 20 sec time delay with a medium resolution. Test compounds are administered following the 10th image via injection into the peritoneal space. Images 1-10 are considered the animal's baseline and data is normalized to an average of the baseline mean intensities. Materials and Methods—Laser Doppler Pirimed Piml; Niacin (Sigma); Nembutal (Abbott labs).

Example 8

Inhibition of Free Fatty-Acid Production, in vivo, in Catheterized Male Sprague-Daly Rats Non-esterified free-fatty acid (NEFA) assays were done on serum derived from live, freely moving rats. Jugular vein catheters were surgically implanted into the jugular veins and the animals were allowed to recover at least 48 hr post surgery. Food was removed from the animals approximately 16 hours prior to the assay. A draw of ~200 µl blood was pulled from the catheter and represents the baseline NEFA serum sample. Drug was administered intra-peritoneally (IP) at various concentrations to individual rats and then ~200 µl blood draws were pulled from the catheter at the indicated time points for further NEFA analysis. NEFA assays were performed according to the manufacturer's specifications (Wako Chemicals, USA; NEFA C) and free fatty acid concentrations were determined via regression analysis of a known standard curve (range of known free fatty acids). Data was analyzed using Excel and PrismGraph.

Example 9

The invention will now be illustrated by the following non-limiting examples in which, unless stated otherwise:

(i) all operations were carried out at room or ambient temperature, that is, at a temperature in the range 18-25° C.;

(ii) evaporation of solvent was carried out using a rotary evaporator under reduced pressure (4.5-30 mmHg) with a bath temperature of up to 50° C.;

(iii) the course of reactions was followed by thin layer chromatography (TLC) and/or tandem high performance liquid chromatography (HPLC) followed by mass spectroscopy (MS), herein termed LCMS, and any reaction times are given for illustration only;

(iv) the structure of all final compounds was assured by at least one of the following techniques: MS or proton nuclear magnetic resonance ($^1$H NMR) spectrometry, and the purity was assured by at least one of the following techniques: TLC or HPLC;

(v) yields, if given, are for illustration only;

(vi) $^1$H NMR spectra were recorded on either a Bruker Avance-400 or a Varian Unity or a Varian Inova instrument at 400 or 500 or 600 MHz using the indicated solvent; when line-listed, NMR data is in the form of delta ($\delta$) values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad;

(vii) MS data were recorded on a Waters Micromass unit or API 150EX, interfaced with a Hewlett-Packard (Agilent 1100) or Shimadzu (LC-10AD VP) HPLC instrument, and operating on MassLynx/OpenLynx or Analyst 1.2 software; electrospray ionization was used with positive (ES+) or negative ion (ES−) detection; the method for LCMS ES+ was 1-2 mL/min, 10-95% B linear gradient over 5.5 min (B=0.05% TFA-acetonitrile, A=0.05% TFA-water), and the method for LCMS ES− was 1-2 mL/min, 10-95% B linear gradient over 5.5 min (B=0.1% formic acid-acetonitrile, A=0.1% formic acid-water), Waters XTerra C18-3.5 um-50×3.0 mmID and diode array detection;

(viii) the purification of compounds by preparative reverse phase HPLC (RPHPLC) was conducted on either a Waters Symmetry Prep C18-5 um-30×100 mmID, or a Waters Atlantis Prep dC18-5 um-20×100 mmID; 20 mL/min, 10-100% B linear gradient over 15 min (B=0.05% TPA-acetonitrile, A=0.05% TFA-water), and diode array detection;

(ix) the automated purification of compounds by preparative reverse phase HPLC was performed on a Gilson system using a YMC-Pack Pro C18 column (150×20 mm i.d.) eluting at 20 mL/min with 0-50% acetonitrile in water (0.1% TFA);

(x) the purification of compounds by preparative thin layer chromatography (PTLC) was conducted on 20×20 cm glass prep plates coated with silica gel, or centrifugal chromatography on a chromatotron using glass rotors coated with silica gel, both commercially available from Analtech;

(xi) column chromatography was carried out on a silica gel column using Kieselgel 60, 0.063-0.200 mm (Merck).

(xii) microwave irradiations were carried out using the Smith Synthesizer (Personal Chemistry).

(xiii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), $IC_{50}$ (molar concentration which results in 50% of maximum possible inhibition), $EC_{50}$ (molar concentration which produces 50% of the maximum possible efficacy or response), uM (micromolar), nM (nanomolar).

The following examples are provided so that the invention might be more fully understood. They should not be construed as limiting the invention in any way.

Example 9.1

3-(2H-Tetrazol-5-yl)-1,4,5,6-tetrahydro-cyclopentapyrazole (Compound 1)

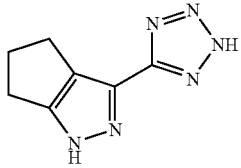 [SMILES: C1Cc2[nH]nc(-c3nn[nH]n3)c2C1]

Method A: Preparation of Compound 1.

1,4,5,6-Tetrahydro-cyclopentapyrazole-3-carbonitrile (0.022 g, 0.165 mmol) and sodium azide (0.086 g, 1.30 mmol) were taken up in DMF (3 cm³) at heated under microwave irradiation to 175° C. for 20 minutes. The solution was cooled to room temperature, filtered and the filtered solid washed with ethyl acetate. The combined solutions was added to saturated aqueous sodium bicarbonate (20 cm³) and washed with ethyl acetate. The aqueous layer was acidified to pH 1 with the addition of 1M aqueous hydrochloric acid and extracted into ethyl acetate. The ethyl acetate washes were combined and solvent removed under reduced pressure, the resulting solid purified by preparative HPLC to give 3-(2H-tetrazol-5-yl)-1,4,5,6-tetrahydro-cyclopentapyrazole as a white solid (0.012 g, 0.068 mmol, 41%). $^1$H NMR δ (CD$_3$OD): 2.88 (t-like, 2H, J=7.0), 2.82 (t-like, 2H, J=7.3), 2.64 (quintet-like, 2H, J=7.1); m/z (ES+): 177 [M+H]$^+$.

The intermediate 1,4,5,6-Tetrahydro-cyclopentapyrazole-3-carbonitrile was prepared using the following procedure.

Step A: 1,4,5,6-Tetrahydro-cyclopentapyrazole-3-carboxylic acid ethyl ester

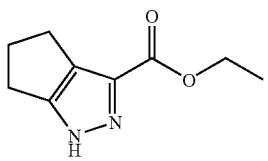

Cyclopentanone (10.0 g, 118.9 mmol) was taken up in absolute ethanol (30 cm³) and sodium ethoxide (53 cm³, 21% in ethanol, 143 mmol) was added. The resulting solution was stirred under argon for 10 minutes, then diethyl oxalate (19.1 g, 131 mmol) added. Further ethanol (10 cm³) was added and the solution heated at 75° C. for 3 hours and cooled to room temperature. Hydrazine hydrochloride (8.15 g, 119 mmol), taken up in water (20 cm³) was added and the solution heated to 75° C. overnight. Solvent was removed under reduced pressure and the resulting taken up in ethyl acetate (200 cm³) and washed with water (200 cm³), dried (Na$_2$SO$_4$), filtered and solvent removed under reduced pressure to give 1,4,5,6-tetrahydro-cyclopentapyrazole-3-carboxylic acid ethyl ester as an off white solid (16.16 g, 90.0 mmol, 76%). δ$_H$ (CD$_3$OD): 4.34 (q, 2H, J=7.1, OCH$_2$CH$_3$), 2.78 (t like, 2H, J=7.0), 2.72 (br s, 2H), 2.49 (br s, 2H), 1.36 (t, 3H, J=7.1, OCH$_2$CH$_3$). m/z (ES): 181 [M+H]$^+$.

Step B: 1,4,5,6-Tetrahydro-cyclopentapyrazole-3-carboxylic acid amide.

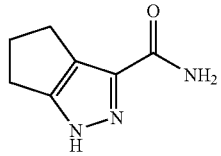 [SMILES: NC(=O)c1n[nH]c2c1CCC2]

1,4,5,6-Tetrahydro-cyclopentapyrazole-3-carboxylic acid ethyl ester (0.808 g, 4.48 mmol) was taken up in methanolic ammonia (ca 7 M, 12 cm³) and stirred overnight at 95° C. The resulting solution was chilled and the precipitated 1,4,5,6-tetrahydro-cyclopentapyrazole-3-carboxylic acid amide collected by vacuum filtration as a white crystalline solid (0.438 g, 2.90 mmol, 65%). δ$_H$ (CD$_3$OD): 2.79 (t like, 2H, J=6.9), 2.73 (t like, 2H, J=7.3), 2.55 (br s, 214); m/z (ES$^+$): 152 [M+H]$^+$.

Step C: 1,4,5,6-Tetrahydro-cyclopentapyrazole-3-carbonitrile.

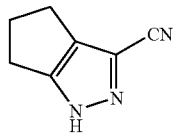

1,4,5,6-Tetrahydro-cyclopentapyrazole-3-carboxylic acid amide (0.210 g, 1.39 mmol) was added to anhydrous acetonitrile (12 cm³), heated to 80° C. and sodium chloride (2.0 g, 34-mmol) added. After 15 minutes phosphorus oxychloride (0.128 g, 0.83 mmol) was added and the solution heated to 80° C. overnight, cooled, filtered, and the collected solid washed with acetonitrile. Solvent was removed from the combined solutions under reduced pressure and the resulting solid purified by preparative HPLC to give 1,4,5,6-tetrahydro-cyclopentapyrazole-3-carbonitrile as a deep purple coloured solid (0.031 g, 0.23 mmol, 17%). δ$_H$ (CD$_3$OD): 2.79 (t like, 2H, J=7.3), 2.73 (t like, 2H, J=7.1), 2.65-2.55 (m, 2H); m/z (ES$^+$): 134 [M+H]$^+$.

Method B: Preparation of Compound 1.

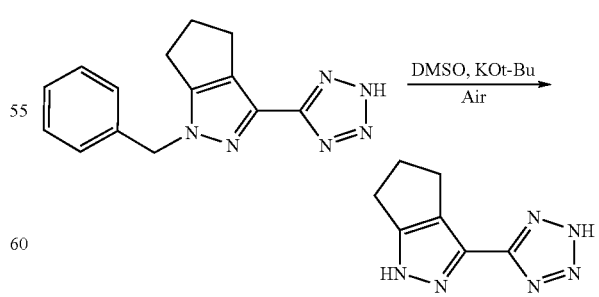

Air was bubbled through a stirring solution of 1-benzyl-3-(2H-tetrazol-5-yl)-1,4,5,6-tetrahydro-cyclopentapyrazole (1.92 g, 7.21 mmol) and KOt-Bu (65 mL of a 1M solution in THF) in DMSO (50 mL) for a period of 2.0 h. The reaction was acidified to pH=2 by the addition of HCl (3M aq). The mixture was filtered and the filtrate was concentrated in vacuo to remove volatiles. The material was purified by reverse-phase HPLC: Phenomenex® Luna C18 column (10μ, 250×50 mm), 5% (v/v) CH$_3$CN (containing 1% v/v TFA) in H$_2$O (containing 1% v/v TFA) gradient to 50% H$_2$O, 60 ml/min, λ=214 nm. The product was further purified by loading material on a Varian BondElut® 60 mL, 10 g SCX cartridge. MeOH (150 mL) was passed through the column to remove unbound impurities. The product was then eluted by passing a solution of 2N NH$_3$ in MeOH (150 mL) through the column. Concentration of the eluant yielded the ammonium salt of Compound 1 (947 mg, 5.38 mmol, 75% yield) as a white solid. $^1$H NMR (ammonium salt, 400 MHz, CD$_3$OD): δ 2.88 (2H, t, J=6.8 Hz), 2.74 (2H, t, J=6.8 Hz), 2.52 (2H, quin, J=6.8 Hz). HPLC/MS: Discoverye® C18 column (5μ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=1.22 min, ESI$^+$=177.3 (M+H). Anal Calcd for C$_7$H$_8$N$_6$ (neutral compound): C, 47.72; H, 4.58. Found: C, 47.27; H, 4.16. Anal Calcd for C$_7$H$_{11}$N$_7$ (ammonium salt): C, 43.51; H, 5.74. Found: C, 42.94; H, 5.30.

The intermediate 1-benzyl-3-(2H-tetrazol-5-yl)-1,4,5,6-tetrahydro-cyclopentapyrazole was prepared using the following procedure.

Step A: Preparation of 1-Benzyl-1,4,5,6-tetrahydro-cyclopentapyrazole-3-carboxylic acid amide and 2-Benzyl-2,4,5,6-tetrahydro-cyclopentapyrazole-3-carboxylic acid amide

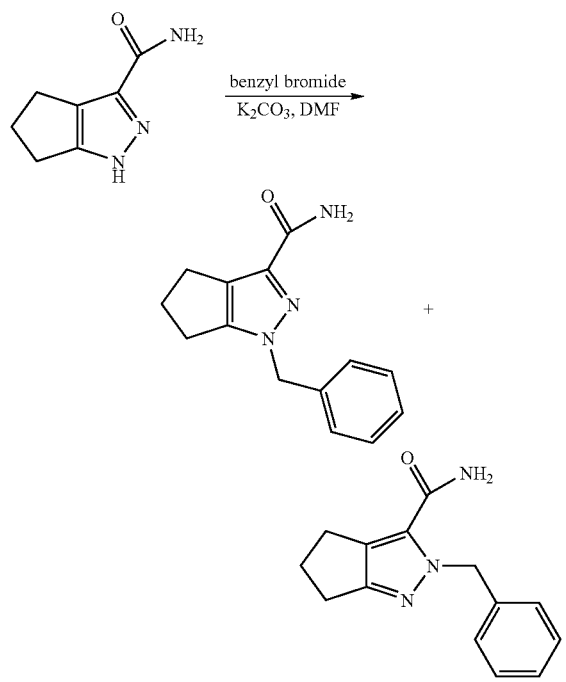

To a stirring solution of 1,4,5,6-tetrahydro-cyclopentapyrazole-3-carboxylic acid amide (2.57 g, 17.0 mmol) in DMF (34 mL) at 25° C. was added K$_2$CO$_3$ (5.87 g, 42.5 mmol) followed by benzyl bromide (4.36 g g, 25.5 mmol). The reaction was stirred at ambient temperature for 16 h at which time the mixture was diluted with EtOAc (75 mL) and filtered. The filtrate was washed with H$_2$O (100 mL) and the aqueous phase was back-extracted with EtOAc (75 mL) and CH$_2$Cl$_2$ (75 mL). The combined organic extracts were dried over MgSO$_4$, filtered, and concentrated in vacuo. Purification by silica gel chromatography (50% EtOAc in hexanes gradient to 95% EtOAc in hexanes) gave 2-benzyl-2,4,5,6-tetrahydro-cyclopentapyrazole-3-carboxylic acid amide (739 mg, 3.07 mmol, 18% yield) isolated as a white solid followed by 1-benzyl-1,4,5,6-tetrahydro-cyclopentapyrazole-3-carboxylic acid amide (3.24 g, 13.4 mmol, 79% yield) isolated as a white solid.

1-Benzyl-1,4,5,6-tetrahydro-cyclopentapyrazole-3-carboxylic acid amide $^1$H NMR (400 MHz, CDCl$_3$): δ 7.37-7.30 (3H, m), 7.19 (2H, m), 6.67 (1H, bs), 5.34 (1H, bs), 5.19 (2H, s), 2.82 (2H, m), 2.51 (4H, m). $^{13}$C APT NMR (100 MHz, CDCl$_3$): δ up: 164.8, 155.2, 139.0, 136.0, 129.5, 55.3, 31.2, 24.1; down: 129.0, 128.3, 127.8. HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.13 min, ESI$^+$=242.2 (M+H).

2-Benzyl-2,4,5,6-tetrahydro-cyclopentapyrazole-3-carboxylic acid amide $^1$H NMR (400 MHz, CDCl$_3$): δ 7.34-7.21 (5H, m), 5.76 (2H, s), 5.70-5.38 (2H, bs), 2.78 (4H, m), 2.49 (2H, m). $^{13}$C APT NMR (100 MHz, CDCl$_3$): δ up: 161.9, 160.1, 138.3, 128.3, 127.1, 55.1, 29.9, 24.8, 24.7; down: 128.6, 128.0, 127.6. HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.98 min, ESI$^+$=242.1 (M+H).

Step B: Preparation of 1-Benzyl-3-(2H-tetrazol-5-yl)-1,4,5,6-tetrahydro-cyclopentapyrazole

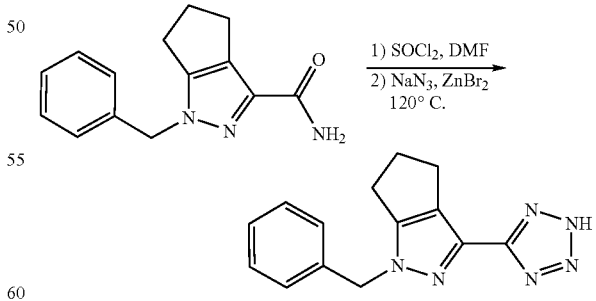

To a solution of 1-benzyl-1,4,5,6-tetrahydro-cyclopentapyrazole-3-carboxylic acid amide (3.02 g, 12.53 mmol) in DMF (25 mL) at rt was added thionyl chloride (1.94 g, 16.3 mmol). The reaction was stirred for 18 h at which time NaHCO$_3$ (sat. aq., 6 mL) was added to quench excess thionyl chloride. The mixture was diluted with EtOAc (150 mL) and washed sequentially with NaHCO₃ (sat. aq., 100 mL) and brine (100 mL). The aqueous washes were back-extracted with EtOAc (2×100 mL) and the combined organics were dried over MgSO₄, filtered, and concentrated in vacuo to yield a crude yellow oil.

The concentrate was dissolved in DMF (20 mL) and placed in a heavy walled sealed reaction vessel at which time to which ZnBr₂ (4.70 g, 18.0 mmol) and NaN₃ (2.73 g, 42.0 mmol) were added sequentially. The vessel was sealed and heated to 120° C. for 18 h. The mixture was cooled to rt and HCl (3M aq., 2 mL) was added and stirring was continued for 5 min. The mixture was diluted with EtOAc (150 mL) and washed with HCl (1M, aq., 100 mL). The organics were dried over MgSO₄, filtered, and concentrated. Purification by silica gel chromatography (50:50:0.2, hexanes:EtOAc:AcOH gradient to 100:0.2, EtOAc:AcOH) gave 1-benzyl-3-(2H-tetrazol-5-yl)-1,4,5,6-tetrahydro-cyclopentapyrazole (2.06 g, 7.74 mmol, 62% yield) as a white solid. $^1$H NMR (400 MHz, CD₃OD): δ 7.36-7.25 (5H, m), 5.30 (2H, s), 2.84 (2H, t, J=6.4 Hz), 2.62-2.56 (4H, m). $^{13}$C APT NMR (100 MHz, CD₃OD): δ up: 153.8, 151.9, 137.6, 131.5, 128.9, 55.8, 31.9, 24.8, 24.6; down: 129.9, 129.1, 129.0. HPLC/MS: Discovery® C18 column (5μ, 50×2.1 mm), 5% v/v CH₃CN (containing 1% v/v TFA) in H₂O (containing 1% v/v TFA) gradient to 99% v/v CH₃CN in H₂O, 0.75 mL/min, t$_r$=2.18 min, ESI$^+$=267.1 (M+H).

Method C: Preparation of Compound 1.

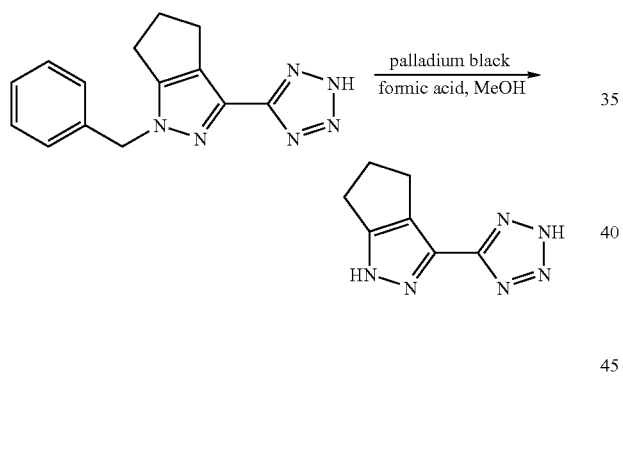

To a solution of 1-benzyl-3-(2H-tetrazol-5-yl)-1,4,5,6-tetrahydro-cyclopentapyrazole (59.4 g, 223 mmol) in 10% formic acid/MeOH (vol/vol, 900 mL) was added palladium black (39.8 g, 374 mmol). The mixture was mechanically stirred under N₂ atmosphere for 24 h. The reaction was filtered and concentrated. The product was further purified and converted to the ammonium salt by the following by loading material (as a solution in MeOH) on to a column containing Bondesil SCX SPE resin (750 g). The column was flushed with MeOH (2.0 L) to remove unbound impurities. The product was eluted using 2N NH₃/MeOH (approx. 1.5 L). Upon concentration the ammonium salt of the tetrazole (39.3 g, 203 mmol, 91% yield) was obtained as a white solid.

The intermediate 1-benzyl-3-(2H-tetrazol-5-yl)-1,4,5,6-tetrahydro-cyclopentapyrazole was prepared using the following procedure.

Step A: Preparation of 1,4,5,6-Tetrahydro-cyclopentapyrazole-3-carboxylic acid ethyl ester

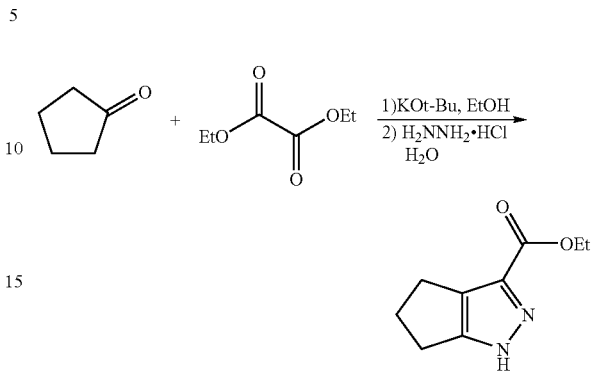

To a solution of cyclopentanone (42.0 g, 0.50 mol) and diethyl oxalate (73.1 g, 0.50 mol) in EtOH (2.5 L) at rt under N₂ was added a solution of KOt-Bu in THF (500 mL of a 1M solution, 0.50 mol) over 0.5 h via an addition funnel. The reaction was stirred for 3.5 h at which time the flask was cooled to 0° C. Hydrazine hydrochloride (37.6 g, 0.55 mol) in H₂O (250 mL) was added via addition funnel over 0.5 h. The reaction was warmed to rt and stirred for 16 h. The volatiles were removed in vacuo and the resulting solid was washed with NaHCO₃ (sat. aq., 500 mL) and H₂O (500 mL). Further concentration in vacuo gave pure 1,4,5,6-tetrahydro-cyclopentapyrazole-3-carboxylic acid ethyl ester (63.6 g, 0.35 mol, 71% yield) as a yellow solid.

Step B: Preparation of 1,4,5,6-tetrahydro-cyclopentapyrazole-3-carboxylic acid amide

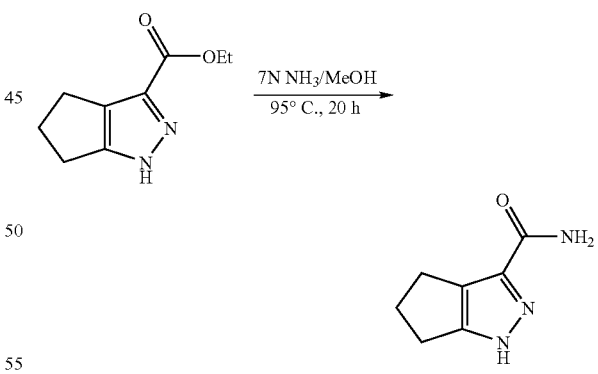

1,4,5,6-Tetrahydro-cyclopentapyrazole-3-carboxylic acid ethyl ester (63.5 g, 0.35 mmol) was dissolved in a solution of 7N NH₃MeOH (1.0 L). The solution was divided into four equal portions each of which was transferred to 350 mL heavy-walled sealed reaction vessel. The vessels were heated to 95° C. and stirred for 20 h. The reactions were cooled to rt at which time a solid precipitated. The solution was filtered and the solid was washed with NaOH (1N aq., 200 mL) giving pure 1,4,5,6-tetrahydro-cyclopentapyrazole-3-carboxylic acid amide (42.0 g, 0.20 mol, 80% yield) as a white solid.

Step C: Preparation of 1-Benzyl-1,4,5,6-tetrahydro-cyclopentapyrazole-3-carboxylic acid amide and 2-Benzyl-1,4,5,6-tetrahydro-cyclopentapyrazole-3-carboxylic acid amide

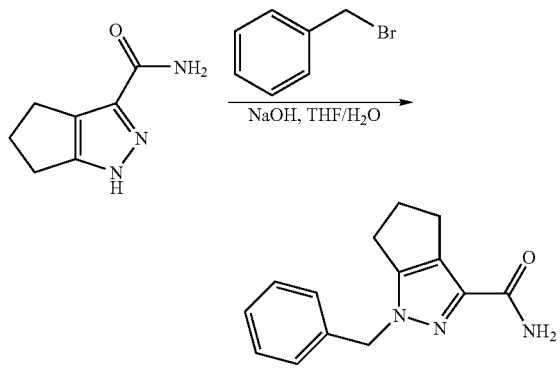

To a solution of 1,4,5,6-tetrahydro-cyclopentapyrazole-3-carboxylic acid amide (41.5 g, 275 mmol) in THF (460 mL) at rt was added a solution of NaOH (5N aq., 110 mL, 0.54 mol). After stirring for 5 min benzyl bromide (49.2 g, 0.29 mol) was added and the reaction was stirred for 16 h. The volatiles were removed in vacuo and the resulting solid was washed with H₂O (3×250 mL). Further concentration gave regioisomers of 1-benzyl-1,4,5,6-tetrahydro-cyclopentapyrazole-3-carboxylic acid amide and 2-benzyl-1,4,5,6-tetrahydro-cyclopentapyrazole-3-carboxylic acid amide (65.3 g, 270 mmol, 98% yield) as a 20:1 mixture and was used without separation).

Step D: Preparation of 1-Benzyl-3-(2H-tetrazo-5-yl)-1,4,5,6-tetrahydro-cyclopentapyrazole

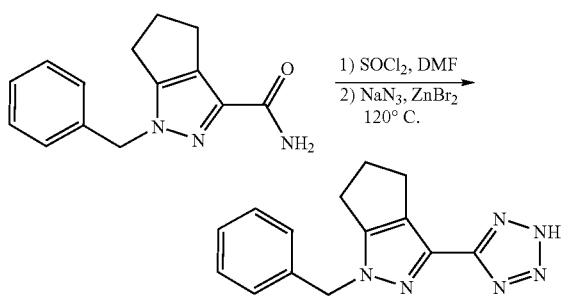

A flask equipped with a drying tube under N₂ atmosphere was charged with anhydrous DMF (250 mL). The flask was cooled to 0° C. and thionyl chloride (36.7 g, 309 mmol) was added via syringe over a period of 5 min. After stirring for an additional 10 min, a solution of 1-benzyl-1,4,5,6-tetrahydro-cyclopentapyrazole-3-carboxylic acid amide (67.7 g, 281 mmol) in DMF (310 mL) was added over 5 min using an addition funnel. The mixture was slowly warmed to rt and stirred for 16 hr. NaHCO₃ (sat. aq., 100 mL) was added and the mixture was stirred for 10 min. The volatiles were removed in vacuo and the residue was diluted with EtOAc (700 mL) and NaHCO₃ (sat. aq., 700 mL). The layers were separated and the aqueous phase was back-extracted with EtOAc (400 mL). The combined organics were washed with NaHCO₃ (sat. aq., 600 mL) and brine (600 mL), dried over MgSO₄, filtered, and concentrated to give 63.1 g of nitrile as a brown solid.

To a solution of the nitrile (from above) in DMF (560 mL) was added ZnBr₂ (95.6 g, 425 mmol) followed by NaN₃ (55.2 g, 849 mmol). The mixture was heated to 120° C. and stirred for 14 h. The reaction was cooled to rt and the DMF was removed in vacuo. HCl (2N aq., 800 mL) was added and the mixture was stirred for 15 min followed by filtration. The solid was added to a biphasic mixture of EtOAc (500 mL) and HCl (5N aq., 300 mL) and stirred for 0.5 h. The solution was filtered and the layers separated. The remaining solid was again treated with EtOAc and HCl (5N aq.) as described above and this process (stir, filter, separate) was repeated until all solid material was dissolved. The combined organic filtrates were concentrated to give 1-benzyl-3-2H-tetrazol-5-yl)-1,4,5,6-tetrahydro-cyclopentapyrazole (61.0 g, 229 mmol, 81% yield from the amide) as a light brown solid.

Example 9.2

3-(1H-Tetrazol-5-yl)-2,6-dihydro-4H-thieno[3,4-c]pyrazole (Compound 2)

Compound 2 was prepared in a similar manner as described in Example 9.1, and was characterized by NMR and MS; ¹H NMR (400 MHz, MeOD): (400 MHz, CD₃OD) δ4.11 (dd, J=4.0, 2.2 Hz, 2 H), 4.03 (dd, J=3.6, 2.2 Hz, 2 H). HPLC/MS: Waters® YMC ODS-A C18 column (5µ, 50×4.6 mm), 5% v/v CH₃CN (containing 1% v/v TFA) in H₂O (containing 1% v/v TFA) gradient to 99% v/v CH₃CN in H₂O, 3.5 mL/min, t,=1.27 min, ESI+=194 (M+H).

Example 9.3

6-Methyl-3-(1H-tetrazol-5-yl)-2,6-dihydro-4H-furo[3,4-c]pyrazole (Compound 3)

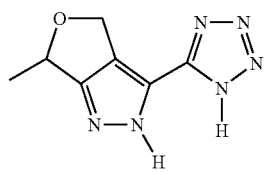

Compound 3 was prepared in a similar manner as described in Example 9.1, a separation by column chramoatography of the regioisomers was performed after the formation of the pyrazole.

Compound 3 was characterized by NMR and MS; ¹H NMR (400 MHz, DMSO): δ 5.20 (m, 1H), 4.94 (dd, J=34.7, 10.3 Hz, 2 H), 1.39 (d, J=4.4 Hz, 3 H). HPLC/MS: Alltech® Prevail C18 column (5µ, 50×4.6 mm), 5% v/v CH₃CN (containing 1% v/v TFA) in H$_2$O (containing 1% v/v TFA) gradient to 99% v/v CH$_3$CN in H$_2$O, 3.5 mL/min, t$_r$=1.03 min, ESI+=192 (M+H).

Example 9.4

3-(1H-Tetrazol-5-yl)-1,4-dihydro-cyclopentapyrazole (Compound 4) and 3-(1H-Tetrazol-5-yl)-1,6-dihydro-cyclopentapyrazole (Compound 5)

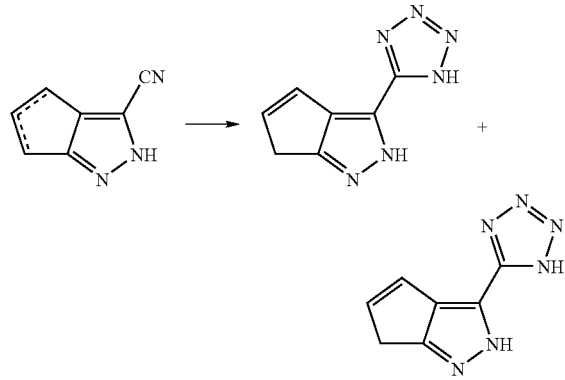

Compound 9.4A

A solution of Compound 9.4A, as an isomeric mixture, (50 mg, 0.38 mmol), sodium azide (86.5 mg, 1.33 mmol) and zinc bromide (300 mg, 1.33 mmol) in DMF (2 mL) was irradiated under microwave at 200° C. for 6 hours. After cooling to room temperature, the reaction mixture was treated with a 2 N HCl solution, extracted with EtOAc, washed with H$_2$O and concentrated in vacuo. HPLC separation (C18 column, 5 to 99% CH$_3$CN in H$_2$O) afforded 40.3 mg (61%) of the desired product as a 2:1 mixture of olefinic isomers. LC-MS m/z 175 (M+1); $^1$H NMR (400 MHz, DMSO-d$_6$) δ 6.94 (m, 0.5 H), 6.87 (m, 1 H), 6.76 (m, 1 H), 6.40 (m, 0.5 H), 3.35 (m, 3 H).

The isomers were separated by reverse-phase HPLC: Phenomenex® Luna C18 column (10μ, 250×21.2 mm), 5% (v/v) CH$_3$CN (containing 1% v/v TFA) in H$_2$O (containing 1% v/v TFA) gradient to 70% H$_2$O, 20 m/min, λ=280 nm.

Alternatively the isomers were separated by normal-phase HPLC: Dynamax Micorsorb Si (prep) column (8μ, 250×10 mm), 80% (v/v) EtOAc (containing 2% v/v AcOH) in hexanes (containing 2% v/v AcOH) gradient to 99% EtOAc, 7.5 ml/min, λ=280 nm.

The order of isomer elution is the same for both normal- and reverse-phase columns.

Isomer 1 (High Rf Isomer):

$^1$H NMR (400 MHz, MeOD): δ 6.79 (2H, m), 3.42 (2H, m). HPLC/MS: Discovery® C18 column (5μ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=1.10 min, ESI$^+$=174.9 (M+H).

Isomer 2 (Low Rf Isomer):

$^1$H NMR (400 MHz, MeOD): δ 6.98 (1H, m), 6.44 (1H, m), 3.33 (2H, m). HPLC/MS: Discovery® C18 column (5μ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=1.11 min, ESI$^+$=175.1 (M+H).

The intermediate Compound 9.4A, as an isomeric mixture, was prepared using the following steps:

Step A: Preparation of 2,6-Dihydro-cyclopentapyrazole-3-carboxylic acid ethyl ester and 2,4-Dihydro-cyclopentapyrazole-3-carboxylic acid ethyl ester (mixture)

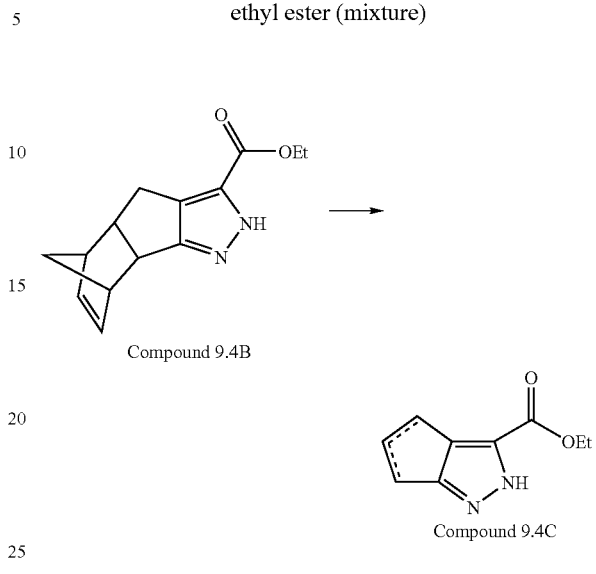

Compound 9.4B was prepared from the corresponding ketone using a similar method as described herein for the preparation of pyrazole esters (see Example 14.2). A solution of Compound 9.4B (2.0 g, 8.19 mmol) in phenyl ether (25 mL) was heated at reflux (250~260° C.) under nitrogen for 2 hours.

After cooling down the solution to room temperature, it was loaded on a SiO$_2$ column, flushed with DCM to push out the phenyl ether, and eluted with EtOAc/Hex (⅓) to afford 1.05 g (72%) of Compound 9.4C as a mixture of olefinic isomers. LC-MS m/z 179 (M+1).

Step B: Preparation of 2,6Dihydro-cyclopentapyrazole-3-carboxylic acid amide and 2,4-Dihydro-cyclopentapyrazole-3-carboxylic acid amide (mixture)

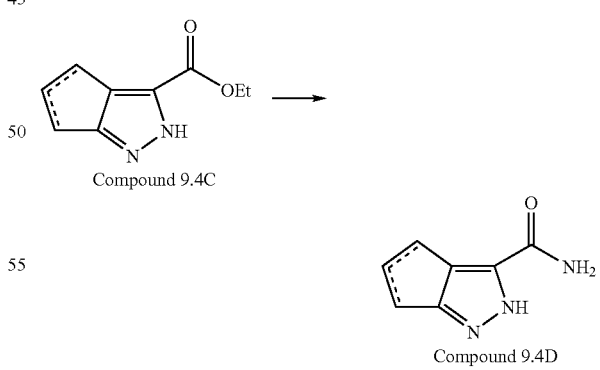

Compound 9.4C, as an isomeric mixture, (1.0 g, 5.61 mmol) was dissolved in smallest amount of dioxane (<5 mL) and mixed with 28% ammonium hydroxide solution (100 mL) in a tightly sealed container. The solution was stirred at room temperature for 24 hours and concentrated in vacuo to afford Compound 9.4D, as an isomeric mixture, as a solid in quantitative yield. LC-MS m/z 150 (M+1).

Step C: Preparation of
2,6-Dihydro-cyclopentapyrazole-3-carbonitrile and
2,4-Dihydro-cyclopentapyrazole-3-carbonitrile
(mixture)

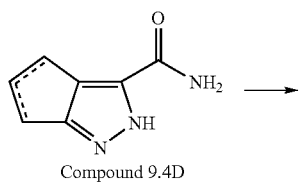

Compound 9.4D

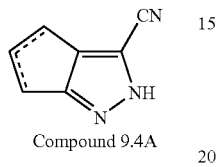

Compound 9.4A

To a suspension of Compound 9.4D, as an isomer mixture, (0.80 g, 5.36 mmol) and potassium carbonate (0.445 g, 3.22 mmol) in acetonitrile (30 mL) was added POCl$_3$ (0.785 mL, 8.58 mmol) at room temperature. The reaction mixture was heated at reflux for 2 hours. After concentration in vacuo, the residue was diluted with EtOAc (150 mL), washed with H$_2$O and brine, dried (Na$_2$SO$_4$), and concentrated to afford 141 mg (20%) of Compound 9.4A as an isomer mixture. LC-MS m/z 132 (M+1).

Example 9.5

3-(1H-Tetrazol-5-yl)-2,6-dihydro-4H-furo[3,4-c]pyrazole (Compound 6)

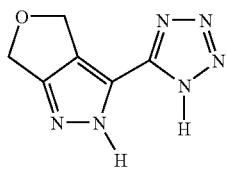

Compound 6 was prepared in a similar manner as described in Example 9.1, and was characterized by NMR and MS; LC-MS m/z 179 (M+1); $^1$H NMR (400 MHz, CD$_3$OD) δ 5.07 (t, J=2.2 Hz, 2 H), 4.92 (t, J=2.2 Hz, 2 H).

Example 9.6

5-Ethyl-3-(1H-tetrazol-5-yl)-2,4,5,6-tetrahydro-cyclopentapyrazole (Compound 7)

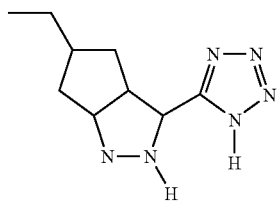

Compound 7 was prepared in a similar manner as described in Example 9.1, and was characterized by NMR and MS; $^1$H NMR (MeOD, 400 MHz): δ 3.07 (1H, dd, J=14.8, 7.6 Hz), 2.94-2.82 (2H, m), 2.51 (1H, dd, J=15.2, 6.8 Hz) 2.41 (1H, dd, J=13.6, 5.6 Hz), 1.6 (2H, m), 1.02 (3H, t, J=7.2 Hz). HPLC/MS: Discovery® C18 column (5μ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=1.42 min, ESI$^+$=205.2 (M+H).

Example 9.7

Preparation of Intermediate 1-Benzyl-5-hydroxy-1,4,5,6-tetrahydrocyclo-penta[c]pyrazole-3-carbonitrile

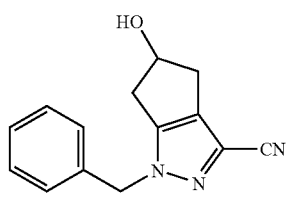 [SMILES: N#Cc1nn(Cc2ccccc2)c2c1CC(O)C2]

Step A: Preparation of 1-Benzyl-1,6-dihydro-cyclopentapyrazole-3-carboxylic acid ethyl ester and 1-Benzyl-1,4-dihydro-cyclopentapyrazole-3-carboxylic acid ethyl ester (mixture)

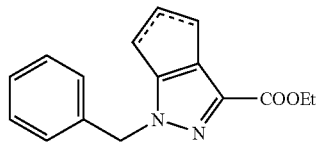

To a solution of the pyrazole (Compound 9.4C, see Example 9.4, Step A, 2.0 g, 11.22 mmol) in anhydrous THF (100 mL) was added benzyl bromide (5.36 mmol, 44.88 mmol) and NaOH (1.79 g, 44.88 mmol). After stirring at room temperature for 1 hour, the reaction was quenched with 1N HCl (100 mL). The resulting mixture was extracted with ethyl acetate, washed with 1N HCl, saturated NaHCO$_3$ solution, brine and dried over anhydrous Na$_2$SO$_4$. The solution was filtered and concentrated in vacuo. This material was purified on the biotage flash 40M column (SiO$_2$) using 30% ethyl acetate-hexanes. A colorless oil was obtained. LC-MS: 3.22 min; (M+Na)=291.1.

Step B: Preparation of 1-Benzyl-1,6-dihydro-cyclopentapyrazole-3-carboxylic acid and 1-Benzyl-1,4-dihydro-cyclopentapyrazole-3-carboxylic acid (mixture)

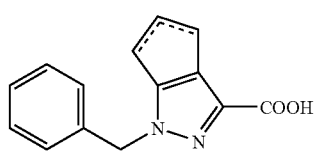

To a solution of the intermediate from step A (3.55 g, 13.23 mmol) in 1:1 THF/MeOH (40 mL) was added NaOH solution (5N, 3.9 mL, 20 mmol). After 3 hours at room temperature, the reaction was quenched by adding 1N HCl (22 mL). The aqueous layer was extracted with ethyl acetate (3×) dried over anhydrous Na₂SO₄, filtered and concentrated in vacuo. A yellow solid was obtained which was used in the next step without any further purification. LC-MS: 2.62 min; (M+H)=241.1.

Step C: Preparation of 1-Benzyl-1,6-dihydro-cyclopentapyrazole-3-carboxylic acid 2,5-dioxo-pyrrolidin-1-yl ester and 1-Benzyl-1,4-dihydro-cyclopentapyrazole-3-carboxylic acid 2,5-dioxo-pyrrolidin-1-yl ester (mixture)

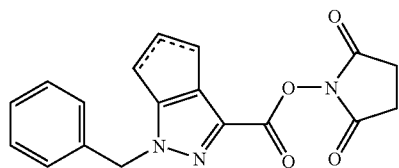

To a solution of the intermediate from step B (3.17 g, 13.23 mmol) in CH₂Cl₂ (200 mL) was added N-hydroxy succinimide (3.04 g, 26.46 mmol) followed by EDC (5.07 g, 26.46 mmol). After stirring the reaction mixture at room temperature for 18 hours, it was concentrated in vacuo. The residue was diluted with ethyl acetate (200 mL), washed with saturated NaHCO₃ solution and brine. The organic layer was dried over anhydrous Na₂SO₄, filtered and concentrated in vacuo. A yellow solid was obtained. LC-MS: 2.99 min; (M+H)=338.1.

Step D: Preparation of 1-Benzyl-1,6-dihydro-cyclopentapyrazole-3-carboxylic acid amide and 1-Benzyl-1,4-dihydro-cyclopentapyrazole-3-carboxylic acid amide (mixture)

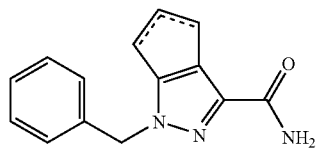

To a solution of the intermediate from step C (4.45 g, 13.22 mmol) in 1,4-dioxane (150 mL) was added NH₄OH (14.8 N, 10.0 eq, 9.1 mL). A precipitate formed immediately. After stirring at room temperature for 15 minutes the reaction mixture was filtered through a sintered funnel and the precipitate washed with 1,4-dioxane. The filtrate was concentrated in vacuo to give a yellow solid. LC-MS: 2.55 min; (M+H)=240.1.

Step E: Preparation of 1-Benzyl-1,6-dihydro-cyclopentapyrazole-3-carbonitrile and 1-Benzyl-1,4-dihydro-cyclopentapyrazole-3-carbonitrile (mixture)

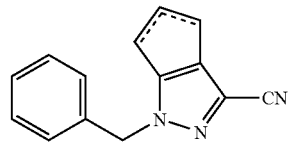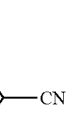

To a solution of the intermediate from step D in anhydrous DMF (50 mL) was added cyanuric chloride (2.33 g, 13.2 mmol). After stirring at room temperature for 15 minutes the reaction was quenched by pouring into water (100 mL). The resulting mixture was extracted with ethyl acetate, washed with saturated NaHCO₃, brine, dried over anhydrous Na₂SO₄, filtered and concentrated in vacuo. The residue was purified on the biotage flash 40 M column (SiO₂) using 20% ethyl acetate-hexanes. A white solid was obtained. LC-MS: 3.22 min; (M+H)=222.2.

Step F: Preparation of 1-Benzyl-5-hydroxy-1,4,5,6-tetrahydro-cyclopentapyrazole-3-carbonitrile

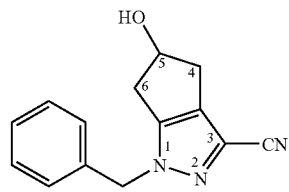 [SMILES: N#Cc1nn(Cc2ccccc2)c2c1CC(O)C2]

To a solution of the intermediate from step E (0.95 g, 4.29 mmol) in anhydrous THF (40 mL) cooled to 0° C. under a N₂ atmosphere was added Borane-THF (23 mmol, 5.36 eq, 1.0 M solution). The reaction was warmed to room temperature and stirred for 1 hour. The reaction was then cooled to 0° C. Water was added (3 mL) followed by NaOH (4.29 mmol, 1.43 mL, 3N) and H₂O₂ (12.88 mmol, 1.32 mL, 30% solution in water). After heating the reaction at 50° C. for 30 minutes, it was cooled to room temperature and quenched by the addition of water. The resulting mixture was extracted with ethyl acetate (3×). The organic layer was dried over anhydrous Na₂SO₄ filtered and concentrated in vacuo. The residue was purified by flash chromatography using 30% ethyl acetate-hexanes to give a 1:1 mixture of the C-5 and C-6 alcohols.

Less polar isomer (C-6 alcohol, Compound 17) ¹H NMR (500 MHz, CDCl₃): δ 7.2 (m, 5H), 5.35 (d, J=14.9 Hz, 1H), 5.31 (d, J=14.6 Hz, 1H), 4.99 (dd, J=3.4, 6.9 Hz, 1H), 2.9 (m, 2H), 2.6 (m, 1H), 2.35 (m, 1H). LC-MS: 2.76 min; (M+H)=240.1.

More polar isomer (C-5 alcohol) ¹H NMR (500 MHz, CDCl₃): δ 7.4-7.2 (m, 5H), 5.28 (d, J=14.8 Hz, 1H), 5.25 (d, J=14.9 Hz, 1H), 5.01 (m, 1H), 3.13 (dd, J=6.4, 15.8 Hz, 1H), 2.89 (dd, J=6.6, 16.2 Hz, 1H), 2.68 (dd, J=3.7, 16.0 Hz, 1H), 2.52 (dd, J=3.4, 16.2 Hz, 1H). LC-MS: 2.60 min; (M+H)=240.1.

Example 9.8

Preparation of Intermediate Trifluoro-methane-sulfonic acid 1-benzyl-3-cyano-1,6-dihydro-cyclopentapyrazol-5-yl ester and Trifluoro-methane-sulfonic acid 1-benzyl-3-cyano-1,4-dihydro-cyclopentapyrazol-5-yl ester as a regio-isomeric mixture

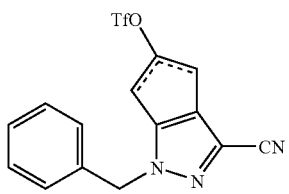

Step A: Preparation of (4-Ethoxy-2-oxo-cyclopent-3-enyl)-oxo-acetic acid tert-butyl ester

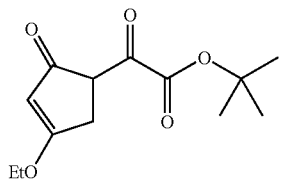 [SMILES: CCOC1=CC(=O)C(C(=O)C(=O)OC(C)(C)C)C1]

To a solution, of 3-ethoxy cyclopentenone (2.12 g, 16.82 mmol) in anhydrous THF (40 mL) cooled to −78° C. under a nitrogen atmosphere was added lithium diisopropyl amide (12 mL, 24 mmol, 2.0 M in THF). After 15 minutes, a solution of di-tert-butyl dioxalate (3.73 g, 18.5 mmol) in THF (15 mL) was added. The reaction mixture was stirred at −78° C. for 15 minutes and then warmed to −20° C. and stirred for an additional 15 minutes. The reaction was quenched with 1N HCl (40 mL) and extracted with ethyl acetate (3×). The organic layer was washed with brine, dried over anhydrous Na₂SO₄, filtered and concentrated in vacuo. The residue was purified by flash chromatography (SiO₂) using 35% ethyl acetate-hexanes to give the desired product (2.53 g) as an off-white solid.

Step B: Preparation of 1-Benzyl-5-oxo-1,4,5,6-tetrahydro-cyclopentapyrazole-3-carboxylic acid tert-butyl ester

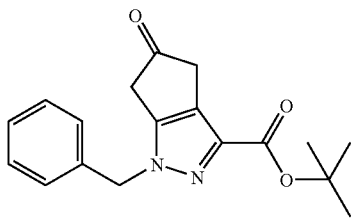 [SMILES: CC(C)(C)OC(=O)c1nn(Cc2ccccc2)c2c1CC(=O)C2]

To a solution of the intermediate from step A (2.15 g, 8.45 mmol) in ethanol (100 mL) was added benzyl hydrazine hydrochloride (1.8 g, 9.22 mmol) and HOAc (10 mL). The reaction mixture was stirred at room temperature for 16 hours and then refluxed at 70° C. for 30 minutes. The reaction was cooled to room temperature and concentrated in vacuo. The residue was dissolved in ethyl acetate and washed with water, saturated NaHCO₃, and brine. The organic layer was dried over anhydrous Na₂SO₄ filtered and concentrated in vacuo. The residue was purified by flash chromatography (SiO₂) using 30% ethyl acetate-hexanes to give the desired product (1.64 g) a brown oil.

Step C: Preparation of 1-Benzyl-5-oxo-1,4,5,6-tetrahydro-cyclopentapyrazole-3-carboxylic acid

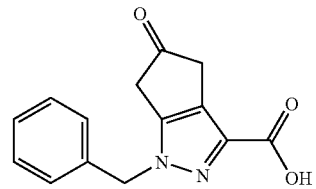 [SMILES: O=C1Cc2c(C(=O)O)nn(Cc3ccccc3)c2C1]

To a solution of the intermediate from step, B (1.64 g, 5.25 mmol) in dichloromethane (20 mL) was added trifluoroacetic acid (20 mL) and the resulting solution stirred at room temperature for 4 hours. The reaction mixture was concentrated in vacuo and azeotroped with toluene (3×). This material was carried on to the next step without any further purification.

Step D: Preparation of 1-Benzyl-5-oxo-1,4,5,6-tetrahydro-cyclopentapyrazole-3-carboxylic acid 2,5-dioxo-pyrrolidin-1-yl ester

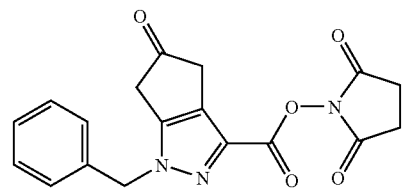 [SMILES: O=C1Cc2c(C(=O)ON3C(=O)CCC3=O)nn(Cc3ccccc3)c2C1]

To a solution of the intermediate from step C (1.34 g, 5.25 mmol) in CH₂Cl₂ (50 mL) was added N-hydroxy succinimide (1.21 g, 10.5 mmol) followed by EDC (2.01 g, 10.5 mmol). After stirring at room temperature for 18 hours, the reaction mixture was concentrated in vacuo. The residue was diluted with ethyl acetate (200 mL), washed with saturated NaHCO₃, solution and brine. The organic layer was dried over anhydrous Na₂SO₄, filtered and concentrated in vacuo. A yellow solid was obtained.

Step E: Preparation of 1-Benzyl-5-oxo-1,4,5,6-tetrahydro-cyclopentapyrazole-3-carboxylic acid amide

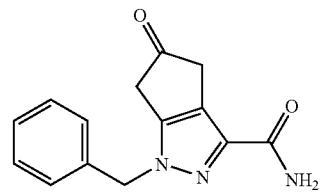 [SMILES: NC(=O)c1nn(Cc2ccccc2)c2c1CC(=O)C2]

To a solution of the intermediate from step D (2.0 g, 5.25 mmol) in 1,4-dioxane (50 mL) was added NH₄OH (14.8 N, 10.0 eq, 3.53 mL). A precipitate formed immediately. After stirring at room temperature for 15 minutes the reaction mixture was filtered through a fritted funnel and the precipitate washed with 1,4-dioxane. The filtrate was concentrated in vacuo to give a solid.

Step F: Preparation of 1-Benzyl-5-oxo-1,4,5,6-tetrahydro-cyclopentapyrazole-3-carbonitrile

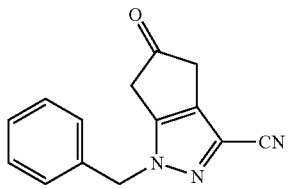 [SMILES: N#Cc1nn(Cc2ccccc2)c2c1CC(=O)C2]

To a solution of the intermediate from step E (5.25 mmol) in DMF (60 mL) was added cyanuric chloride (3.12 g, 17 mmol) in three portions. After 30 minutes at room temperature, the reaction was quenched with water and extracted with ethyl acetate (2×). The organic layer was washed with water, brine and dried over anhydrous $Na_2SO_4$, filtered, and concentrated in vacuo. The residue was purified by flash chromatography ($SiO_2$) using 30% ethyl acetate-hexanes to give the desired product (0.95 g) as a yellow solid.

Step G: Preparation of Trifluoro-methanesulfonic acid 1-benzyl-3-cyano-1,6-dihydro-cyclopentapyrazol-5-yl ester and Trifluoro-methanesulfonic acid 1-benzyl-3-cyano-1,4-dihydro-cyclopentapyrazol-5-yl ester (mixture)

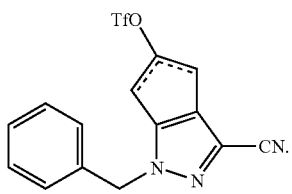

To a solution of the intermediate from step F (447 mg, 1.87 mmol) in anhydrous THF (14 mL) at −78° C. was added a solution of freshly prepared lithium diisopropyl amide (1.89 mmol) in THF (6 mL). After stirring the reaction at −78° C. for 30 minutes 2[N,N-Bis(trifluromethyl-sufonyl)amine]-5-chloropyridine (1.4 g, 3.6 mmol) was added. The reaction was warmed to −20° C. and stirred for 3 hours. The reaction was quenched with saturated $NH_4Cl$ solution, and the resulting mixture was extracted with ethyl acetate, washed with 1N HCl solution, saturated $NaHCO_3$ solution and dried over anhydrous $Na_2SO_4$. The solution was filtered and concentrated in vacuo. The residue was purified on the chromatotron using a 2000-micron rotor ($SiO_2$) and 5% ethyl acetate-hexanes as eluant to afford 393 mg of the desired product as a 2:1 mixture of double bond regio-isomers. $^1H$ NMR (500 MHz, $CDCl_3$): (Major isomer) δ 7.45-7.3 (m, 5H), 6.06 (bt, 1H), 5.41 (s, 2H), 3.56 (bd, 2H). $^1H$ NMR (500 MHz, $CDCl_3$): (Minor isomer) δ 7.45-7.3 (m, 5H), 6.63 (bt, 1H), 5.39 (s, 2H), 3.18 (bd, 2H). LC-MS: (M+H)=370.25.

Example 9.9

5-Propoxy-3-(1H-tetrazol-5-yl)-2,4,5,6-tetrahydro-cyclopentapyrazole (Compound 12)

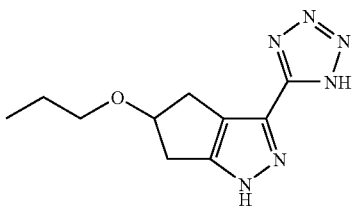 [SMILES: CCCOC1Cc2[nH]nc(-c3nnn[nH]3)c2C1]

Step A: Preparation of 1-Benzyl-5-propoxy-1,4,5,6-tetrahydro-cyclopentapyrazole-3-carbonitrile

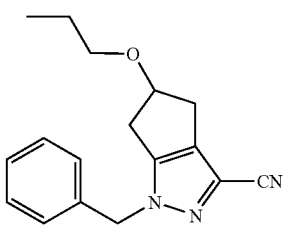 [SMILES: CCCOC1Cc2c(C#N)nn(Cc3ccccc3)c2C1]

To a solution of 1-benzyl-5-hydroxy-1,4,5,6-tetrahydrocyclo-penta[c]pyrazole-3-carbonitrile-(see Example 9.7, 30 mg, 0.125 mmol) in anhydrous DMF (2 mL) was added sodium hydride (6 mg, 0.15 mmol, 60% dispersion in oil). After stirring for 3 minutes propyl bromide was added (14 μL, 0.15 mmol) and the resulting mixture stirred for an hour. At the end of this time sodium hydride (6 mg, 0.15 mmol, 60% dispersion in oil) and propyl bromide were added. After 30 minutes the reaction was quenched by adding saturated $NH_4Cl$ (3 mL). The resulting mixture was extracted with ethyl acetate, washed with brine, dried over anhydrous $Na_2SO_4$, filtered and concentrated in vacuo. The residue was purified by PTLC ($SiO_2$) using 15% ethyl acetate-hexanes to give the desired product.

Step B: Preparation of 1-Benzyl-5-propoxy-3-(2H-tetrazol-5-yl)-1,4,5,6-tetrahydro-cyclopentapyrazole

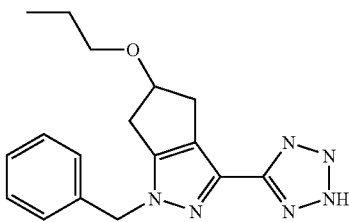 [SMILES: CCCOC1Cc2c(C3=NNNN3)nn(Cc3ccccc3)c2C1]

To a solution of the intermediate from step A (25 mg, 0.089 mmol) in 2-propanol (1 mL) was added water (2 mL), sodium azide (14 mg, 0.222 mmol) and zinc bromide (10 mg, 0.04 mmol). After heating the reaction mixture at 90° C. for 18 hours, it was cooled to room temperature and HCl (3 mL, 3N) was added. The reaction mixture was extracted with ethyl acetate, washed with brine, dried over anhydrous $Na_2SO_4$ filtered and concentrated in vacuo. The residue was purified by PTLC (SiO$_2$) using 100% ethyl acetate to give the desired product.

Step C. 5-Propoxy-3-(1H-tetrazol-5-yl)-2,4,5,6-tetrahydro-cyclopentapyrazole (Compound 12)

To a solution of the intermediate from step B (26 mg, 0.08 mmol) in DMSO (0.6 mL) was added potassium-t-butoxide (0.6 mL, 0.6 mmol, 1.0 M in THF). Oxygen gas was bubbled through the reaction mixture for 15 minutes. The reaction was quenched with HCl (3 mL, 3N). The resulting mixture was extracted with ethyl acetate (5×) dried over anhydrous Na$_2$SO$_4$ filtered and concentrated in vacuo. The residue was purified by reverse phase HPLC to afford the title compound. $^1$H NMR (CDCl$_3$) δ 4.80 (m, 1H), 3.51 (m, 2H), 3.24 (dd, J=6.8, 15.5 Hz, 1H), 3.18 (dd, J=6.9, 16.0 Hz, 1H), 2.85 (dd, J=4.1, 15.6 Hz, 1H), 2.79 (dd, J=4.4, 16.1 Hz, 1H), 1.62 (m, 2H), 0.96 (t, J=7.6 Hz, 3H). LC-MS: 2.15 min; (M+H)=235.

Example 9.10

5-Isobutoxy-3-(1H-tetrazol-5-yl)-2,4,5,6-tetrahydro-cyclopentapyrazole (Compound 15)

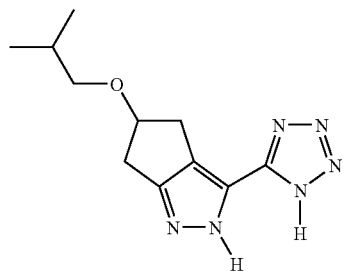 [SMILES: CC(C)COC1Cc2n[nH]c(-c3nnn[nH]3)c2C1]

The title compound was prepared from 1-benzyl-5-hydroxy-1,4,5,6-tetrahydrocyclo-penta[c]pyrazole-3-carbonitrile (see Example 9.7) using a similar procedure described for the synthesis of Example 9.8. $^1$H NMR (CDCl$_3$) δ 4.77 (m, 1H), 3.33 (m, 2H), 3.23 (dd, J=6.9, 15.5 Hz, 1H), 3.17 (dd, J=6.9, 16.0 Hz, 1H), 2.85 (dd, J=4.1, 15.6 Hz, 1H), 2.79 (dd, J=4.2, 15.9 Hz, 1H), 1.85 (m, 1H), 0.94 (d, J=6.7 Hz, 3H). LC-MS: 2.42 min; (M+H)=249.

Example 9.11

5-Butoxy-3-(1H-tetrazol-5-yl)-2,4,5,6-tetra hydro-cyclopentapyrazole (Compound 16)

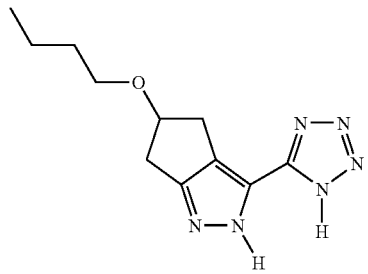 [SMILES: CCCCOC1Cc2n[nH]c(-c3nnn[nH]3)c2C1]

The title compound was prepared from 1-benzyl-5-hydroxy-1,4,5,6-tetrahydrocyclo-penta[c]pyrazole-3-carbonitrile (see Example 9.7) using a similar procedure described for the synthesis of Example 9.8. $^1$H NMR (CDCl$_3$) δ 4.78 (m, 1H), 3.56 (m, 2H), 3.24 (dd, J=6.8, 15.6 Hz, 1H), 3.17 (dd, J=6.9, 15.9 Hz, 1H), 2.84 (dd, J=4.1, 15.6 Hz, 1H), 2.77 (dd, J=4.6, 16.0 Hz, 1H), 1.58 (m, 2H), 1.42 (m, 2H), 0.95 (t, J=7.3 Hz, 3H). LC-MS: 2.50 min; (M+H)=249.

Example 9.12

5-Fluoro-3-(1H-tetrazol-5-yl)-2,4,5,6-tetrahydro-cyclopentapyrazole (Compound 14)

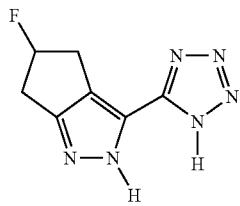 [SMILES: FC1Cc2n[nH]c(-c3nnn[nH]3)c2C1]

Step A: Preparation of 1-Benzyl-5-fluoro-1,4,5,6-tetrahydro-cyclopentapyrazole-3-carbonitrile

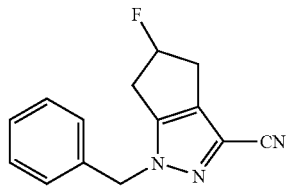 [SMILES: N#Cc1nn(Cc2ccccc2)c2c1CC(F)C2]

To a solution of 1-benzyl-5-hydroxy-1,4,5,6-tetrahydrocyclo-penta[c]pyrazole-3-carbonitrile (see Example 9.7, 30 mg, 0.125 mmol) in anhydrous dichloromethane (0.9 mL) was added DAST (33 μL, 0.25 mmol) under a nitrogen atmosphere. After stirring at room temperature for 15 minutes, the reaction mixture was diluted with ethyl acetate, washed with saturated NaHCO$_3$ solution and brine. The organic layer was dried over anhydrous Na$_2$SO$_4$ filtered and concentrated in vacuo. The residue was purified by PTLC (SiO$_2$) using 30% ethyl acetate-hexanes to give the desired compound (16 mg).

Step B: Preparation of 1-Benzyl-5-fluoro-3-(1H-tetrazol-5-yl)-1,4,5,6-tetrahydro-cyclopentapyrazole

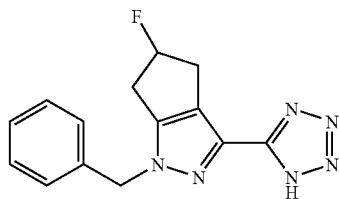 [SMILES: FC1Cc2c(-c3nnn[nH]3)nn(Cc3ccccc3)c2C1]

The compound was prepared from the cyano intermediate from Step A using a similar procedure described in Example 9.8, Step B.

Step C. 5-Fluoro-3-(1H-tetrazol-5-yl)-2,4,5,6-tetrahydro-cyclopentapyrazole (Compound 14)

To a solution of the intermediate from step B (13 mg, 0.04 mmol) in MeOH (1 mL) was added formic acid (0.1 mL) followed by palladium black (10 mg). After stirring the reaction mixture under nitrogen atmosphere for 96 hours, it was filtered and concentrated in vacuo. The residue was purified by reverse phase HPLC (Gilson) to give the title compound (4.9 mg). $^1$H NMR (CD$_3$OD, 500 MHz) δ 5.8 (d, J=51.9 Hz, 1H), 3.31-3.17 (m, 2H), 3.14-2.92 (m, 2H). LC-MS: 0.99 min; (M+H)=195.17.

Example 9.13

5-Propyl-3-(1H-tetrazol-5-yl)-2,4,5,6-tetrahydro-cyclopentapyrazole (Compound 11)

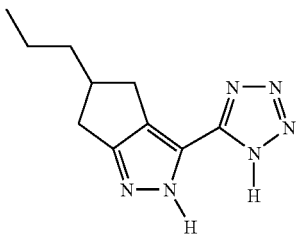

Step A: Preparation of 5-Allyl-1-benzyl-1,6-dihydro-cyclopentapyrazole-3-carbonitrile and 5-Allyl-1-benzyl-1,4-dihydro-cyclopentapyrazole-3-carbonitrile (mixture)

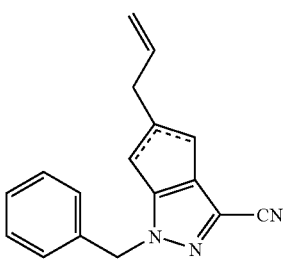

To a solution of the trifluoromethansulfonic ester intermediate described in Example 9.8 (114 mg, 0.307 mmol) in anhydrous THF (2 mL) was added tri-n-butyl allyl tin (112 mg, 0.338 mmol), lithium chloride (39 mg, 0.923 mmol) and tetrakis triphenyl phosphine palladium (0) (7.1 mg, 0.006 mmol). After refuxing the reaction mixture for 6 hours, it was cooled to room temperature and filtered. The residue was concentrated in vacuo and purified on the chromatotron using a 2000-micron rotor (SiO$_2$) and 20% ethyl acetate-hexanes as the eluant to give the desired product (33 mg).

Step B: Preparation of 5-Allyl-1-benzyl-3-(1H-tetrazol-5-yl)-1,6-dihydro-cyclopentapyrazole and 5-Ally-1-benzyl-3-(1H-tetrazol-5-yl)-1,4-dihydro-cyclopentapyrazole (mixture)

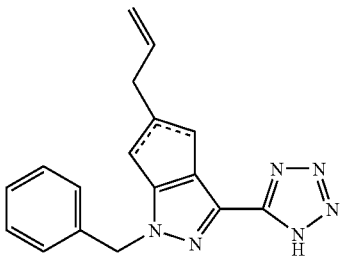

The compound was prepared from the intermediate obtained in step A above using a similar procedure described in Example 9.8, step B.

Step C. 5-Propyl-3-(1H-tetrazol-5-yl)-2,4,5,6-tetrahydro-cyclopentapyrazole

To a solution of the intermediate from step, B (18 mg, 0.059 mmol) in methanol was added a few drops of concentrated HCl until the reaction was homogeneous. Pd/C (1.8 mg) was added and the resulting mixture was stirred under a hydrogen atmosphere (balloon) for 24 hours. The reaction mixture was filtered, concentrated in vacuo and purified by reverse phase HPLC to give the title compound. $^1$H NMR (CD$_3$OD, 500 MHz) δ 3.06 (m, 2H), 2.97 (dd, J=7.5, 15.1 Hz, 1H), 2.5 (m, 2H), 1.6 (m, 2H), 1.4 (m, 2H), 0.98 (t, J=7.3 Hz, 3H). LC-MS: 2.60 min; (M+H)=219.36.

Example 9.14

5-Cyclopentyl-3-(1H-tetrazol-5-yl)-2,4,5,6-tetrahydro-cyclopentapyrazole (Compound 13)

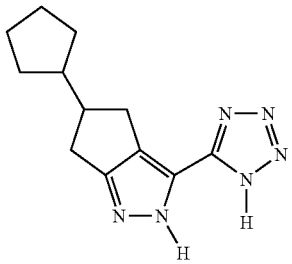 [SMILES: C1CCC(C2Cc3n[nH]c(-c4nnn[nH]4)c3C2)C1]

Step A: Preparation of 1-Benzyl-5-cyclopent-1-enyl-1,6-dihydro-cyclopentapyrazole-3-carbonitrile and 1-Benzyl-5-cyclopent-1-enyl-1,4-dihydro-cyclopentapyrazole-3-carbonitrile (mixture)

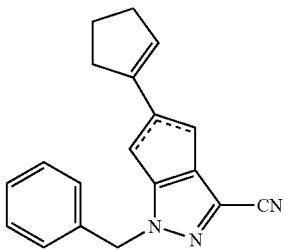

To a solution of the trifluoromethansulfonic ester intermediate described in Example 9.8 (185 mg, 0.501 mmol) in 1,4-dioxane was added cyclopenten-1-yl-boronic acid (62 mg, 0.551 mmol), potassium phosphate (160 mg, 0.751 mmol) and tetrakis triphenyl phosphine palladium (0). The reaction mixture was heated at 85° C. After the reaction was complete, it was diluted with ethyl acetate, washed with 1N NaOH, brine and dried over anhydrous Na$_2$SO$_4$. The solution was filtered and concentrated in vacuo. The residue was purified on the chromatotron using a 2000-micron rotor (SiO$_2$) and 20% ethyl acetate-hexanes as the eluant.

Step B: Preparation of 1-Benzyl-5-cyclopent-1-enyl-3-(1H-tetrazol-5-yl)-1,6-dihydro-cyclopentapyrazole and 1-Benzyl-5-cyclopent-1-enyl-3-(1H-tetrazol-5-yl)-1,4-dihydro-cyclopentapyrazole (mixture)

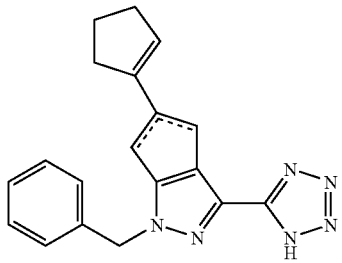

The compound was prepared from the intermediate obtained in step A above using a similar procedure described in Example 9.8, step B.

Step C. 5-Cyclopentyl-3-(1H-tetrazol-5-yl)-2,4,5,6-tetrahydro-cyclopentapyrazole (Compound 13)

To a solution of the intermediate from step B (16 mg, 0.048 mmol) in methanol 2 mL) was added formic acid (200 μL). Palladium black (8.2 mg, 0.078 mmol) was added, and the resulting mixture was purged with nitrogen and stirred for 24 hours. Another portion of palladium black was added (8.2 mg, 0.078 mmol). After stirring for 48 hours, the reaction was filtered, concentrated in vacuo, and purified by reverse phase HPLC to give the title compound. $^1$H NMR (CD$_3$OD, 500 MHz) δ 3.1-2.9 (m, 2H), 2.6 (m, 2H), 2.03 (m, 2H), 1.87 (m, 2H), 1.63 (m, 2H), 1.59 (m, 2H), 1.28 (m, 2H). LC-MS: 2.99 min; (M+H)=245.46.

Example 9.15

5-Butyl-3-(1H-tetrazol-5-yl)-2,4,5,6-tetrahydro-cyclopentapyrazole (Compound 8)

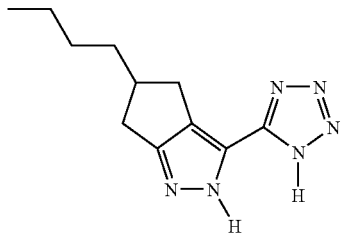 [SMILES: CCCCC1Cc2n[nH]c(-c3nnn[nH]3)c2C1]

Step A: Preparation of 1-Benzyl-5-butyl-1,6-dihydro-cyclopentapyrazole-3-carbonitrile and 1-Benzyl-5-butyl-1,4-dihydro-cyclopentapyrazole-3-carbonitrile (mixture)

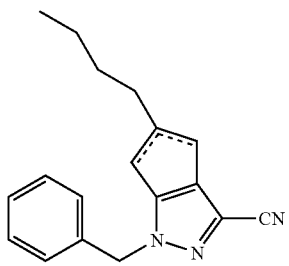

To a solution of the trifluoromethansulfonic ester intermediate described in Example 9.8 (180 mg, 0.486 mmol) in toluene (3 mL) was added n-butyl boronic acid (99 mg, 0.973 mmol), K$_2$CO$_3$ (201 mg, 1.46 mmol), PdCl$_2$(dppf)$_2$ (12 mg, 0.0146 mmol) and Ag$_2$O (225 mg, 0.973 mmol). After refluxing the reaction mixture for 6 hours, it was cooled to room temperature and filtered. The residue was concentrated in vacuo and purified on the chromatotron using a 2000-micron rotor (SiO$_2$) and 5% ethyl acetate-20% ethyl acetate-hexanes as the eluant to give the desired product (52 mg).

Step B: Preparation of 1-Benzyl-5-butyl-3-(1H-tetrazol-5-yl)-1,6-dihydro-cyclopentapyrazole and 1-Benzyl-5-butyl-3-(1H-tetrazol-5-yl)-1,4-dihydro-cyclopentapyrazole (mixture)

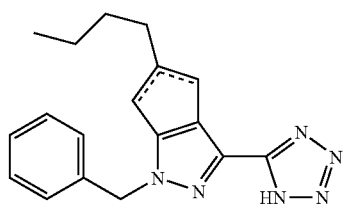

The compound was prepared from the intermediate obtained in step A above using a similar procedure described in Example 9.8 step B.

Step C. 5-Butyl-3-(1H-tetrazol-5-yl)-2,4,5,6-tetrahydro-cyclopentapyrazole (Compound 8)

The compound was prepared from the intermediate obtained in step B above using a similar procedure described in Example 5 step C. $^1$H NMR (CD$_3$OD, 500 MHz) δ 3.1 (m, 2H), 2.9 (m, 1H), 2.5 (m, 2H), 1.6 (m, 2H), 1.4 (m, 4H), 0.9 (t, J=7.0 Hz, 3H). LC-MS: 2.86 min; (M+H)=233.34.

Example 9.16

5-Methyl-3-(1H-tetrazol-5-yl)-2,6-dihydro-cyclopentapyrazole (Compound 9) and 5-Methyl-3-(1H-tetrazol-5-yl)-2,4-dihydro-cyclopentapyrazole (Compound 10)

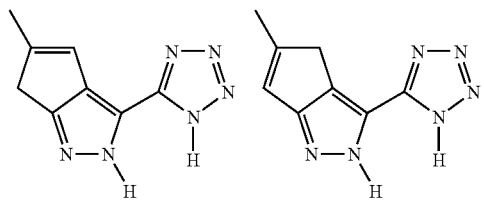

Step A: Preparation of 5Ethoxy-1,4-dihydro-cyclopentapyrazole-3-carboxylic acid tert-butyl ester

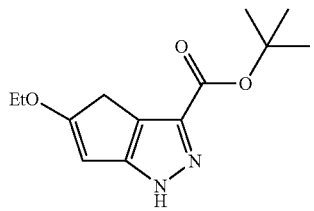 [SMILES: CCOC1=Cc2[nH]nc(C(=O)OC(C)(C)C)c2C1]

To an ethanol (5 mL) solution of the ketoester (254 mg, 1.0 mmol), prepared from 3-ethoxy cyclopentenone as in step A of Example 9.8 above, was added hydrazine hydrate (34 µL, 1.1 mmol), followed by acetic acid (0.5 mL). After refluxing the reaction mixture for 1.5 hours, it was cooled to room temperature and concentrated in vacuo. The residue was suspended in water and extracted with ethyl acetate. The organic layer was dried over anhydrous Na₂SO₄, filtered and concentrated in vacuo. The residue was purified by flash chromatography (SiO₂) using 25% ethyl acetate-hexanes to give the desired product as a white solid.

Step B: Preparation of 5-Ethoxy-1-(toluene-4-sulfonyl)-1,4-dihydro-cyclopentapyrazole-3-carboxylic acid tert-butyl ester

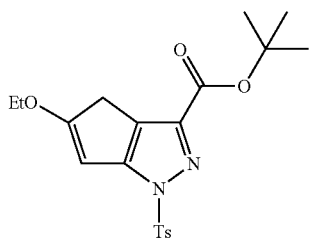 [SMILES: CCOC1=Cc2c(c(C(=O)OC(C)(C)C)nn2S(=O)(=O)c2ccc(C)cc2)C1]

To a solution of the pyrazole intermediate from step A (275 mg, 1.1 mmol) above in CH₂Cl₂ (5 mL) was added pyridine (178 µL, 2.2 mmol) and p-toluene sulfonyl chloride (230 mg, 1.21 mmol). After stirring the resulting reaction mixture at room temperature for 3 hours it was diluted with CH₂Cl₂, washed with 1N HCl, saturated NaHCO₃, dried over anhydrous Na₂SO₄, filtered and concentrated in vacuo. The residue was purified by flash chromatography (SiO₂) using 10% ethyl acetate-hexanes.

Step C: Preparation of 5-Oxo-1-(toluene-4-sulfonyl)-1,4,5,6-tetrahydro-cyclopentapyrazole-3-carboxylic acid

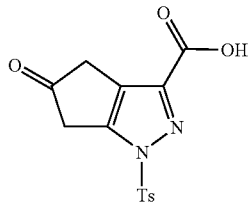 [SMILES: Cc1ccc(S(=O)(=O)n2nc(C(=O)O)c3c2CC(=O)C3)cc1]

To a solution of the intermediate from step B above, (414 mg, 1.02 mmol) in CH₂Cl₂ (2 mL) was added trifluoroacetic acid (2 mL). After stirring the reaction at room temperature for 1.5 hours it was concentrated in vacuo and azeotroped with toluene (2×). This material was used in the next step without any further purification.

Step D: Preparation of 5-Oxo-1-(toluene-4-sulfonyl)-1,4,5,6-tetrahydro-cyclopentapyrazole-3-carboxylic acid 2,5-dioxo-pyrrolidin-1-yl ester

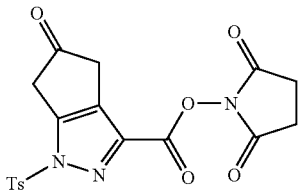 [SMILES: Cc1ccc(S(=O)(=O)n2nc(C(=O)ON3C(=O)CCC3=O)c3c2CC(=O)C3)cc1]

To a solution of the intermediate from step C above, (320 mg, 1.0 mmol) in CH₂Cl₂ (20 mL) was added N-hydroxy succinimide (230 mg, 2.0 mmol) followed by EDC (384 mg, 2.0 mmol). After stirring at room temperature for 18 hours, the reaction mixture was concentrated in vacuo. The residue was diluted with ethyl acetate (20 mL), washed with saturated NaHCO₃, solution and brine. The organic layer was dried over anhydrous Na₂SO₄, filtered and concentrated in vacuo. A yellow solid was obtained.

Step E: Preparation of 5-Oxo-1-(toluene-4-sulfonyl)-1,4,5,6-tetrahydro-cyclopentapyrazole-3-carboxylic acid amide

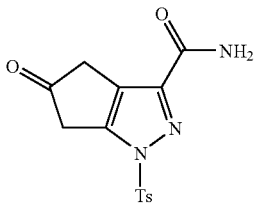 [SMILES: Cc1ccc(S(=O)(=O)n2nc(C(N)=O)c3c2CC(=O)C3)cc1]

To a solution of the intermediate from step D above, (380 mg, 0.91 mmol) in 1,4-dioxane (10 mL) was added NH₄OH (14.8 N, 10.0 eq, 0.61 mL). A precipitate formed immediately. After stirring at room temperature for 15 minutes the reaction mixture was filtered through a sintered funnel and the precipitate washed with 1,4-dioxane. The filtrate was concentrated in vacuo to give a yellow oil.

Step F: Preparation of 5-Oxo-1-(toluene-4-sulfonyl)-1,4,5,6-tetrahydro-cyclopentapyrazole-3-carbonitrile

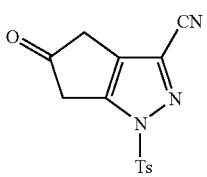

To a solution of the intermediate from step E above (0.91 mmol) in anhydrous DMF (5 mL) was added cyanuric chloride (334 mg, 2.0 mmol) in two portions. After stirring at room temperature for 15 minutes, the reaction was quenched by pouring into water (10 mL). The resulting mixture was extracted with ethyl acetate, washed with saturated NaHCO₃, brine, dried over anhydrous Na₂SO₄, filtered and concentrated in vacuo. The residue was purified by flash chromatography (SiO$_2$) using 25% ethyl acetate-hexaries. A white solid was obtained.

Step G: Preparation of Trifluoro-methanesulfonic acid 3-cyano-1-(toluene-4-sulfonyl)-1,6-dihydro-cyclopentapyrazol-5-yl ester and Trifluoro-methanesulfonic acid 3-cyano-1-(toluene-4-sulfonyl)-1,4-dihydro-cyclopentapyrazol-5-yl ester (mixture)

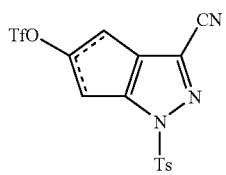

To a solution of the intermediate from step F (100 mg, 0.33 mmol) in anhydrous THF (5 mL) at −78° C. was added a solution of lithium diisopropyl amide (0.33 mmol, 166 μL, 2.0 M in THF) in THF (6 mL). After stirring the reaction at −78° C. for 30 minutes 2[N,N-Bis(trifluromethylsufonyl)amine]-5-chloropyridine (195 mg, 0.496 mmol) was added. The reaction was warmed to 0° C. and stirred for 45 minutes. The reaction was quenched with 1N HCl solution, and the resulting mixture was extracted with ethyl acetate, washed with saturated NaHCO$_3$ solution and dried over anhydrous Na$_2$SO$_4$. The solution was filtered and concentrated in vacuo. The residue was purified by flash chromatography (SiO$_2$) using 5% ethyl acetate-hexanes as eluant to afford 79 mg of the desired product as a 4:1 mixture of double bond regio-isomers.

Step H: Preparation of 5-Methyl-1-(toluene-4-sulfonyl)-1,6-dihydro-cyclopentapyrazole-3-carbon itrile and 5-Methyl-1-(toluene-4-sulfonyl)-1,4-dihydro-cyclopentapyrazole-3-carbonitrile (mixture)

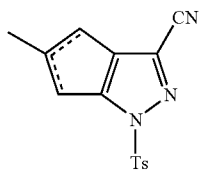

To a solution of the intermediate from step G above, (79 mg, 0.182 mmol) in toluene (1.5 mL) was added lithium chloride (39 mg, 0.912 mmol), tetramethyl tin (126 μL, 0.912 mmol) and tetrakis triphenyl phosphine palladium (0). After refluxing the reaction mixture for 45 minutes it was cooled to room temperature, diluted with ethyl acetate, washed with water. The organic layer was dried over anhydrous Na$_2$SO$_4$, filtered and concentrated in vacuo. The residue was purified by flash chromatography (SiO$_2$) using 30% ethyl aceate-hexanes to give (28 mg) the desired product.

Step I: Preparation of 5-Methyl-1,6-dihydro-cyclopentapyrazole-3-carbonitrile and 5-Methyl-1,4-dihydro-cyclopenta pyrazole-3-carbonitrile (mixture)

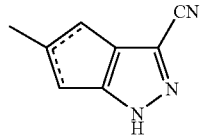

To a solution of the intermediate from step H above, (28 mg, 0.093 mmol) in anhydrous THF (3 mL) was added tetrabutyl ammonium fluoride (93 μL, 0.093 mmol, 1.0 M in THF). After refluxing the reaction mixture for 30 minutes, it was cooled to room temperature and concentrated in vacuo. The residue was dissolved in ethyl acetate, washed with saturated NaHCO$_3$, brine, dried over anhydrous Na$_2$SO$_4$, filtered and concentrated in vacuo. The residue was purified by flash chromatography (SiO$_2$) using 30% ethyl acetate-hexanes to give a white solid.

Step J: 5-Methyl-3-(1H-tetrazol-5-yl)-2,6-dihydro-cyclopentapyrazole (Compound 9) and 5-Methyl-3-(1H-tetrazol-5-yl)-2,4-dihydro-cyclopentapyrazole (Compound 10)

To a solution of the intermediate from step I above (9.0 mg, 0.062 mmol) in 2-propanol (1 mL) was added water (0.5 mL), sodium azide (12 mg, 0.186 mmol) and zinc bromide (6.5 mg, 0.031 mmol). After heating the reaction mixture at 90° C. for 18 hours, it was cooled to room temperature and HCl (1.5 mL, 3N) was added. The reaction mixture was extracted with ethyl acetate, washed with brine, dried over anhydrous Na$_2$SO$_4$ filtered and concentrated in vacuo to give the desired product as a 2:1 ratio of double bond regio-isomers. Isomer (a): $^1$H NMR (CD$_3$OD, 500 MHz) δ 6.43 (bs, 1H), 3.3 (s, 2H), 2.2 (s, 3H). Isomer (b): $^1$H NMR (CD$_3$OD, 500 MHz) δ 6.58 (bs, 1H), 3.24 (s, 2H), 2.15 (s, 3H). LC-MS: 1.86 min, (M+H)=189.1

Throughout this application, various publications, patents and published patent applications are cited. The disclosures of these publications, patents and published patent applications referenced in this application are hereby incorporated by reference in their entirety into the present disclosure. Modifications and extension of the disclosed inventions that are within the purview of the skilled artisan are encompassed within the above disclosure and the claims that follow.

Although a variety of expression vectors are available to those in the art, for purposes of utilization for both the endogenous and non-endogenous human GPCRs, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

What is claimed is:
1. A compound, which is 3-(1H-tetrazol-5-yl)-2,4,5,6-tetrahydro-cyclopentapyrazole, or a pharmaceutically acceptable salt, solvate or hydrate thereof.

2. A pharmaceutical composition comprising 3-(1H-tetrazol-5-yl)-2,4,5,6-tetrahydro-cyclopentapyrazole, or a pharmaceutically acceptable salt, solvate or hydrate thereof, in combination with a pharmaceutically acceptable carrier.

* * * * *